US008440415B2

(12) United States Patent
Lobanenkov et al.

(10) Patent No.: US 8,440,415 B2
(45) Date of Patent: May 14, 2013

(54) BORIS ISOFORMS AND METHODS OF DETECTING AND TREATING DISEASE

(75) Inventors: Victor V. Lobanenkov, Rockville, MD (US); Elena Pugacheva, Germantown, MD (US); Dmitri Loukinov, Germantown, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 0 days.

(21) Appl. No.: 13/478,779

(22) Filed: May 23, 2012

(65) Prior Publication Data

US 2012/0237520 A1 Sep. 20, 2012

Related U.S. Application Data

(62) Division of application No. 12/439,063, filed as application No. PCT/US2007/077281 on Aug. 30, 2007, now Pat. No. 8,206,933.

(60) Provisional application No. 60/841,342, filed on Aug. 31, 2006.

(51) Int. Cl.
*G01N 33/53* (2006.01)

(52) U.S. Cl.
USPC ............................................ 435/7.1; 436/518

(58) Field of Classification Search ........................ None
See application file for complete search history.

(56) References Cited

U.S. PATENT DOCUMENTS

2005/0182249 A1 8/2005 Lobanenkov et al.

FOREIGN PATENT DOCUMENTS

| WO | WO 03/072799 A2 | 9/2003 |
| WO | WO 2006/034335 A2 | 3/2006 |

OTHER PUBLICATIONS

D'Arcy et al. (Clin. Cancer Res 2006 vol. 12, p. 5978-5986).*
Klenova et al., "The novel *Boris + CTCF* gene family is uniquely involved in the epigenetics of normal biology and cancer," *seminars in Cancer Biology*, 12, 399-414 (2002).
Loukinov et al., "BORIS, a novel male germ-line-specific protein associated with epigenetic reprogramming events, shares, the same 11-zinc-finger domain with CTCF, the insulator protein involved in reading imprinting marks in the soma," *PNAS*, 99 (10), 6806-6811 (2002).
Renaud et al., "Characterization of alternative promoters for alternative forms of BORIS-like transcripts," *Proceedings of the American Association for Cancer Research Annual Meetings*, 46 (#1947), 456 (2005).
Renaud et al., "Expression of the CTCF-paralogous cancer testis gene, brother of the regulator of imprinted sites (Boris), is regulated by three alternative promoters modulated by CpG methylation and by CTCF and p53 transcription factors," *Nucleic Acids Research*, 35 (21), 7372-7388 (2007).
UniProt Consortium, Accession No. A6XGM0, 2007.
International Search Report and Written Opinion of PCT/US2007/077281, European Patent Office, dated Mar. 28, 2008.
Pugacheva, et al., The Structural Complexity of the Human BORIS Gene in Gametogenesis and Cancer, PLOS ONE, Nov. 2010, vol. 5, Issue 1, e13872.
Japanese Patent Office, First Examination Report in Japanese Patent Application No. 526917/2009 (Oct. 9, 2012).
Konishi et al., "Expression of Boris (CTCFL) mRNA in breast cancer cell line and knockdown thereof by siRNA," *Journal of Japan Surgical Society*, 107, Extra Edition (2), 669, Ps-149-2 (Mar. 5, 2006) Abstract.
Loukinov et al., "Antitumor Efficacy of DNA Vaccination to the Epigenetically Acting Tumor Promoting Transcription Factors Boris and CD80 Molecular Adjuvant," *Journal of Cellular Biochemistry*, 98, 1037-1043 (2006).
Renaud et al., "Implication of DNA methylation, CTCF and BORIS factors in the transcriptional regulation of the human telomerase catalytic subunit hTERT," *Database: Bibliotheque Numerique RERO DOC* [online], Notice #5527, 183-202 (Feb. 28, 2006) [retrieved on Oct. 2, 2012, URL,doc.rero.ch/lm .php?url=1000,40,5, 20060228172017-D1/1_TheseBM_Renaud, pdf.

* cited by examiner

*Primary Examiner* — Jacob Cheu
(74) *Attorney, Agent, or Firm* — Leydig, Voit & Mayer, Ltd.

(57) ABSTRACT

A method of detecting a proliferative disease, such as a disease associated with the abnormal expression of BORIS, in a mammal comprising testing for the expression of a BORIS isoform in the tissue of a mammal that does not express BORIS in the absence of disease, as well as a method of treating or preventing such a disease, isolated or purified BORIS isoform polypeptides and nucleic acids, and kits and arrays comprising same.

17 Claims, 4 Drawing Sheets

US 8,440,415 B2

BORIS ISOFORMS AND METHODS OF DETECTING AND TREATING DISEASE

CROSS-REFERENCE TO RELATED APPLICATIONS

This patent application is a divisional of copending U.S. patent application Ser. No. 12/439,063, filed May 19, 2009, which claims the benefit of U.S. Provisional Patent Application No. 60/841,342, filed Aug. 31, 2006, which is incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 161,782 bytes Byte ASCII (Text) file named "710345_ST25.txt," created on May 2, 2012.

FIELD OF THE INVENTION

This invention pertains to BORIS isoform polypeptides and related compounds and compositions, and to the use of such polypeptides, compounds, and compositions for the detection and treatment of diseases associated with abnormal BORIS expression, such as cancer.

BACKGROUND OF THE INVENTION

The identification of tumor-associated antigens recognized by a mammalian immune system is useful for the diagnosis and treatment of cancer. A variety of tumor-associated antigens have been identified, including cancer/testis antigens that are expressed in cancer cells, but not in normal tissues other than testis. Only a minority of tumor-associated antigens, however, are immunogenic to the mammal that produces them.

BORIS (Brother of the Regulator of Imprinted Sites) is a tumor-associated antigen, which is activated in a wide range of human cancers. In fact, aberrant synthesis of the BORIS gene product has been found in over 300 primary tumors and cancer cell lines representing all major types of human cancers with recurrent 20q13 chromosomal gains. BORIS activation has also been found in all of the standard NCI-60 cancer cell lines, which are maintained by the National Cancer Institute (NCI), and which are thought to be a reasonably complete representative set of human cancers.

BORIS also is a CTCF paralog, which contains all eleven zinc fingers of CTCF, and has been shown to promote cell growth leading to transformation (see Loukinov et al, *Proc. Natl. Acad. Sci* (USA) 99, 6806-6811 (2002), and International Patent Application Publication WO 03/072799 (PCT/US03/05186)). BORIS has, therefore, also been referred to as "CTCF-like" or "CTCFL" protein. One mechanism of action by which BORIS is thought to cause cancer through interference with the maintenance of an appropriate methylation pattern in the genome mediated by CCCTC binding factor (CTCF) (see Klenova et al., *Seminars in Cancer Biology* 12, 399-414 (2002)). The BORIS gene is believed to map to the cancer-associated amplification region of chromosome 20q13.

The detection of aberrant expression of cancer markers, such as prostate specific antigen (PSA) and carcinoembryonic antigen (CEA), are known in the art. These assays, however, detect only a limited number of cancers and have limited positive predictive value for the detection or prognosis of new or recurring cancer. Accordingly, there is a need in the art to identify additional antigens whose expression can be linked to hyperproliferative diseases, such as cancer, as well as methods of detecting the presence of such antigens to aid in the detection, diagnosis, prognostication, or research of such disease states.

The invention provides methods and compositions useful for the detection, diagnosis, prognostication, or research of diseases associated with abnormal BORIS expression, such as cancer. These and other advantages of the invention, as well as additional inventive features, will be apparent from the description of the invention provided herein.

BRIEF SUMMARY OF THE INVENTION

The invention provides a method of detecting a disease characterized by abnormal BORIS expression in a mammal, including but not limited to cancer, which method comprises testing for the expression of one or more BORIS isoforms in a tissue or body fluid of a mammal that does not express the BORIS isoform in the absence of disease.

The invention also provides a method of detecting a disease characterized by abnormal BORIS expression in a mammal, which method comprises testing for the expression of one or more BORIS isoform mRNA transcripts in a tissue or body fluid of a mammal that does not express the BORIS isoform in the absence of disease.

Also provided herein is a method of treating or preventing a disease associated with abnormal BORIS expression in a mammal. In one aspect, the method comprises administering a short interfering RNA (siRNA) molecule to a mammal afflicted with a disease associated with abnormal BORIS expression, wherein the siRNA molecule comprises a sequence of at least 10 contiguous nucleotides that is complimentary to a BORIS isoform mRNA transcript. In a related aspect, the method comprises administering an anti-BORIS antibody to a mammal afflicted with a disease associated with abnormal BORIS expression, wherein the anti-BORIS antibody selectively binds to a isoform polypeptide.

The invention additionally provides a method of inducing an immune response in a mammal comprising administering a BORIS isoform to the mammal.

The invention further provides an isolated or purified polypeptide comprising an amino acid sequence selected from the group consisting of SEQ ID NOs: 25-42, an isolated or purified nucleic acid comprising a nucleotide sequence selected from the group consisting of SEQ ID NOs: 1-24, and a composition comprising such a polypeptide or nucleic acid.

In a related aspect, the invention provides a kit for the detection of BORIS expression in a mammal, which kit comprises (a) a probe set comprising one or more probes that bind to (i) a BORIS polypeptide comprising an amino acid sequence selected from the group consisting of SEQ ID NOs: 25-42, (ii) an auto-antibody to a BORIS polypeptide comprising an amino acid sequence selected from the group consisting of SEQ ID NOs: 25-42, or (iii) a BORIS isoform mRNA transcript comprising a nucleic acid sequence selected from the group consisting of SEQ ID NOs: 1-24, and (b) a reagent that facilitates the detection of the probe.

An array useful for the detection of BORIS expression in a mammal also is provided by the invention, the array comprising one or more probes immobilized on a substrate, wherein the probes bind to (i) a BORIS isoform comprising an amino acid sequence selected from the group consisting of SEQ ID NOs: 25-42, (ii) an auto-antibody to a BORIS isoform comprising an amino acid sequence selected from the group consisting of SEQ ID NOs: 25-42, or (iii) an BORIS isoform mRNA transcript comprising a nucleotide sequence selected from the group consisting of SEQ ID NOs: 1-24.

The invention further provides a database comprising a BORIS expression profile of one or more different types of cancer, wherein the database facilitates the comparison of a BORIS expression profile of a patient with the BORIS expression profile of one or more different types of cancer.

Also provided by the invention is a method of inducing an immune response to BORIS in a mammal comprising administering to the mammal a BORIS isoform comprising an amino acid sequence selected from the group consisting of SEQ ID NOs: 25-42.

DETAILED DESCRIPTION OF THE INVENTION

Figure 1A:
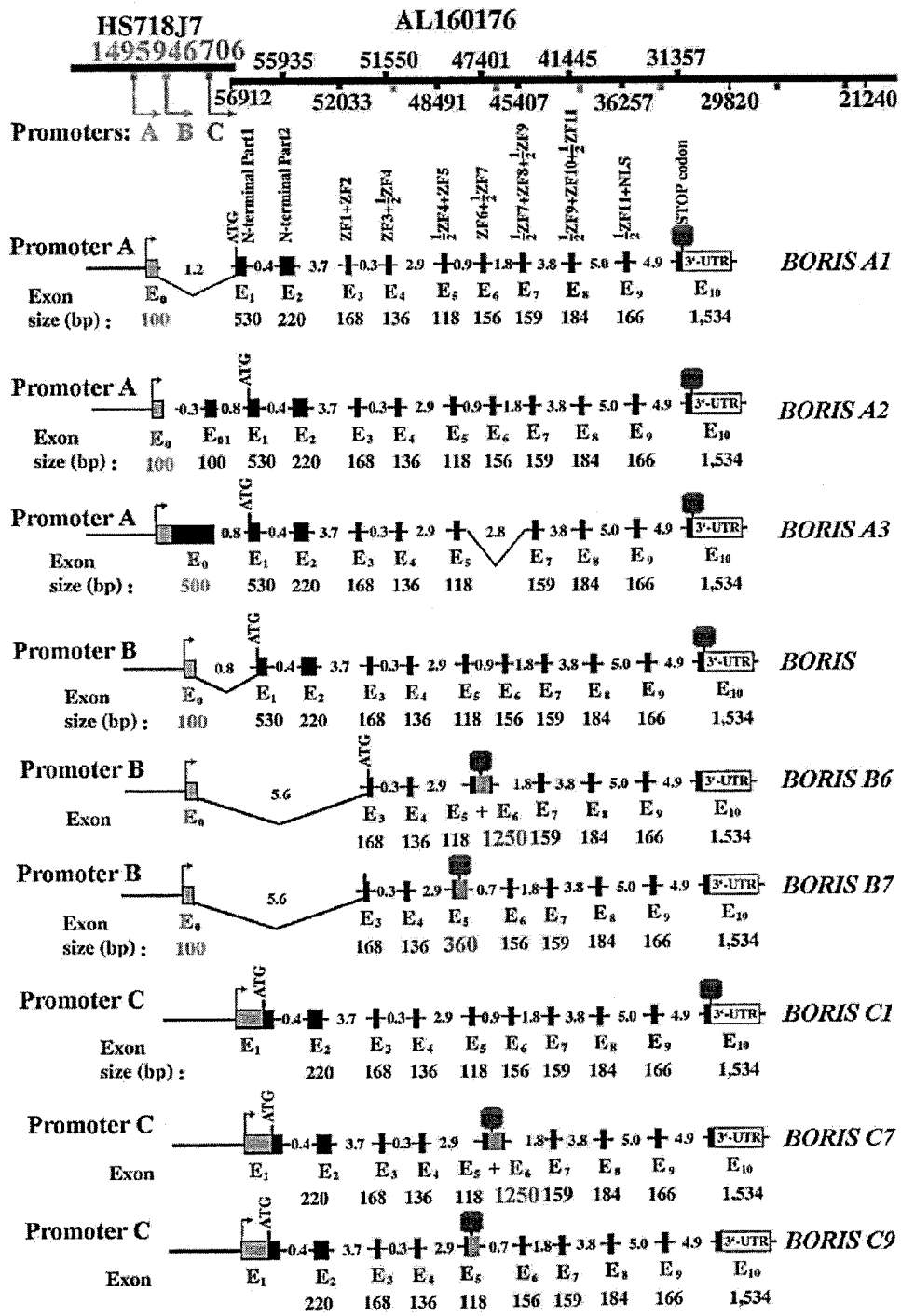
FIGS. 1A-1D are illustrations depicting alternative splice variants expressed by the BORIS gene in the human testes.
Figure 1B:
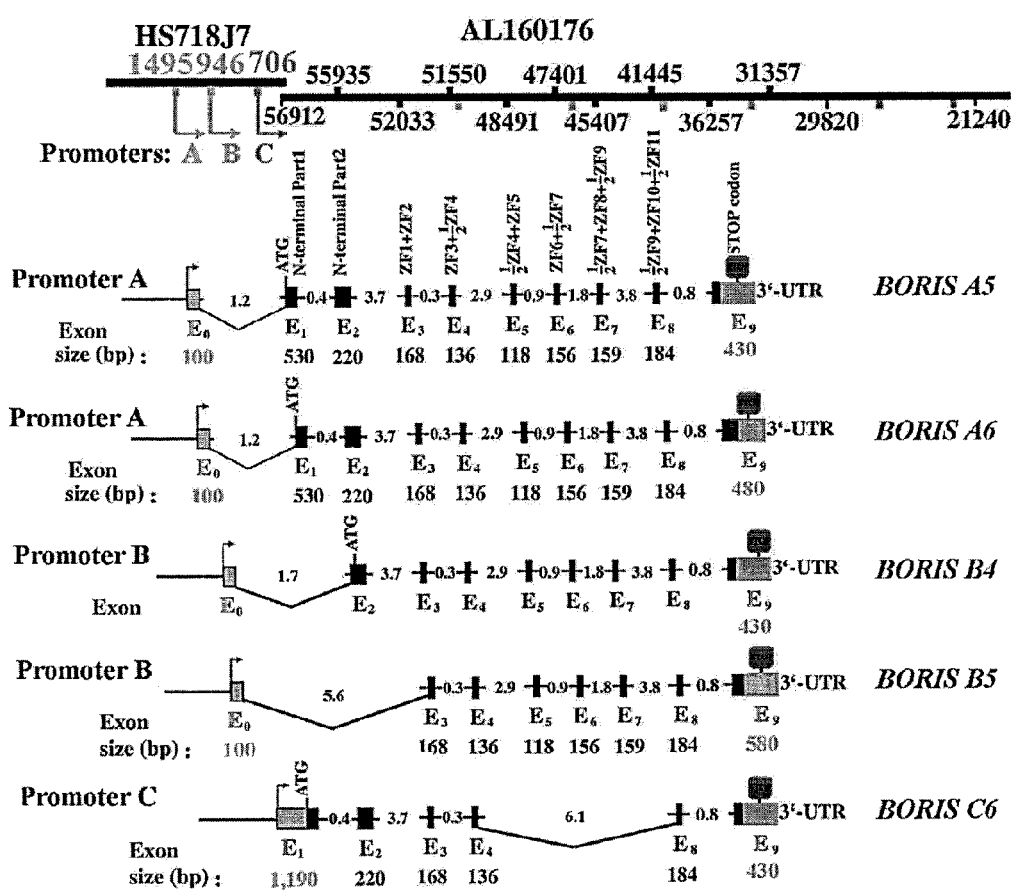
Figure 1C:
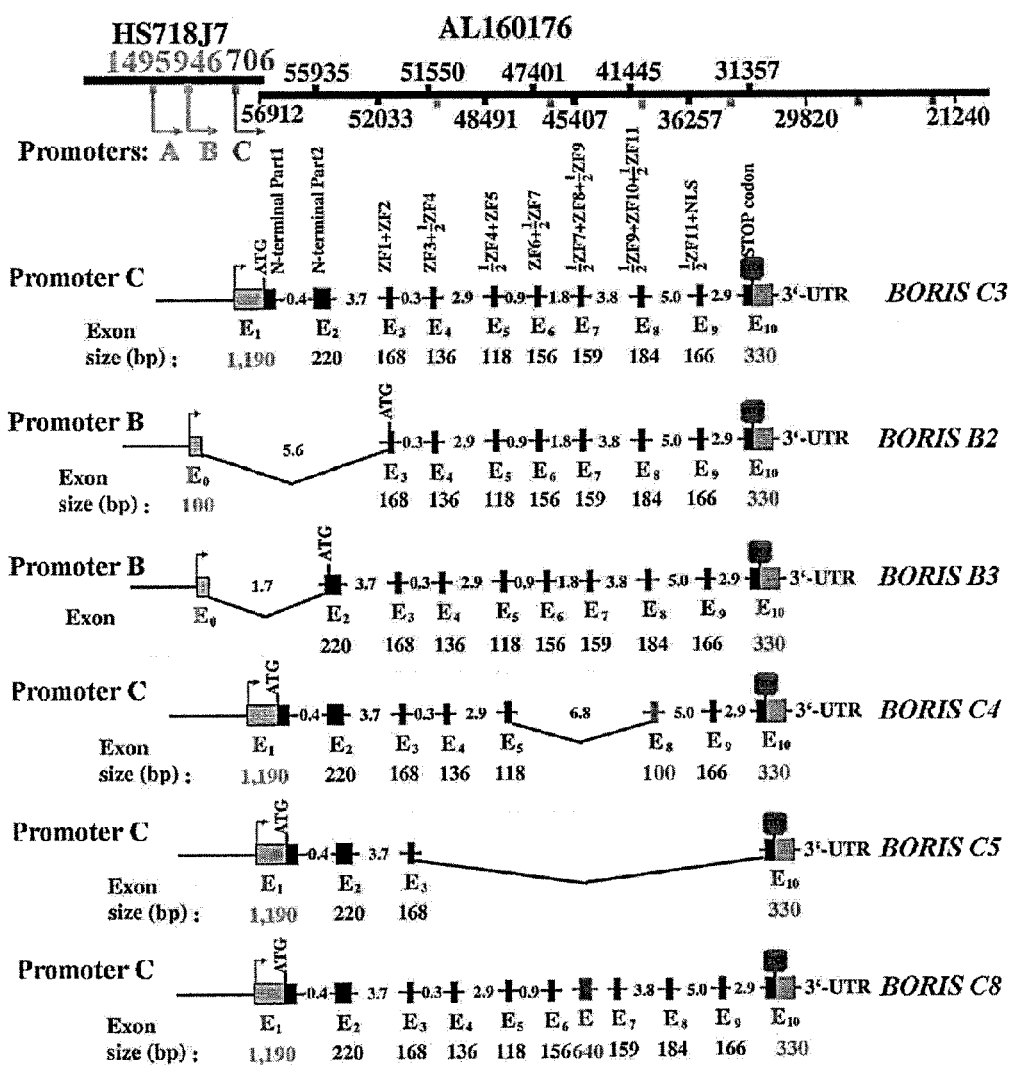
Figure 1D:
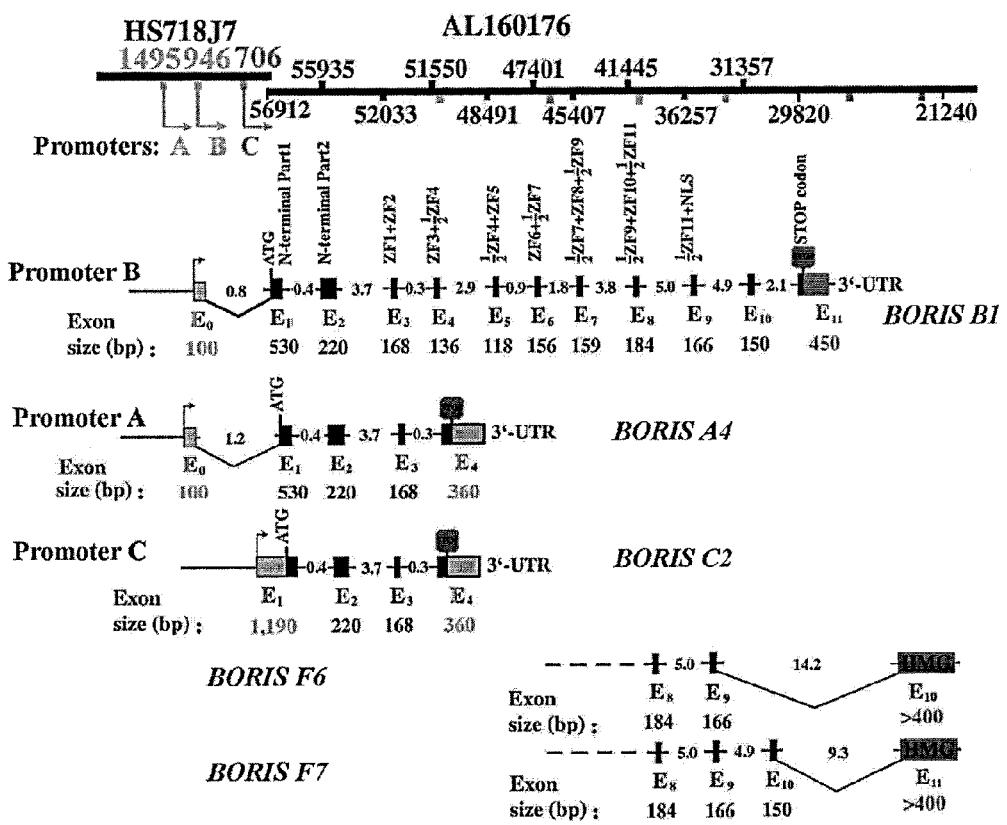

The BORIS polypeptide disclosed in Klenova et al., *Seminars in Cancer Biology* 12, 399-414 (2002) comprises the amino acid sequence provided herein as SEQ ID NO: 43, and is encoded by the mRNA sequence provided herein as SEQ ID NO: 44. This BORIS polypeptide, however, is only one of a family of polypeptides encoded by the BORIS gene. BORIS mRNA splice variants encoding BORIS and BORIS isoforms are described herein, including twenty-four specific examples of BORIS isoform mRNA transcripts that encode seventeen different BORIS isoform polypeptides. The exemplary BORIS isoform mRNA transcripts each comprise a nucleic acid sequence of SEQ ID NOs: 1-24, and the seventeen BORIS isoform polypeptides comprise a nucleotide sequence of SEQ ID NOs: 25-42. The BORIS isoform mRNA transcripts and the polypeptides encoded thereby are set forth in Table 1. In particular, the BORIS isoform mRNA transcripts comprising the nucleotide sequences of SEQ ID NOs: 1, 2, and 3 encode a polypeptide comprising an amino acid sequence identical to that of the previously disclosed BORIS polypeptide (e.g., SEQ ID NO: 43). Although these mRNA transcripts encode the same BORIS polypeptide, the mRNA transcripts are, themselves, alternative spice variants of the previously disclosed BORIS mRNA and, therefore, comprise different nucleotide sequences. The other BORIS isoform polypeptides comprise amino acid sequences that are different from the BORIS polypeptide previously disclosed in Klenova et al., supra.

For the purposes of describing the invention, the terms "BORIS" and "BORIS polypeptide" shall be used to refer to the BORIS polypeptide comprising the amino acid sequence of SEQ ID NO: 43, and the term "BORIS mRNA" shall be used to refer to an mRNA transcript having a nucleotide sequence of SEQ ID NO: 44.

The terms "BORIS isoform" and "BORIS isoform polypeptide" shall be used herein to refer to a polypeptide encoded by a splice variant mRNA transcript of the BORIS gene, which has an amino acid sequence that is different from SEQ ID NO: 43. Examples of BORIS isoform polypeptides include polypeptides comprising an amino acid sequence selected from the group consisting of SEQ ID NOs: 25-42. The term "BORIS isoform mRNA" shall be used to refer to an mRNA splice variant of the BORIS gene, which has a nucleotide sequence that is different from SEQ ID NO: 44. Examples of BORIS isoform mRNA transcripts include mRNA molecules that comprise a nucleic acid sequence encoding an amino acid sequence selected from the group consisting of SEQ ID NOs: 25-42, or a nucleic acid sequence selected from the group consisting of SEQ ID NOs: 1-24.

The term "BORIS gene" shall be used herein to refer to the genomic sequence of BORIS, which encodes the BORIS polypeptide as well as the BORIS mRNA splice variants (e.g., BORIS isoform mRNA transcripts) and BORIS isoform polypeptides.

As used herein, the term "isolated" means the removal of a nucleic acid or polypeptide molecule from its natural environment. The term "purified" means that a given nucleic acid or polypeptide molecule, whether it has been removed from nature or synthesized and/or amplified under laboratory conditions, has been increased in purity, wherein "purity" is a relative term, not "absolute purity."

As used herein, the term "nucleic acid" is intended to encompass a polymer of DNA or RNA, (i.e., a polynucleotide), which can be single-stranded or double-stranded and which can contain non-natural or altered nucleotides. Similarly, a "polypeptide" is intended to encompass a linear sequence of amino acids (i.e., a primary protein structure) of any length, as well secondary, tertiary, and quaternary protein structures, any of which can contain non-natural or altered amino acids.

Some aspects of the invention are described with reference to the use of an antibody. It is intended that the use of an antibody can be substituted by the use of an antibody fragment of any of the various known forms (e.g., F(ab)2' fragments, single chain antibody variable region fragment (ScFv) chains, and the like). Thus, for the sake of brevity, term "antibody" as used herein is intended to encompass antibodies as well as antibody fragments. Wherever the term "antibody" is used, it is specifically contemplated that an antibody fragment can be used instead.

The term "selectively binds" as used herein means to bind to a target molecule (e.g., polypeptide or nucleic acid) with a greater affinity or with preference as compared to another polypeptide or nucleic acid. Thus, for instance, a probe selectively binds a target BORIS isoform mRNA transcript if it binds such target with preference or greater affinity than to a nucleic acid that is not a BORIS isoform mRNA transcript. Similarly, an anti-BORIS antibody selectively binds a BORIS isoform if it binds such target isoform with preference or greater affinity than to a polypeptide that is not a BORIS isoform. Selectively binds also can be used to mean that a molecule binds one BORIS isoform polypeptide or mRNA transcript with preference, or greater affinity, than another BORIS isoform polypeptide or mRNA transcript.

The invention provides a method of detecting a disease characterized by abnormal gene expression, such as a hyperproliferative disease involving abnormal BORIS expression (e.g., cancer) in a mammal. In this respect, "abnormal BORIS expression" means the expression of BORIS in the tissues or body fluids of a mammal that do not express the BORIS gene in the absence of disease, as discussed in greater detail herein.

According to one aspect of the invention, the method comprises testing for the expression of one or more BORIS isoforms in a tissue or body fluid of a mammal that does not express the BORIS isoform in the absence of disease. The one or more BORIS isoforms can, for example, comprise an amino acid sequence selected from the group consisting of SEQ ID NOs: 25-42. In a related aspect of the invention, the method comprises testing for the expression of one or more BORIS isoform mRNA transcripts in a tissue or body fluid of a mammal that does not express the BORIS isoform mRNA in the absence of disease. The one or more BORIS isoform mRNA transcripts can comprise a nucleotide sequence selected from the group consisting of SEQ ID NOs: 1-24. The expression of a BORIS isoform or BORIS isoform mRNA transcript, as described above, in such a tissue or fluid of the mammal is indicative of the presence of disease in the mammal.

The terms "testing" and "detecting" (and permutations thereof) as used herein mean to investigate or determine the presence of a condition. Thus, for instance, "testing for" or "detecting" the expression of a gene or gene product means to investigate or determine whether the gene is being expressed or the gene product is present.

Preferably, the method of detecting a disease comprises testing for the expression of more than one BORIS isoform. For instance, the method can comprise testing for the expression of two or more BORIS isoform polypeptides or BORIS isoform mRNA transcripts, preferably five or more, 10 or more, 15 or more, or even all of such BORIS isoform polypeptides or mRNA transcripts. Whether the method involves the detection of one BORIS isoform polypeptide or BORIS isoform mRNA transcript, or more than one of BORIS isoform polypeptides or BORIS isoform mRNA transcripts, the method of detecting a disease also can comprise testing for the expression of a BORIS polypeptide comprising the amino acid sequence of SEQ ID NO: 43, or an mRNA transcript comprising the nucleotide sequence of SEQ ID NO: 44.

The method of the invention can be used to detect any disease characterized by or associated with abnormal BORIS expression including, but not limited, to the detection of cancer. As mentioned above, BORIS mRNA has been detected in several hundred cancer and tumor cell lines representing most of the major forms of cancer. Thus, the method of the invention can be used to detect any type of cancer. Such cancers include, but are not limited to, cancer of the oral cavity and pharynx, the digestive system (e.g., the esophagus, stomach, small intestine, colon, rectum, anus, liver, gall bladder, and pancreas), the respiratory system (e.g., the larynx, lung, and bronchus, including non-small cell lung carcinoma), bones and joints (e.g., bony metastases), soft tissue, the skin (e.g., melanoma), breast, the genital system (e.g., the uterine cervix, uterine corpus, ovary vulva, vagina, prostate, testis, and penis), the urinary system (e.g., the urinary bladder, kidney, renal pelvis, and ureter), the eye and orbit, the brain and nervous system (e.g., glioma), or the endocrine system (e.g., thyroid). The cancer also can be a lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like).

Furthermore, as demonstrated herein, not all cancers are associated with the expression of the same BORIS isoforms. Accordingly, by testing for the expression of one or more different BORIS isoforms, it is possible to generate a BORIS expression pattern that can be used to distinguish between different types of cancers, or to detect a specific type of cancer. Thus, the method of detecting a disease associated with abnormal BORIS expression preferably comprises a step of comparing the BORIS expression of the mammal to a control, which comparison can be used, for example, to classify the type of disease with which the mammal might be afflicted. Any suitable control can be used for this purpose. Typically, the control can be provided by a BORIS expression pattern corresponding to a particular type of disease or cancer (e.g., the BORIS expression pattern of a mammal known to be afflicted with a particular type of disease or cancer).

Testing for the expression of one or more BORIS isoforms or BORIS isoform mRNA transcripts can be performed using any suitable technique. Typically, a sample of the tissue or body fluid of the mammal that does not express the BORIS gene (i.e., does not express the BORIS polypeptide or any isoform thereof) in the absence of disease is obtained, and the sample is tested for the expression of a BORIS isoform or BORIS isoform mRNA transcript. The BORIS gene is normally expressed only in the testes and ovaries. Accordingly, a sample of any tissue or body fluid other than a testicular or ovarian tissue sample can be used. The sample can be a solid sample or the sample can be fluid, such as a sample of body fluid. For instance, a section of whole tissue can be used for immunohistochemistry-based analysis, or can be homogenized to liquefy the components found in the tissue. The sample preferably is a fluid. Suitable fluid samples include, but are not limited to, blood, serum, plasma, lymph, and interstitial fluid.

Testing for the expression of one or more BORIS isoforms can comprise, for example, directly detecting one or more BORIS isoform polypeptides, or detecting one or more mRNA transcripts that encode a BORIS isoform polypeptide. Suitable methods of detecting protein levels in a sample include Western Blotting, radio-immunoassay, and Enzyme-Linked Immunosorbant Assay (ELISA). Such methods are described in Nakamura et al., Handbook of Experimental Immunology, 4th ed., Vol. 1, Chapter 27, Blackwell Scientific Publ., Oxford, 1987. When detecting proteins in a sample using an immunoassay, the sample is typically contacted with antibodies or antibody fragments (e.g., F(ab)2' fragments, single chain antibody variable region fragment (ScFv) chains, and the like) that specifically bind the target protein (e.g., BORIS isoform polypeptide). Thus, BORIS isoform polypeptides can be detected, for example, by contacting a sample of the tissue or body fluid of the mammal with an antibody or antibody fragment to the BORIS isoform, and detecting the binding of the antibody or antibody fragment with a BORIS isoform from the sample. Antibodies and other polypeptides suitable for detecting BORIS isoform polypeptides in conjunction with immunoassays are commercially available and/or can be prepared by routine methods, such as methods discussed elsewhere herein (e.g., Harlow et al., Antibodies: A Laboratory Manual, Cold Spring Harbor Publishers, Cold Spring Harbor, N.Y., 1988).

The immune complexes formed upon incubating the sample with the antibody are subsequently detected by any suitable method. In general, the detection of immune complexes is well-known in the art and can be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837, 3,850, 752, 3,939,350, 3,996,345, 4,277,437, 4,275,149 and 4,366, 241.

For example, the antibody used to form the immune complexes can, itself, be linked to a detectable label, thereby allowing the presence of or the amount of the primary immune complexes to be determined. Alternatively, the first added component that becomes bound within the primary immune complexes can be detected by means of a second binding ligand that has binding affinity for the first antibody. In these cases, the second binding ligand is, itself, often an antibody, which can be termed a "secondary" antibody. The primary immune complexes are contacted with the labeled, secondary binding ligand, or antibody, under conditions effective and for a period of time sufficient to allow the formation of secondary immune complexes. The secondary immune complexes are then washed to remove any nonspecifically bound labeled secondary antibodies or ligands, and the remaining label in the secondary immune complexes is then detected.

Other methods include the detection of primary immune complexes by a two-step approach. A second binding ligand, such as an antibody, that has binding affinity for the first antibody can be used to form secondary immune complexes, as described above. After washing, the secondary immune complexes can be contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. A number of other assays are contemplated; however, the invention is not limited as to which method is used.

Similarly, mRNA transcripts encoding a BORIS isoform can be detected by any suitable technique. Typically, a sample of the tissue or body fluid of the mammal (e.g., the RNA material of such a sample) is contacted with a nucleic acid probe that binds to an mRNA transcript encoding a BORIS isoform, and the binding of the nucleic acid probe with a BORIS isoform from the sample is detected. Suitable methods of detecting or measuring mRNA include, for example, Northern Blotting, reverse-transcription PCR(RT-PCR), and real-time RT-PCR. Such methods are described in Sambrook et al., *Molecular Cloning: A Laboratory Manual,* 2nd Ed., Cold Spring Harbor Press, Cold Spring Harbor, N.Y. 1989. Of these methods, real-time RT-PCR is typically preferred. In real-time RT-PCR, which is described in Bustin, J. Mol. Endocrinology. 25: 169-193 (2000), PCRs are carried out in the presence of a labeled (e.g., fluorogenic) oligonucleotide probe that hybridizes to the amplicons. The probes can be double-labeled, for example, with a reporter fluorochrome and a quencher fluorochrome. When the probe anneals to the complementary sequence of the amplicon during PCR, the Taq polymerase, which possesses 5' nuclease activity, cleaves the probe such that the quencher fluorochrome is displaced from the reporter fluorochrome, thereby allowing the latter to emit fluorescence. The resulting increase in emission, which is directly proportional to the level of amplicons, is monitored by a spectrophotometer. The cycle of amplification at which a particular level of fluorescence is detected by the spectrophotometer is called the threshold cycle, CT. This value is used to compare levels of amplicons. Probes suitable for detecting mRNA levels of the biomarkers are commercially available and/or can be prepared by routine methods, such as methods discussed elsewhere herein. Specific protocols for these and other methods of detecting polypeptides and mRNA transcripts in samples of mammalian tissues and body fluids are well known in the art (see, e.g., Sambrook et al., supra).

Alternatively, the expression of BORIS isoforms can be tested indirectly by detecting the presence of auto-antibodies to the BORIS isoforms in the mammal. Without wishing to be bound to any particular theory, it is believed that the abnormal expression of BORIS isoforms in tissues and body fluids where BORIS isoforms are not normally found (e.g., other than the testes or ovaries) causes the immune system of the mammal to produce antibodies to the BORIS isoforms that can be detected in a sample (e.g., the tissues, sera, or bloodstream) obtained from the diseased mammal. In the absence of such a disease, the BORIS isoforms are confined to the tissues and organs in which they are normally found in a non-diseased mammal, and the immune system of the mammal does not produce antibodies against the BORIS isoforms. Thus, a sample taken from a non-diseased mammal (e.g., a mammal without a disease characterized by abnormal BORIS expression) will not contain anti-BORIS isoform antibodies. Accordingly, by detecting the presence or absence of anti-BORIS isoform antibodies in the sample of a mammal, the method of the invention enables a determination as to whether the mammal has a disease characterized by abnormal BORIS expression, such as cancer.

Any suitable method of detecting anti-BORIS auto-antibodies in a sample can be used. Auto-antibodies to the BORIS isoforms can be detected, for instance, by contacting a sample of tissue or body fluid of the mammal with one or more BORIS isoforms or immunogenic portions thereof (e.g., one or more isolated or purified polypeptides comprising an immunogenic portion of the amino acid sequence of any of SEQ ID NOs: 25-42). The sample can be contacted with a BORIS polypeptide using any suitable method known in the art. Preferably, the sample is contacted with a BORIS polypeptide in vitro or ex vivo. In vitro and ex vivo methods for detecting antibodies in a sample are well known in the art and include, for example, enzyme-linked immunosorbent assay (ELISA), affinity chromatography, and radioimmunoassay (RIA).

By "immunogenic" or "immunoreactive" portion of a BORIS isoform is meant any portion of the full-length BORIS isoform (e.g., SEQ ID NOs: 25-42) that can generate an immune response in a mammal in vivo, bind to an anti-BORIS antibody or autoantibody in vivo or in vitro, or comprises one or more epitopes of a BORIS isoform. As used herein, the term "portion" is synonymous with the term "fragment," both of which are used to refer to contiguous part of a polypeptide comprising about 5 or more amino acids, such as about 10 or more, about 15 or more, about 20 or more, about 25 or more, or even about 30 or more amino acids). Of course, a full length BORIS isoform can provide the immunogenic portion; however, it can be more convenient to use a shorter portion of a BORIS isoform. One can determine whether any given portion of a BORIS isoform is immunogenic using routine techniques in view of the disclosures provided herein. For example, anti-BORIS antibodies to a BORIS isoform can be obtained from a mammal by introducing the BORIS isoform, or portion thereof, into the mammal and subsequently harvesting antibodies from the mammal using routine techniques. The given "test" portion of the BORIS isoform can be contacted with the anti-BORIS antibodies, and the binding affinity of the antibody to the portion of the BORIS isoform can be measured to determine whether the anti-BORIS antibodies bind to the given "test" portion of the BORIS isoform. If the antibodies bind to the test portion of the BORIS isoform, the test portion of the BORIS isoform is considered immunogenic. Other methods of determining whether a given portion of a BORIS isoform is immunogenic are available.

Suitable immunogenic portions of a BORIS isoform include the amino-terminal portion of a BORIS isoform (the "N-terminal domain"), defined as the region extending from the amino-terminal up to the zinc finger domain, or at least some portion thereof comprising about 100 or more amino acids (e.g., 200 or more, 250 or more, 300 or more, 400 or more, or 500 or more amino acids). Another suitable portion of a BORIS isoform polypeptide includes the carboxyl-terminal portion (the "C-terminal domain"), defined as the region starting after the zinc-finger domain and terminating at the carboxyl-terminus of BORIS, or at least some portion thereof comprising about 75 or more amino acids (e.g., about 100 or more, about 200 or more, about 300 or more, or about 400 or more amino acids).

The immunogenic portion of the BORIS isoform can be part of a larger polypeptide construct that comprises an amino acid sequence that is different from that of the native BORIS isoform. For instance, the immunogenic portion of a BORIS isoform can be part of a polypeptide construct comprising one or more different immunogenic portions of one or more different BORIS isoforms linked together, for example, by non-native amino acid sequences. Such a polypeptide construct might comprise, for instance, at least a portion of each of the N-terminal domain and the C-terminal domain of one or more different BORIS isoforms, as described herein. More preferably, the BORIS polypeptide construct comprises the entire N-terminal domain and C-terminal domain of one or more BORIS isoforms. It is further preferred that the BORIS polypeptide construct excludes any zinc finger domain of the BORIS isoform.

Even smaller portions of a BORIS isoform can provide an immunogenic portion, provided that a BORIS isoform epitope is present in the portion or fragment. By "epitope" is meant a sequence on an antigen that is recognized by an antibody or an antigen receptor. Epitopes also are referred to in the art as "antigenic determinants." An immunogenic portion of the BORIS isoform can be less than about 660, 200, 150, 100, 60, 50, 30, 20, 15, or 12 amino acid residues in length, so long as it can be bound by an anti-BORIS antibody. The immunogenic portion of the BORIS isoform preferably comprises at least about 10, 11, or 12 amino acids; however, immunogenic portions of a BORIS isoform comprising fewer than 11 amino acids (e.g., about 4, 6, 8, or 10 or more amino acids) also are within the scope of the invention. Of course, the preferred number of amino acids also can be expressed in terms of ranges within any of the above-described preferred limits (e.g., 10-200 amino acids, 10-100 amino acids, 10-50 amino acids, 10-20 amino acids, etc.).

An immunogenic portion of a BORIS isoform also can be provided by a variant of the amino acid sequence of a BORIS isoform. As used herein, the term "variant" is used to refer to a sequence that is altered in the specific amino acid or nucleotide sequence, but retains the required function of the native sequence. With respect to the immunogenic portion of a BORIS isoform, a variant of the BORIS isoform retains the function of binding to an antibody to the BORIS isoform. BORIS isoform variants can be generated and characterized for their ability to bind with an anti-BORIS antibody or a functional fragment thereof (e.g., a Fab or F'(ab)$_2$) using the information provided herein. For example, BORIS isoform variants can be generated using, for example, site-directed or random mutagenesis of a nucleic acid sequence encoding a BORIS isoform, as provided herein. The binding characteristics of the BORIS variant thus produced can be determined, for example, by measuring the binding affinity of antibodies to a BORIS isoform to the variant. Such antibodies can be obtained, for instance, from the serum of a mammal inoculated with a native BORIS isoform, or from the serum of a mammal with cancer.

A variant of a BORIS isoform desirably shares one or more regions of amino acid sequence identity with a native BORIS isoform. In this regard, the variant preferably comprises an amino acid sequence that is at least about 50% identical (e.g., at least about 60%, at least about 70%, at least about 80%, or at least about 90% identical) to the amino acid sequence of a native BORIS isoform. More preferably, the variant comprises an amino acid sequence that is at least about 75% identical (e.g., at least about 85%, or at least about 95% identical) to an amino acid sequence of a native BORIS isoform. Most preferably, the polypeptide comprises an amino acid sequence that is at least about 90% identical (e.g., at least about 95%, at least about 97%, or at least about 99% identical) to an amino acid sequence of a native BORIS isoform. As used herein, sequence identity is as determined using the well-known BLAST algorithms (e.g., BLASTp, BLAST 2.1, BL2SEQ, and later versions thereof)). Variants of a BORIS isoform capable of binding to anti-BORIS antibodies preferably have at least 5, 6, or 7 amino acid residues that are identical to the amino acid sequence of a native BORIS isoform over a window of eight amino acid residues.

Any immunogenic portion of a BORIS isoform can be used alone or in conjunction with other immunogenic portions of the same or different BORIS isoforms. The immunogenic portion of a BORIS isoform, whether used alone or in conjunction with other immunogenic portions of a BORIS isoform, also can be part of a larger polypeptide (e.g., inserted into (or otherwise attached to) another (i.e., "non-BORIS") protein). Without intending to be bound by any particular theory, it is believed that different individuals will have immunogenic responses to BORIS isoforms based on the MHC molecules expressed on their antigen presenting cells (e.g., macrophages). Accordingly, the portion of BORIS isoforms that is immunogenic can vary from individual to individual. Moreover, an autoreactive antibody response directed against both the N-terminal and C-terminal domains of BORIS isoforms has been detected in some cancer patients. Thus, it is preferably the use of more than one immunogenic portion of the BORIS isoforms (e.g., more than one BORIS isoform epitope). When more than one immunogenic portion is used, the different immunogenic portions can be provided, for example, by several discontiguous polypeptides used simultaneously (e.g., two or more polypeptides each comprising a different immunogenic portion of a BORIS isoform) or by a single polypeptide comprising two or more different immunogenic portions of BORIS (e.g., linked by a non-native linker sequence).

In a preferred embodiment of the invention, two or more immunogenic portions of one or more BORIS isoforms are linked by a flexible linker amino acid sequence. Such a construct also can comprise an immunogenic portion of the BORIS polypeptide. Flexible linkers are used in the art to join two distinct polypeptides, such as, for example, in the construction of fusion or chimeric proteins. Thus, for example, an N-terminal domain portion and a C-terminal domain portion of one or more BORIS isoforms can be linked via a flexible linker sequence to form a single polypeptide molecule. The flexible linker can be any suitable amino acid sequence that can be used to join to separate polypeptide domains. In this regard, the flexible linker preferably comprises about 5 or more amino acids (e.g., about 6 or more, 7 or more, or 9 or more amino acids), more preferably about 10 or more amino acids (e.g., about 11 or more, 12 or more, or 14 or more amino acids), and most preferably about 15 or more amino acids (e.g., about 17 or more, 20 or more, or 25 or more amino acids). Linker sequences as well as methods for joining polypeptide domains using flexible linkers are known in the art (see, e.g., Imanishi et al., *Biochem. Biophys. Res. Commun.*, 333(1), 167-73 (2005); Lin et al., *Eur. Cytokine Netw.*, 15(3), 240-6 (2004)).

The BORIS isoforms or immunogenic portions thereof can be joined to other biomolecules, such as, for example, proteins, polypeptides, lipids, carbohydrates, prenyl, and acyl moieties, and nucleic acids. For instance, the BORIS isoforms or immunogenic portions thereof can be attached to a signaling moiety (also known as a detectable label). The identity and use of signaling moieties is well-known in the art. A signaling moiety is a molecule capable of indicating the presence of an analyte or reagent in a sample, usually after manipulation of the sample. Such manipulations often include incubating a sample and appropriate detection reagents under conditions allowing two moieties to bind together, if present, and then removing any of the labeled moiety from the sample via washing, filtration, or other suitable techniques. Other methods of working with signaling moieties are well-known in the art. Suitable signaling moieties include, but are not limited to, fluorescent molecules (e.g., green fluorescent protein), fluorescent quenchers, epitopes and haptens for antibodies that do not recognize BORIS (e.g., the well-known FLAG epitope), enzymes (e.g., chromogenic or luminescent (such as horse radish peroxidase or β-galactosidase)), a nucleic acid that can be amplified or specifically hybridized to a probe, biotin, avidin or streptavidin, lectins and colloids. Methods for linking proteins with detectable labels and solid supports are well-known in the art.

The antibody or autoantibody detected in accordance with a method of the invention preferably binds with greater affinity to BORIS or a BORIS isoform than to CCCTC-binding-factor (CTCF), or the antibody or autoantibody does not bind CTCF at all. Thus, the method of the invention preferably comprises detecting an anti-BORIS isoform antibody or autoantibody with a binding affinity for BORIS or a BORIS isoform that is greater than its binding affinity for CTCF. This is particularly advantageous where the portion of BORIS used comprises the zinc-finger domain of BORIS. More preferably, the dissociation constant ($K_d$) of binding under standard conditions between the antibody detected by the method of the invention and BORIS is at least 10-fold less, more preferably at least 100-fold less, or even 1000-fold less than the $K_d$ of binding between the same antibody and CTCF. In some embodiments, binding of antibodies in a patient's serum to CTCF can be used as a negative control. When antibodies or autoantibodies to a particular BORIS isoform are desired, the method preferably comprises detecting such an antibody or autoantibody with a greater binding affinity for the desired target BORIS isoform than for other BORIS isoforms.

In a preferred embodiment, the method of detecting cancer or method of detecting anti-BORIS antibodies includes determining the class and/or subclass of the antibodies present in the patient's body, or sample derived therefrom, that are reactive with BORIS. One of ordinary skill in the art will appreciate that the five major human immunoglobulin classes (or "isotypes") are immunoglobulin M (i.e., IgM), IgD, IgG, IgA, and IgE, which are typically defined by the structure of the constant regions of the antibody heavy chain. The light chain of a human antibody molecule is typically classified in the art as either a lambda (λ) chain or a kappa (κ) chain. IgG antibodies can be subdivided further into four subtypes (i.e., IgG1, IgG2, IgG3, and IgG4), whereas IgA antibodies typically are subdivided into two subtypes (i.e., IgA1 and IgA2). It is well-known in the art how to determine the class and subclass of isolated or purified antibodies. For example, BORIS-reactive antibodies can be isolated from a human's serum by immunochromatography. Wells of microtiter plates can be coated with 10 µg/ml of anti-human immunoglobin overnight at 4° C. After blocking with 5% BSA, the plates are reacted with 10 µg/ml of a monoclonal antibody or purified isotype controls, at ambient temperature for two hours. The wells can then be reacted with human IgG1-specific, IgG2-specific, IgG3-specific or IgG4-specific or human IgM-specific alkaline phosphatase-conjugated probes. After washing, the plates can be developed with a luminogenic or chromogenic substrate and analyzed for light or color development.

The methods of detecting a disease and detecting abnormal BORIS expression can be used in different ways. For example, the method can be used simply to establish the existence of a disease state for the purposes of diagnosis or screening. In addition, the method can be used, for example, to monitor the status (e.g., progression or regression) of a disease state, such as by comparing the level of anti-BORIS antibodies (or BORIS expression levels) from different samples over time. Such a use would be helpful in monitoring the response of patients to a particular therapeutic regimen.

In a related aspect, the invention also provides a method of detecting abnormal BORIS expression for purposes other than the detection of disease. The detection of abnormal BORIS expression can be used for any suitable purpose, such as for prognosticating, monitoring, or researching diseases characterized by abnormal gene expression, especially abnormal BORIS expression, including without limitation hyperproliferative diseases such as cancer. For instance, the methods of detecting abnormal BORIS expression is can be used to monitor the effect of drugs and other therapies on various diseases, especially various cancers described herein, in connection with the development of new or existing drugs or therapies, or as part of an established therapy regimen. Also, the methods of detecting abnormal BORIS expression can be used to generate BORIS expression profiles, which, in turn, can be used in accordance with methods of screening for, detecting, diagnosing, prognosticating, monitoring, or researching disease. The method of detecting abnormal BORIS expression can comprise testing for the expression of one or more BORIS isoforms comprising an amino acid sequence selected from the group consisting of SEQ ID NOs: 25-42, or testing for the expression of one or more BORIS isoform mRNA transcripts comprising a nucleotide sequence selected from the group consisting of SEQ ID NOs: 1-24, in the tissue of a mammal that does not express the BORIS isoform in the absence of a disease. All other aspects of the method of detecting abnormal BORIS expression are as described with respect to the method of detecting a disease associated with abnormal BORIS expression.

The mammal used in conjunction with the methods described herein can be any suitable mammal, such as dogs, cats, cows, goats, pigs, mice, rats, guinea pigs, rabbits, gerbils, monkeys, and hamsters. The mammal preferably is a human.

Isolated or Purified Polypeptide, Nucleic Acid, Antibody, Cell, and Composition

The invention provides an isolated or purified polypeptide comprising, consisting essentially of, or consisting of an amino acid sequence selected from the group consisting of SEQ ID NOs: 25-42, or an immunogenic portion thereof. The immunogenic portion of a BORIS isoform can comprise, consist essentially of, or consist of any of those immunogenic portions described herein as useful in conjunction with the method of detecting a disease or method of detecting an anti-BORIS autoantibody. The term "consisting essentially of" is used herein to mean that the polypeptide cannot comprise any other biologically active amino acid sequence, but can contain other non-biologically active sequences or other components such as regulatory or signal sequences, reporter constructs, linker molecules, targeting or delivery components, and the like.

If desired, the isolated or purified polypeptide can be modified, for instance, by glycosylation, amidation, carboxylation, or phosphorylation, or by the creation of acid addition salts, amides, esters, in particular C-terminal esters, and N-acyl derivatives of the polypeptide molecules of the invention. The polypeptide molecules also can be dimerized or polymerized. Moreover, the polypeptide molecules can be modified to create polypeptide derivatives by forming covalent or non-covalent complexes with other moieties in accordance with methods known in the art. Covalently-bound complexes can be prepared by linking the chemical moieties to functional groups on the side chains of amino acids comprising the polypeptides, or at the N- or C-terminus.

The isolated or purified polypeptide can be manufactured using any suitable method. In this regard, nucleic acid sequences encoding BORIS isoforms or immunogenic portions thereof can be synthetically produced using, for example, the nucleic acid sequences provided herein, and expressed in an appropriate host cell, thereby resulting in production of a BORIS isoform or immunogenic portion thereof. Alternatively, BORIS isoforms and immunogenic portions thereof can be synthesized using, for example, the amino acid sequences disclosed herein and protein synthesis methods known in the art. Alternatively, BORIS isoforms can be isolated from a mammal, and, as desired, immunogenic portions thereof can be generated using proteases that cleave within the full-length BORIS isoforms. As discussed above, BORIS isoforms or immunogenic portions thereof can be labeled with a signaling moiety or detectable label, or linked to a solid support.

The invention also provides an isolated or purified nucleic acid comprising, consisting essentially of or consisting of a nucleic acid sequence encoding an amino acid sequence selected from the group consisting of SEQ ID NOs: 25-42, or an immunogenic portion thereof, as well as an isolated or purified nucleic acid comprising, consisting essentially of, or consisting of a nucleotide selected from the group consisting of SEQ ID NOs: 1-24. The term "consisting essentially of" is used herein to mean that the nucleic acid cannot comprise any other sequence that codes for a biologically active protein, but can contain other nucleic acid sequences or other components such as regulatory sequences, reporter constructs, linker molecules, and the like.

The present invention also provides a vector comprising an above-described isolated or purified nucleic acid molecule. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)).

Suitable vectors include those designed for propagation and expansion or for expression or both. Examples of suitable vectors include plasmids, phagemids, cosmids, viruses, and other vehicles derived from viral or bacterial sources. Preferably, the vector is a viral vector and is selected from the group consisting of an adenovirus, adeno-associated virus, retroviruses, SV40-type viruses, polyoma viruses, Epstein Barr viruses, papillomaviruses, herpes virus, vaccinia virus and polio virus. Most preferably, the vector is an adenoviral vector.

When an adenoviral vector is used in the context of the present invention, the adenoviral vector can be derived from any serotype of adenovirus. Adenoviral stocks that can be employed as a source of adenovirus can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. Preferably, however, an adenovirus is of serotype 2, 5 or 9. However, non-group C adenoviruses can be used to prepare adenoviral vectors for delivery of one or more non-native nucleic acid sequences to a desired tissue. Preferred adenoviruses used in the construction of non-group C adenoviral vectors include Ad12 (group A), Ad7 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030; 5,837,511; and 5,849,561 and International Patent Applications WO 97/12986 and WO 98/53087.

In preferred embodiments, the adenoviral vector of the present invention is deficient in one or more replication-essential gene functions. Regions contained within the adenoviral genome which are essential for replication include E1a, E1b, E2, E4, and L1-L5. By "deficient" is meant a disruption contained within at least one of the above-mentioned regions such that the gene product encoded by the region is produced in a reduced amount as compared to normal levels. Suitable disruptions include point mutations, substitutions, deletions, insertions, and inversions. Typically, the adenoviral vector is deficient in one or more replication-essential gene functions of the E1a, E1b, E3 and/or E4 region.

A nucleic acid sequence encoding a marker protein, such as green fluorescent protein or luciferase also can be present in the vector. Such marker proteins are useful in vector construction and determining vector migration. Marker proteins also can be used to determine points of injection in order to efficiently space injections of a vector composition to provide a widespread area of treatment, if desired. Alternatively, a nucleic acid sequence encoding a selection factor, which also is useful in vector construction protocols, can be part of the adenoviral vector.

Negative selection genes may be incorporated into any of the above-described vectors. A preferred embodiment is an HSV tk gene cassette (Zjilstra et al., *Nature*, 342: 435 (1989); Mansour et al., *Nature*, 336: 348 (1988); Johnson et al., *Science*, 245: 1234 (1989): Adair et al., *PNAS*, 86: 4574 (1989); Capecchi, M., *Science*, 244: 1288 (1989), incorporated herein by reference) operably linked to a viral promoter in a viral vector. The tk expression cassette (or other negative selection expression cassette) is inserted into the viral genome, for example, as a replacement for a substantial deletion of a non-essential viral gene. Other negative selection genes will be apparent to those of skill in the art.

The vector of the present invention can comprise a native or non-native regulatory sequence operably linked to an isolated or purified nucleic acid molecule as described above. If more than one nucleotide sequence is included in the nucleic acid molecule, each sequence can be operably linked to its own regulatory sequence. The "regulatory sequence" is typically a promoter sequence or promoter-enhancer combination, which facilitates the efficient transcription and translation of the nucleic acid to which it is operably linked. The regulatory sequence can, for example, be a mammalian or viral promoter, such as a constitutive or inducible promoter. Exemplary viral promoters which function constitutively in eukaryotic cells include, for example, promoters from the simian virus, papilloma virus, adenovirus, human immunodeficiency virus, Rous sarcoma virus, cytomegalovirus, Moloney leukemia virus and other retroviruses, and Herpes simplex virus. Other constitutive promoters are known to those of ordinary skill in the art. The promoters useful as regulatory sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art and can be used in the context of the invention, when desired. The selection of promoters, e.g., strong, weak, inducible, tissue-specific and developmental-specific, is within the skill in the art. Similarly, the combining of a nucleic acid molecule as described above with a promoter is also within the skill in the art.

The term "operably linked" as used herein can be defined when a nucleic acid molecule and the regulatory sequence are covalently linked in such a way as to place the expression of the nucleotide coding sequence under the influence or control of the regulatory sequence. Thus, a regulatory sequence would be operably linked to a nucleic acid molecule if the regulatory sequence were capable of effecting transcription of that nucleic acid molecule such that the resulting transcript is translated into the desired protein or polypeptide.

The present invention further provides a cell (i.e., a host cell) comprising an isolated or purified nucleic acid molecule or a vector as described above, preferably a cell that expresses a BORIS isoform or immunogenic portion thereof, as described herein. Examples of host cells include, but are not limited to, a prokaryotic or eurkaryotic host cell. Prokaryotic cells include those derived from *E. coli, B. subtilis, P. aerugenosa, S. cerevisiae*, and *N. crassa*. Preferably, the host cell is derived from a mammal, such as a human.

An antibody (polyclonal or monoclonal) to a BORIS isoform or immunogenic portion thereof also is contemplated as part of the invention, as well as a cell line that produces a monoclonal antibody to a BORIS isoform or immunogenic portion. Such "hybridoma cell lines" desirably produce a monoclonal antibody that is specific for a BORIS isoform. Methods of making polyclonal antibodies and hybridomas are known in the art (see, e.g., Roitt I., *Immunology*, 4$^{th}$ Ed., Mosby, N.Y. (1996)). Typically, the antibody will be specific for a region of a BORIS isoform or a region of an immunogenic portion of a BORIS isoform. Typically, the region will be the N- or C-terminal portion of the BORIS isoform. Alternatively, the antibody can be specific for a zinc finger region of a BORIS isoform. Such an antibody will have a greater affinity for zinc finger regions of a BORIS isoform as compared to other proteins containing similar zinc finger regions (e.g., CTCF); thus being able to distinguish between the two molecules. Antibodies of the invention can be employed for both diagnostic and therapeutic applications as they are described herein.

The invention further provides a composition comprising an isolated or purified polypeptide, nucleic acid, or antibody as described herein and a carrier, preferably a pharmaceutically acceptable carrier. The phrase "pharmaceutically acceptable carrier," as used herein, refers to a carrier that does not interfere with the effectiveness of the biological activity of the active ingredients and which is not toxic to the host or patient. The pharmaceutical compositions of the present invention can be in a variety of forms. These include, for example, solid, semi-solid and liquid dosage forms, such as tablets, pills, powders, liquid solutions or suspensions, liposomes, injectable and infusible solutions. Inhalable preparations, such as aerosols, are also included. Preferred formulations are those directed to oral, intranasal and parenteral applications, but it will be appreciated that the preferred farm will depend on the particular diagnostic or therapeutic application. The methods for the formulation and preparation of pharmaceutical compositions are well known in the art and are described in, for example, *Remington's Pharmaceutical Sciences*, Mack Publishing Company, Philadelphia, Pa., 17th ed. (1985), The Merck Index, 11th ed., (Merck & Co. 1989), and Langer, *Science*, 249, 1527-1533 (1990).

The composition can comprise more than one active ingredient. Alternatively, or additionally, the composition can comprise another pharmaceutically active agent or drug. For example, when treating cancer, other anticancer compounds can be used in conjunction with the composition of the present invention and include, but are not limited to, all of the known anticancer compounds approved for marketing in the United States and those that will become approved in the future. See, for example, Table 1 and Table 2 of Boyd, *Current Therapy in Oncology*, Section 1. Introduction to Cancer Therapy (J. E. Niederhuber, ed.), Chapter 2, by B.C. Decker, Inc., Philadelphia, 1993, pp. 11-22. More particularly, these other anticancer compounds include doxorubicin, bleomycin, vincristine, vinblastine, VP-16, VW-26, cisplatin, carboplatin, procarbazine, and taxol for solid tumors in general; alkylating agents, such as BCNU, CCNU, methyl-CCNU and DTIC, for brain or kidney cancers; and antimetabolites, such as 5-FU and methotrexate, for colon cancer.

The compounds and compositions described herein can be used for any purpose. In addition to being useful in the method of detecting a disease and method of detecting abnormal BORIS expression, the compounds and compositions described herein can be used for other purposes, such as for inducing an immune response in a mammal. Such immune responses have multiple uses. For example, antibodies and other immunity-related molecules specific for BORIS can be isolated and used for research, control reagents useful in a method for detecting BORIS expression in a mammal, and as a method for destroying cancer cells that are present or could arise in a mammal. In this regard, the invention provides, as a related aspect, a method of inducing an immune response in a mammal comprising administering to a mammal a BORIS polypeptide as defined herein. Suitable methods of administration are known in the art. All other aspects of the method of inducing an immune response are as previously described herein.

Method of Treating a Disease Associated with Abnormal BORIS Expression

The invention provides a method of treating or preventing a disease associated with abnormal BORIS expression in a mammal comprising administering to a mammal that exhibits abnormal BORIS expression an inhibitor of a BORIS isoform. The inhibitor of the BORIS isoform can be any compound and/or molecule or any other agent capable of inhibiting the normal function of the BORIS isoform, or capable of inhibiting the expression of the BORIS isoform at the DNA or RNA level. Typically, the inhibitor of BORIS is a small molecule, an antibody, an antisense molecule, or a ribozyme molecule. It is also conceivable to provide an inhibitor of a BORIS isoform that comprises a molecule (e.g., a zinc finger binding protein) that recognizes zinc finger binding domains specific for a BORIS isoform and can therefore initiate its inhibition. It will be understood that when such zinc finger binding proteins are used, these molecules will be employed to specifically recognize zinc finger binding domains of a BORIS isoform as compared to other proteins comprising similar zinc finger binding domains (e.g., CTCF), such that the normal function of these similar proteins is not inhibited. Methods of identifying these inhibitors are well known in the art and can be accomplished without any undue experimentation using a variety of in vitro assays.

By "treating" is meant the amelioration of a pathologic state of any symptom thereof, in whole or in part. By "preventing" is meant the protection, in whole or in part, against a particular pathologic state, including, but not limited to, the prevention of the onset of any one or more symptoms of a pathologic state. One of ordinary skill in the art will appreciate that any degree of protection from, or amelioration of, a pathologic state is beneficial to a mammal.

According to a preferred aspect of the invention, the method of treating or preventing a disease associated with abnormal BORIS expression in a mammal comprises administering a short interfering RNA (siRNA) molecule to a mammal afflicted with a disease associated with abnormal BORIS expression, wherein the siRNA molecule comprises a sequence of at least about 10 contiguous nucleotides, preferably at least about 15 nucleotides, or even at least about 20 nucleotides (typically 21 nucleotides) that is complimentary to a portion or fragment of a BORIS isoform mRNA transcript (e.g., an mRNA transcript comprising a nucleotide sequence selected from the group consisting of SEQ ID NOs: 1-24). Methods of designing siRNA molecules are known in the art. Typically, the siRNA will have a 3' dinucleotide overhang (preferably UU residues). Accordingly, the target site generally will be chosen to be a site with an appropriate dinucleotide at the start position, such as an "AA" dinucleotide along with the appropriate number of 3' nucleotides. The siRNA, of course, will have the complimentary sequence.

According to another preferred aspect of the invention, method of treating or preventing a disease associated with abnormal BORIS expression in a mammal comprises administering an anti-BORIS isoform antibody to a mammal afflicted with a disease associated with abnormal BORIS expression, wherein the anti-BORIS isoform antibody selectively binds to a BORIS isoform polypeptide (e.g., a BORIS isoform polypeptide comprising an amino acid sequence selected from the group consisting of SEQ ID NOs: 25-42). Suitable anti-BORIS isoform antibodies, including BORIS isoform-specific antibodies, can be generated given the information provided herein and routine techniques, as previously described.

Suitably, the inhibitor will be administered as part of a composition comprising a carrier. Suitable carriers and routes of administration are as described with respect to the other aspects of the invention.

Kit and Array Useful for Detecting BORIS Expression

The invention provides a kit useful for detecting BORIS expression comprising (a) a probe set comprising one or more probes that bind to (i) a BORIS isoform polypeptide comprising an amino acid sequence selected from the group consisting of SEQ ID NOs: 25-42, (ii) an auto-antibody to a BORIS isoform polypeptide comprising an amino acid sequence selected from the group consisting of SEQ ID NOs: 25-42, or (iii) a BORIS isoform mRNA transcript comprising a nucleic acid sequence selected from the group consisting of SEQ ID NOs: 1-24, and (b) a reagent that facilitates the detection of the probe.

The probe set can comprise one or more one or more antibodies, one or more polypeptides, or one or more nucleic acids (i.e., polynucleotides) depending upon whether the target to be detected in the sample is a BORIS isoform (in which can an antibody probe is useful), an auto-antibody to BORIS (in which case a polypeptide probe is useful), or a BORIS isoform mRNA transcript (in which case a nucleic acid probe is useful). Probes that specifically bind the respective target molecules can be designed using routine techniques. The probe specifically binds a target BORIS isoform polypeptide, auto-antibody, or mRNA transcript with preference over other molecules in the sample, such that the probe can be used to differentiate between the target molecule and the other molecules in the sample.

Polynucleotide and polypeptide probes can be generated by any suitable method known in the art (see, e.g., Sambrook et al., supra). For example, polynucleotide probes that specifically bind to BORIS isoform mRNA transcripts can be created using the nucleic acid sequences of BORIS isoform mRNA transcripts themselves (as disclosed herein) by routine techniques (e.g., PCR or synthesis). By way of further illustration, a polynucleotide probe that binds to the mRNA transcript of a particular BORIS isoform can be provided by a polynucleotide comprising a nucleic acid sequence that is complementary to the mRNA sequence or a fragment thereof, or sufficiently complementary to the sequence or fragment thereof that it will selectively bind to the sequence (e.g., bind to the target mRNA transcript with greater affinity than to other mRNA transcripts in the sample). The exact nature of the polynucleotide probe is not critical to the invention; any probe that will selectively bind the mRNA target can be used. Typically, the polynucleotide probes will comprise about 10 or more nucleic acids (e.g., about 20 or more, 50 or more, or 100 or more nucleic acids). Generally, the probe will contain fewer than 50 nucleotides. Thus, for example, the polynucleotide probe can comprise, consist essentially of, or consist of a fragment of any of SEQ ID NOs: 1-24 or complement thereof. In order to confer sufficient specificity, the nucleic acid probe will have a sequence identity to a compliment of the target sequence of about 90% or more, preferably about 95% or more (e.g., about 98% or more or about 99% or more) as determined, for example, using the well-known Basic Local Alignment Search Tool (BLAST) algorithm (available through the National Center for Biotechnology Information (NCBI), Bethesda, Md.). More preferably, the probe will comprise no more than one or two base-pair mismatches with the target sequence.

Similarly, polypeptide probes that bind to the BORIS isoform polypeptides described herein can be created using the amino acid sequences of the BORIS isoforms, disclosed herein, and routine techniques. For example, antibodies or antibody fragments to the BORIS isoforms can be generated in a mammal using routine techniques, which antibodies can be harvested to serve as probes for the BORIS isoforms. The exact nature of the polypeptide probe is not critical to the invention; any probe that will selectively bind to the BORIS isoform target can be used. Preferred polypeptide probes include antibodies and antibody fragments antibodies or antibody fragments (e.g., F(ab)$_2$' fragments, single chain antibody variable region fragment (ScFv) chains, and the like). Antibodies suitable for detecting the biomarkers can be prepared by routine methods, and are commercially available. See, for instance, Harlow et al., *Antibodies: A Laboratory Manual*, Cold Spring Harbor Publishers, Cold Spring Harbor, N.Y., 1988.

The reagent that facilitates detection of the probe can be any suitable reagent known in the art. For example, the reagent can be a molecule or compound that can be used to label the probe or the target molecules in the sample before or after contacting the sample with the probe. Specific examples of such reagents include, without limitation, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The kit can further comprise one or more BORIS expression profiles (e.g., the expression profile of one or more BORIS isoforms) corresponding to one or more types of diseases or cancers. The BORIS expression profile for a given type of disease or cancer can be generated, for example, by testing for the expression of the BORIS isoforms and/or the BORIS polypeptide in a mammal or population of mammals known to be afflicted with the disease or cancer, or by testing for the expression of BORIS isoforms and/or the BORIS polypeptide in a cell line representative of a specific cell line. Preferably, the BORIS expression profile is generated from a mammal or, more preferably, a population of mammals known to be afflicted with a particular disease. The BORIS expression profile can serve as a reference by which to compare the BORIS expression of a given mammal of an unknown disease state in order to determine whether the mammal, in fact, has a disease or propensity to develop a disease.

Preferably, the BORIS expression profiles are provided in the form of a database comprising the BORIS expression profile of one or more different types of cancer or other diseases associated with abnormal BORIS expression, wherein the database facilitates the comparison of a BORIS expression profile of a patient with the BORIS expression profile of one or more different types of cancer. Such databases that facilitate the comparison of the BORIS expression profile of a patient with the BORIS expression profile of one or more different types of cancer or other diseases include, for example, searchable databases, especially searchable electronic databases.

The probes of the probe set can be immobilized on a suitable substrate, so as to provide an array. In this respect, the invention also provides an array useful for the detection of BORIS expression in a mammal, the array comprising one or more probes immobilized on a substrate, wherein the probes bind to (i) a BORIS isoform comprising an amino acid sequence selected from the group consisting of SEQ ID NOs: 25-42, (ii) an auto-antibody to a BORIS isoform comprising an amino acid sequence selected from the group consisting of SEQ ID NOs: 25-42, or (iii) a BORIS isoform mRNA transcript comprising a nucleotide sequence selected from the group consisting of SEQ ID NOs: 1-24.

The substrate can be any rigid or semi-rigid support to which polynucleotides or polypeptides can be covalently or non-covalently attached. Suitable substrates include membranes, filters, chips, slides, wafers, fibers, beads, gels, capillaries, plates, polymers, microparticles, and the like. Materials that are suitable for substrates include, for example, nylon, glass, ceramic, plastic, silica, aluminosilicates, borosilicates, metal oxides such as alumina and nickel oxide, various clays, nitrocellulose, and the like.

The polynucleotide or polypeptide probes can be attached to the substrate in a pre-determined 1- or 2-dimensional arrangement, such that the pattern of hybridization or binding to a probe is easily correlated with the expression of a particular BORIS isoform. Because the probes are located at specified locations on the substrate, the hybridization or binding patterns and intensities create a unique expression profile, which can be interpreted in terms of the expression of particular BORIS isoforms.

The array can comprise other elements common to polynucleotide and polypeptide arrays. For instance, the array also can include one or more elements that serve as a control, standard, or reference molecule, such as a housekeeping gene or portion thereof (e.g., PBGD, GAPDH), to assist in the normalization of expression levels or the determination of nucleic acid quality and binding characteristics, reagent quality and effectiveness, hybridization success, analysis thresholds and success, etc. These other common aspects of the arrays or the addressable elements, as well as methods for constructing and using arrays, including generating, labeling, and attaching suitable probes to the substrate, consistent with the invention are well-known in the art. Other aspects of the array are as previously described herein with respect to the methods of the invention.

The kit or array can comprise a single probe for a single BORIS isoform polypeptide, mRNA transcript, or autoantibody. However, the kit or array advantageously comprises more than one probe, such as two or more, three or more, four or more, five or more, 10 or more, 15 or more, or even 20 or more different probes that each bind to a different BORIS isoform polypeptide, mRNA transcript, or autoantibody (or even a different probe for each of the BORIS isoform polypeptides, mRNA transcripts, or autoantibodies identified herein).

The kit or array can further comprise probes for polypeptides, mRNA transcripts, or autoantibodies other than BORIS isoform polypeptides, mRNA transcripts or autoantibodies. For example, it is desirable for the kit or array to comprise a probe for a BORIS polypeptide comprising the amino acid sequence of SEQ ID NO: 43, the mRNA transcript encoding such a BORIS polypeptide (e.g., an mRNA transcript comprising the nucleic acid sequence of SEQ ID NO: 44), or an autoantibody to such a BORIS polypeptide. Other probes also can be included, such as probes that bind to other tumor antigens or other genetic cancer markers. Nevertheless, it may be convenient in some instances to limit the total number of different probes for ease of use. Thus, for instance, the kit or array can comprise less than about 1000 different probes, or less than about 500 different probes, such as less than about 100 different probes, or even less than about 50 different probes (e.g., less than about 30 different probes).

The following examples further illustrate the invention but, of course, should not be construed as in any way limiting its scope.

EXAMPLE 1

This example illustrates the identification of multiple BORIS isoforms in the human testes.

RT-PCR was used to identify and sequence the mRNA transcripts of 24 different mRNA splice variants of the BORIS gene expressed in the human testes. The 24 mRNA splice variants are depicted in Figures A, B, C, and D, which encode 18 different BORIS isoform polypeptides. The nucleotide sequences of the mRNA splice variants, as well as the amino acid sequences encoded by the mRNA splice variants, are set forth in Table 1.

EXAMPLE 2

This example illustrates the generation of isoform-specific anti-BORIS antibodies, and the use of such antibodies to identify BORIS isoforms in the human testes.

Isoform-specific anti-BORIS antibodies were generated to three different BORIS isoforms (SEQ ID NOs: 25, 27, and 32) by immunizing rabbits with synthetic peptides specific to each isoform. In particular, peptides CKYASVEVKPFLDLKLHGILVEAAVQVTPSVTNSRI (SEQ ID NO: 45) and CYKQAFYYSYKIYIGNNMHSLL (SEQ ID NO: 46) were used to develop antibodies to the isoform comprising SEQ ID NO: 25; peptides CLLGSSDSHASVSGAGITDARHHA (SEQ ID NO: 47) and CITDARHHAWLIVLLELVEMGFYHVSHS (SEQ ID NO: 48) were used to generate antibodies to the isoform comprising SEQ ID NO: 27; and peptides CPPGLHHPKAGLGPEDPLPGQLRHTAG (SEQ ID NO: 49) and GQLRHTTAGTGLSSLLQGPLC (SEQ ID NO: 50) were used to generate antibodies to the isoform comprising SEQ ID NO: 32. The rabbits were immunized with the peptides conjugated to keyhole limpet hemocyanin (KLH). Thereafter, peptide-specific antibodies were affinity purified on a column using the same peptides. The isoform-specific anti-BORIS antibodies were successfully used to detect the three different BORIS isoforms in the tissue of the human testes.

EXAMPLE 3

This example demonstrates the expression pattern of BORIS isoforms in the NCI-60 cell lines.

RT-PCR was used to test for the expression of six different BORIS isoforms in each of the NCI-60 cell lines. The NCI-60 cell line panel is considered to be representative of the vast majority of human cancer types. The results are presented in Table 1, wherein a "+" indicates positive expression, and a blank indicates no expression.

As illustrated by the results in Table 2, each of the NCI-60 cell lines showed expression of at least one isoform of BORIS. Moreover, different cancers exhibited different BORIS isoform expression patterns. These results show that BORIS isoform expression patterns can be used to differentiate between different types of cancers.

TABLE 1

| mRNA Splice Variant | Nucleotide Sequence | Amino Acid Sequence |
| --- | --- | --- |
| BORIS A1 | SEQ ID NO: 1 | SEQ ID NO: 43 |
| BORIS A2 | SEQ ID NO: 2 | SEQ ID NO: 43 |
| BORIS C1 | SEQ ID NO: 3 | SEQ ID NO: 43 |
| BORIS A4 | SEQ ID NO: 4 | SEQ ID NO: 25 |
| BORIS C2 | SEQ ID NO: 5 | SEQ ID NO: 25 |
| BORIS B1 | SEQ ID NO: 6 | SEQ ID NO: 26 |
| BORIS C3 | SEQ ID NO: 7 | SEQ ID NO: 27 |
| BORIS B2 | SEQ ID NO: 8 | SEQ ID NO: 28 |
| BORIS B3 | SEQ ID NO: 9 | SEQ ID NO: 29 |
| BORIS C4 | SEQ ID NO: 10 | SEQ ID NO: 30 |
| BORIS C5 | SEQ ID NO: 11 | SEQ ID NO: 31 |
| BORIS A5 | SEQ ID NO: 12 | SEQ ID NO: 32 |
| BORIS A6 | SEQ ID NO: 13 | SEQ ID NO: 33 |
| BORIS B4 | SEQ ID NO: 14 | SEQ ID NO: 34 |
| BORIS B5 | SEQ ID NO: 15 | SEQ ID NO: 35 |
| BORIS C6 | SEQ ID NO: 16 | SEQ ID NO: 36 |
| BORIS B6 | SEQ ID NO: 17 | SEQ ID NO: 37 |
| BORIS B7 | SEQ ID NO: 18 | SEQ ID NO: 37 |
| BORIS C7 | SEQ ID NO: 19 | SEQ ID NO: 38 |
| BORIS C8 | SEQ ID NO: 20 | SEQ ID NO: 39 |
| BORIS C9 | SEQ ID NO: 21 | SEQ ID NO: 38 |
| BORIS F6 | SEQ ID NO: 22 | SEQ ID NO: 40 |
| BORIS F7 | SEQ ID NO: 23 | SEQ ID NO: 41 |
| BORIS A3 | SEQ ID NO: 24 | SEQ ID NO: 42 |
| BORIS | SEQ ID NO: 44 | SEQ ID NO: 43 |

TABLE 2

| | K562 | MOLT-4 | CEM | RPMI8226 | HL-60 | SF-295 | SF-539 | SNB-19 | HS578T | MDAMB435 | COLO-205 | HCC-2998 |
| --- | --- | --- | --- | --- | --- | --- | --- | --- | --- | --- | --- | --- |
| BORIS A4/C2 | + | + | + | | + | + | | + | + | + | | + |
| BORIS C3 | + | | | | | | | | | | | |
| BORIS A5 | + | | | | | | | + | | + | + | |
| BORIS B1 | + | | | | | | | | | | | |
| BORIS F6 | + | | | + | | | | | | | | |
| BORIS F7 | + | | | + | | | | | | | | |

| | HCT-116 | HCT-15 | HT-29 | KM12 | SW-620 | A549 | EKVX | HOP-62 | HOP-92 | NCI-H322 | NCI-H226 |
| --- | --- | --- | --- | --- | --- | --- | --- | --- | --- | --- | --- |
| BORIS A4/C2 | + | | + | + | + | + | + | + | + | + | + |
| BORIS C3 | | | | | | | | + | + | | |
| BORIS A5 | + | | | | + | | + | + | + | | |
| BORIS B1 | | | | + | + | | + | + | | | |
| BORIS F6 | | | | | + | | | | | | |
| BORIS F7 | | | | | | | | | | + | |

| | NCI-H23 | NCI-H460 | NCI-H522 | LOX | M14 | MALME3M | SK-MEL-2 | SK-MEL28 | SK-MEL-5 | UACC-257 | UACC-62 |
| --- | --- | --- | --- | --- | --- | --- | --- | --- | --- | --- | --- |
| BORIS A4/C2 | + | + | + | + | | + | + | | + | + | + |
| BORIS C3 | | | | | | + | | | | | + |
| BORIS A5 | | | | + | + | | | | + | + | + |
| BORIS B1 | | | | | | | | | | | |
| BORIS F6 | | | | | | | | | | | |
| BORIS F7 | | | | | | | | | | | + |

| | ARD-RES | OVCAR-3 | OVCAR-4 | OVCAR-5 | OVCAR-8 | 786-0 | ACHN | RXF-393 | SN12C | TK-10 | UO-31 | PC-3 |
| --- | --- | --- | --- | --- | --- | --- | --- | --- | --- | --- | --- | --- |
| BORIS A4/C2 | + | | + | + | + | + | + | + | + | + | + | |
| BORIS C3 | + | | | | + | | | | | | | |
| BORIS A5 | + | | | | + | | | | | | | |
| BORIS B1 | + | | | | + | | | | | | | |
| BORIS F6 | + | | | | + | | | | | | | |
| BORIS F7 | + | + | | | + | + | | | | | | + |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever the invention is described with reference to open-ended terms (e.g., comprising), it is specifically contemplated that a qualified or closed-ended term (e.g., consisting essentially of or consisting of) can be used instead. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated or purified polypeptide comprising an amino acid sequence selected from the group consisting of SEQ ID NOs: 26-42.

2. A method of detecting a cancer characterized by abnormal BORIS expression in a mammal suspected of having cancer, wherein the expression of the one or more polypeptides in the tissue or body fluid is upregulated as compared to expression of the one or more polypeptides, which method comprises testing for the expression of one or more of the polypeptides of claim 1 in a tissue or body fluid of a mammal in the absence of cancer.

3. The method of claim 2, wherein testing for the expression of the one or more polypeptides comprises contacting a sample of body fluid or tissue of the mammal with an antibody to the one or more polypeptides, and detecting the binding of the antibody with one or more polypeptides from the sample.

4. The method of claim 2, wherein testing for the expression of the one or more polypeptides comprises detecting the presence of one or more auto-antibodies to the one or more polypeptides.

5. The method of claim 4, wherein detecting the presence of one or more auto-antibodies to the one or more polypeptides comprises contacting a sample of body fluid or tissue of the mammal with a probe comprising an immunogenic portion of the amino acid sequence of the one or more polypeptides, and detecting the binding of the probe with an auto-antibody from the sample.

6. The method of claim 2, wherein the method comprises testing for the expression of two or more different polypeptides, each of which comprises an amino acid sequence selected from the group consisting of SEQ ID NOs: 26-42.

7. The method of claim 2, wherein the method further comprises comparing the expression of the one or more polypeptides in the mammal with a control.

8. The method of claim 7, wherein the control is a BORIS expression pattern of a mammal known to be afflicted with a particular cancer associated with abnormal BORIS expression.

9. A kit for the detection of BORIS expression in a mammal, which kit comprises
   (a) a probe set comprising one or more probes that bind to (i) a BORIS isoform polypeptide, or (ii) an auto-antibody to a BORIS isoform polypeptide, wherein the BORIS isoform polypeptide comprises an amino acid sequence selected from the group consisting of SEQ ID NOs: 26-42, and
   (b) a reagent that facilitates the detection of the probe.

10. The kit of claim 9, wherein the probe set comprises one or more auto-antibodies to a BORIS isoform polypeptide.

11. The kit of claim 9, wherein the probe set comprises one or more BORIS isoform polypeptides.

12. The kit of claim 9, wherein the kit further comprises a BORIS expression profile of one or more types of cancer.

13. An antibody or antibody fragment that binds to the polypeptide of claim 1.

14. A composition comprising the antibody or antibody fragment of claim 13 and a carrier.

15. A method of treating or preventing a cancer associated with abnormal BORIS expression in a mammal comprising administering the antibody or antibody fragment of claim 13 to a mammal afflicted with a cancer associated with abnormal BORIS expression, wherein the antibody selectively binds to a BORIS isoform polypeptide.

16. A cell comprising the polypeptide of claim 1.

17. The method of claim 2, wherein the cancer is testes cancer.

* * * * *

SEQUENCE LISTING

```
<160> NUMBER OF SEQ ID NOS: 50

<210> SEQ ID NO 1
<211> LENGTH: 3601
<212> TYPE: DNA
<213> ORGANISM: Homo sapiens

<400> SEQUENCE: 1
attccacccc tcccccagt atctcagtgc ctcctgtggg ccctcctccc ctccttatcc      60 attcccctc agatctccca ggcccctgc aggccctcgt gccctcctta cttccccccc     120
gggtctccca gcgcccctg cggggccctc ctcccttcct catccacttc aaccccaagg    180
ccaagtcatt atggcagcca ctgagatctc tgtcctttct gagcaattca ccaagatcaa    240
agaactcgag ttgatgccgg aaaaaggcct gaaggaggag gaaaaagacg gagtgtgcag    300
agagaaagac catcggagcc ctagtgagtt ggaggccgag cgtacctctg gggccttcca    360
ggacagcgtc ctggaggaag aagtggagct ggtgctggcc ccctcggagg agagcgagaa    420
gtacatcctg accctgcaga cggtgcactt cacttctgaa gctgtggagt tgcaggatat    480
gagcttgctg agcatacagc agcaagaagg ggtgcaggtg gtggtgcaac agcctggccc    540
tgggttgctg tggcttgagg aagggccccg gcagagcctg cagcagtgtg tggccattag    600
tatccagcaa gagctgtact ccccgcaaga gatggaggtg ttgcagttcc acgctctaga    660
ggagaatgtg atggtggcca gtgaagacag taagttagcg gtgagcctgg ctgaaactgc    720
tggactgatc aagctcgagg aagagcagga gaagaaccag ttattggctg aaagaacaaa    780
ggagcagctc ttttttgtgg aaacaatgtc aggagatgaa agaagtgacg aaattgttct    840
cacagtttca aattcaaatg tggaagaaca agaggatcaa cctacagctg gtcaagcaga    900
tgctgaaaag gccaaatcta caaaaaatca aagaaagaca aagggagcaa aaggaacctt    960
ccactgtgat gtctgcatgt tcacctcttc tagaatgtca agttttaatc gtcatatgaa   1020
aactcacacc agtgagaagc ctcacctgtg tcacctctgc ctgaaaacct tccgtacggt   1080
cactctgctg cggaaccatg ttaacaccca cacaggaacc aggccctaca gtgtaacga   1140
```

```
ctgcaacatg gcatttgtca ccagtggaga actcgtccga cacaggcgct ataaacatac    1200
tcatgagaaa ccctttaaat gttccatgtg caagtatgcc agtgtggagg caagtaaatt    1260
gaagcgccat gtccgatccc acactgggga gcgccccttt cagtgttgcc agtgcagcta    1320
tgccagcaga gatacctaca agctgaaacg ccacatgaga acgcactcag gtgagaagcc    1380
ttacgaatgc cacatctgcc acaccgctt cacccagagc gggaccatga aaatacatat    1440
tctgcagaaa cacggcgaaa atgtccccaa ataccagtgt ccccattgtg ccaccatcat    1500
tgcacggaaa agcgacctac gtgtgcatat gcgcaacttg catgcttaca gcgctgcaga    1560
gctgaaatgc cgctactgtt ctgctgtctt ccatgaacgc tatgccctca ttcagcacca    1620
gaaaactcat aagaatgaga agaggttcaa gtgcaaacac tgcagttatg cctgcaagca    1680
ggaacgtcat atgaccgctc acattcgtac ccacactgga gagaaaccat tcacctgcct    1740
ttcttgcaat aaatgtttcc gacagaagca acttctaaac gctcacttca ggaaatacca    1800
cgatgcaaat tcatcccga ctgtttacaa atgctccaag tgtggcaaag cttttcccg    1860 ctggattaac ctgcacagac attcggagaa gtgtggatca ggggaagcaa agtcggctgc    1920
ttcaggaaag ggaagaagaa caagaaagag gaagcagacc atcctgaagg aagccacaaa    1980
gggtcagaag gaagctgcga agggatggaa ggaagccgcg aacggagacg aagctgctgc    2040
tgaggaggct tccaccacga agggagaaca gttcccagga gagatgtttc ctgtcgcctg    2100
cagagaaacc acagccagag tcaaagagga agtggatgaa ggcgtgacct gtgaaatgct    2160
cctcaacacg atggataagt gagagggatt cgggttgcgt gttcactgcc cccaattcct    2220
aaagcaagtt agaagttttt agcatttaag gtgtgaaatg ctcctcaaca cgatggataa    2280
gtgagagaga gtcaggttgc atgttcactg cccctaattc ctaaagcaag ttagaaattt    2340
ttagcatttt ctttgaaaca attaagttca tgacaatgga tgacacaagt ttgaggtagt    2400
gtctagaatt gttctcctgt ttgtagctgg atatttcaaa gaaacattgc aggtatttta    2460 taaaagttttt aaaccttgaa tgagagggta acacctcaaa cctatggatt cattcacttg    2520
atattggcaa ggtggcccac aatgagtgag tagtgatttt tggatatttc aaaatagtct    2580
agaccagcta gtgcttccac agtcaaagct ggacattttt atgttgcatt atatacaccc    2640
atgatatttc taataatata tggttttaaa cattaaagac aaatgttttt atacaaatga    2700
attttctaca aaatttaaag ctaccataat gcttttaatt agttctaaat tcaaccaaaa    2760
aatgttttac tcttataaaa aggaaaactg agtaggaaat gaaatactag attagactag    2820
aaaataagga ataatcgat tttactttgg tataggagca aggttcacct ttagattttt    2880
gtattctctt ttaattatgc tccttggcag gtatgaaatt gccctggtta cattccatta    2940
ttgcttatta gtatttcact ccataaccct tttttctgct aaaactactc tttttatatt    3000
tgtaaaataa ttggcagagt gagaagaaac ataaaatcag ataaggcaaa tgtgtacctg    3060
taaggaattt gtacttttc ataatgccca gtgattagtg agtatttccc ttttgccagt    3120
tgacaagatt tttccaccct cgagcagcgt gagagatgcc tctttaacac ttgaaattca    3180
tttctatctg gatacagagg cagattttc ttcattgctt agttgagcag tttgttttgc    3240
tgccaacctg tctccacccc tgtatttcaa gatcattgat aagccctaaa ttcaaattct    3300
taagatatgg accttttatt gaaaatatca caagttcaga atccctatac aatgtgaata    3360
tgtggaaata atttcccagc aggaagagca ttatattctc tttgtaccag caaattaatt    3420
taactcaact cacatgagat ttaaattctg tgggctgtag tatgccatca ttgtgactga    3480
atttgtgcaa tggtttctta attttttac tgttatttaa agatgtttta cataattcaa    3540
```

```
taaaatgaaa tgacttaaaa ttgcaaaaaa aaaaaaaaaa aaaaaaaaaa aaaaaaaaaa    3600
a                                                                     3601
```

<210> SEQ ID NO 2
<211> LENGTH: 3701
<212> TYPE: DNA
<213> ORGANISM: Homo sapiens

<400> SEQUENCE: 2

```
attccacccc tcccccagt atctcagtgc ctcctgtggg ccctcctccc ctccttatcc      60
attcccctc agatctccca ggccccctgc aggccctcgt gccctcctta cttccccccc    120
gggtctccca gcgcccctg cggggccctc ctcccttcct catccacttc aaccccaagc    180
ccggcggcgg ccggctgtgg gctgcagcac gcggtgcacg aggcagagcc acaagccaa    240
agacggagtg ggccgagcat tccggccacg ccttccgcgg ccaagtcatt atggcagcca    300
ctgagatctc tgtcctttct gagcaattca ccaagatcaa agaactcgag ttgatgccgg    360
aaaaaggcct gaaggaggag gaaaaagacg gagtgtgcag agagaaagac catcggagcc    420
ctagtgagtt ggaggccgag cgtacctctg ggccttcca ggacagcgtc ctggaggaag    480
aagtggagct ggtgctggcc ccctcggagg agagcgagaa gtacatcctg accctgcaga    540
cggtgcactt cacttctgaa gctgtggagt tgcaggatat gagcttgctg agcatacagc    600
agcaagaagg ggtgcaggtg gtggtgcaac agcctggccc tgggttgctg tggcttgagg    660
aagggccccg gcagagcctg cagcagtgtg tggccattag tatccagcaa gagctgtact    720
ccccgcaaga gatggaggtg ttgcagttcc acgctctaga ggagaatgtg atggtggcca    780
gtgaagacag taagttagcg gtgagcctgg ctgaaactgc tggactgatc aagctcgagg    840
aagagcagga gaagaaccag ttattggctg aaagaacaaa ggagcagctc tttttttgtgg   900
aaacaatgtc aggagatgaa agaagtgacg aaattgttct cacagtttca aattcaaatg    960
tggaagaaca agaggatcaa cctacagctg gtcaagcaga tgctgaaaag gccaaatcta   1020
caaaaaatca agaaagaca aagggagcaa aaggaacctt ccactgtgat gtctgcatgt   1080
tcacctcttc tagaatgtca gttttaatc gtcatatgaa aactcacacc agtgagaagc   1140
ctcacctgtg tcacctctgc ctgaaaacct tccgtacggt cactctgctg cggaaccatg   1200
ttaacaccca cacaggaacc aggccctaca agtgtaacga ctgcaacatg gcatttgtca   1260
ccagtggaga actcgtccga cacaggcgct ataaacatac tcatgagaaa ccctttaaat   1320
gttccatgtg caagtatgcc agtgtggagg caagtaaatt gaagcgccat gtccgatccc   1380
acactgggga gcgcccttt cagtgttgcc agtgcagcta tgccagcaga gatacctaca   1440
agctgaaacg ccacatgaga acgcactcag gtgagaagcc ttacgaatgc cacatctgcc   1500
acacccgctt cacccagagc gggaccatga aaatacatat tctgcagaaa cacggcgaaa   1560
atgtccccaa ataccagtgt ccccattgtg ccaccatcat tgcacggaaa agcgacctac   1620
gtgtgcatat gcgcaacttg catgcttaca gcgctgcaga gctgaaatgc cgctactgtt   1680
ctgctgtctt ccatgaacgc tatgccctca ttcagcacca gaaaactcat aagaatgaga   1740
agaggttcaa gtgcaaacac tgcagttatg cctgcaagca ggaacgtcat atgaccgctc   1800
acattcgtac ccacactgga gagaaaccat tcacctgcct tcttgcaat aaatgtttcc   1860
gacagaagca acttctaaac gctcacttca ggaaatacca cgatgcaaat ttcatcccga   1920
ctgttttacaa atgctccaag tgtggcaaag gcttttcccg ctggattaac ctgcacagac   1980
attcggagaa gtgtggatca ggggaagcaa agtcggctgc ttcaggaaag ggaagaagaa   2040
```

```
caagaaagag gaagcagacc atcctgaagg aagccacaaa gggtcagaag gaagctgcga    2100
agggatggaa ggaagccgcg aacggagacg aagctgctgc tgaggaggct tccaccacga    2160
agggagaaca gttcccagga gagatgtttc ctgtcgcctg cagagaaacc acagccagag    2220
tcaaagagga agtggatgaa ggcgtgacct gtgaaatgct cctcaacacg atggataagt    2280
gagagggatt cgggttgcgt gttcactgcc cccaattcct aaagcaagtt agaagttttt    2340
agcatttaag gtgtgaaatg ctcctcaaca cgatggataa gtgagagaga gtcaggttgc    2400
atgttcactg cccctaattc ctaaagcaag ttagaaattt ttagcatttt ctttgaaaca    2460
attaagttca tgacaatgga tgacacaagt ttgaggtagt gtctagaatt gttctcctgt    2520
ttgtagctgg atatttcaaa gaaacattgc aggtatttta taaaagtttt aaaccttgaa    2580
tgagagggta acacctcaaa cctatggatt cattcacttg atattggcaa ggtggcccac    2640
aatgagtgag tagtgatttt tggatatttc aaaatagtct agaccagcta gtgcttccac    2700
agtcaaagct ggacattttt atgttgcatt atatacaccc atgatatttc taataatata    2760
tggttttaaa cattaaagac aaatgttttt atacaaatga attttctaca aaatttaaag    2820
ctaccataat gcttttaatt agttctaaat tcaaccaaaa aatgttttac tcttataaaa    2880
aggaaaactg agtaggaaat gaaatactag attagactag aaaataagga ataaatcgat    2940
tttactttgg tataggagca aggttcacct ttagattttt gtattctctt ttaattatgc    3000
tccttggcag gtatgaaatt gccctggtta cattccatta ttgcttatta gtatttcact    3060
ccataaccct ttttctgct aaaactactc tttttatatt tgtaaaataa ttggcagagt    3120
gagaagaaac ataaaatcag ataaggcaaa tgtgtacctg taaggaattt gtacttttc    3180 ataatgccca gtgattagtg agtatttccc ttttgccagt tgacaagatt tttccaccct    3240
cgagcagcgt gagagatgcc tctttaacac ttgaaattca tttctatctg gatacagagg    3300 cagattttc ttcattgctt agttgagcag tttgttttgc tgccaacctg tctccacccc    3360
tgtatttcaa gatcattgat aagccctaaa ttcaaattct taagatatgg acctttatt    3420 gaaaatatca aagttcaga atccctatac aatgtgaata tgtggaaata atttcccagc    3480
aggaagagca ttatattctc tttgtaccag caaattaatt taactcaact cacatgagat    3540
ttaaattctg tgggctgtag tatgccatca ttgtgactga atttgtgcaa tggtttctta    3600 attttttac tgttatttaa agatgtttta cataattcaa taaatgaaa tgacttaaaa    3660 ttgcaaaaaa aaaaaaaaaa aaaaaaaaaa aaaaaaaaa a    3701

<210> SEQ ID NO 3
<211> LENGTH: 4073
<212> TYPE: DNA
<213> ORGANISM: Homo sapiens

<400> SEQUENCE: 3
agggtaaagc aggggccctg ccaggcctcc gagggagtgt gcttggtctg gccgagggct      60
gcttggccaa gtctgggtgg gctcgaggcc actaggccca aagcctgcct ggctctgagg     120
gtgctaggtc tagaaccgtg cacgagggga atgcctgctc gggcccgaac ctcgctgggc     180
gccgggtgtg cactggcccg ggcctgcctt ggacctgaaa cttgctaggc ccaggatatg     240
cactggccga gagcctgctg ggcccaaacc ttactaggcc caggatgttc actgactgaa     300
ccggctcagg cctaaccttg ctaggcccag gatatgcact gggccagagt gtgctcaggc     360
ggaaccttgc caggcgcagg atgtgtgctg gccctaagcc tgctgaggcc caaacctgtt     420
cgttctaggg ttttgtacaa aatcctgctt tagcctaaat cctgcttagc cttgaccccc     480
```

```
tcctagaccc aagccagatc agcattgttc tgaccctact aagtccaaaa ccttttgagg    540
ccagaccttg tttcaactcc aaagcctgct aggttccagc accccccgca tccctcctca    600
taccaccccc ttctccccccc tatggaaacc gcttgcttat ttttcaaaca ggccaagtca   660
ttatggcagc cactgagatc tctgtccttt ctgagcaatt caccaagatc aaagaactcg    720
agttgatgcc ggaaaaaggc ctgaaggagg aggaaaaaga cggagtgtgc agagagaaag    780
accatcggag ccctagtgag ttggaggccg agcgtacctc tggggccttc caggacagcg    840
tcctggagga agaagtggag ctggtgctgg cccccctcgga ggagagcgag aagtacatcc   900
tgaccctgca gacggtgcac ttcacttctg aagctgtgga gttgcaggat atgagcttgc    960
tgagcataca gcagcaagaa ggggtgcagg tggtggtgca acagcctggc cctgggttgc   1020
tgtggcttga ggaagggccc cggcagagcc tgcagcagtg tgtggccatt agtatccagc   1080
aagagctgta ctccccgcaa gagatggagg tgttgcagtt ccacgctcta gaggagaatg   1140
tgatggtggc cagtgaagac agtaagttag cggtgagcct ggctgaaact gctggactga   1200
tcaagctcga ggaagagcag gagaagaacc agttattggc tgaaagaaca aaggagcagc   1260
tcttttttgt ggaaacaatg tcaggagatg aaagaagtga cgaaattgtt ctcacagttt   1320
caaattcaaa tgtggaagaa caagaggatc aacctacagc tggtcaagca gatgctgaaa   1380
aggccaaatc tacaaaaaat caagaaagaa caaagggagc aaaaggaacc ttccactgtg   1440
atgtctgcat gttcacctct tctagaatgt caagttttaa tcgtcatatg aaaactcaca   1500
ccagtgagaa gcctcacctg tgtcacctct gcctgaaaac cttccgtacg gtcactctgc   1560
tgcggaacca tgttaacacc cacacaggaa ccaggcccta caagtgtaac gactgcaaca   1620
tggcatttgt caccagtgga gaactcgtcc gacacaggcg ctataaacat actcatgaga   1680
aaccctttaa atgttccatg tgcaagtatg ccagtgtgga ggcaagtaaa ttgaagcgcc   1740
atgtccgatc ccacactggg gagcgcccct ttcagtgttg ccagtgcagc tatgccagca   1800
gagataccta caagctgaaa cgccacatga gaacgcactc aggtgagaag ccttacgaat   1860
gccacatctg ccacacccgc ttcacccaga gcgggaccat gaaaatacat attctgcaga   1920
aacacggcga aaatgtcccc aaataccagt gtccccattg tgccaccatc attgcacgga   1980
aaagcgacct acgtgtgcat atgcgcaact gcatgcttta cagcgctgca gagctgaaat   2040
gccgctactg ttctgctgtc ttccatgaac gctatgccct cattcagcac cagaaaactc   2100
ataagaatga aagaggttc aagtgcaaac actgcagtta tgcctgcaag caggaacgtc   2160
atatgaccgc tcacattcgt acccacactg gagagaaacc attcacctgc ctttcttgca   2220
ataaatgttt ccgacagaag caacttctaa acgctcactt caggaaatac cacgatgcaa   2280
atttcatccc gactgtttac aaatgctcca gtgtggcaa aggcttttcc cgctggatta   2340
acctgcacag acattcggag aagtgtggat caggggaagc aaaagtcggct gcttcaggaa   2400
agggaagaag aacaagaaag aggaagcaga ccatcctgaa ggaagccaca aagggtcaga   2460
aggaagctgc gaagggatgg aaggaagccg cgaacggaga cgaagctgct gctgaggagg   2520
cttccaccac gaagggagaa cagttcccag gagagatgtt tcctgtcgcc tgcagagaaa   2580
ccacagccag agtcaaagag gaagtggatg aaggcgtgac ctgtgaaatg ctcctcaaca   2640
cgatggataa gtgagaggga ttcggggttgc gtgttcactg cccccaattc ctaaagcaag   2700
ttagaagttt ttagcattta aggtgtgaaa tgctcctcaa cacgatggat aagtgagaga   2760
gagtcaggtt gcatgttcac tgcccctaat tcctaaagca agttagaaat ttttagcatt   2820
ttcttttgaaa caattaagtt catgacaatg gatgacacaa gtttgaggta gtgtctagaa   2880
```

| | |
|---|---:|
| ttgttctcct gtttgtagct ggatatttca agaaacatt gcaggtattt tataaaagtt | 2940 |
| ttaaaccttg aatgagaggg taacacctca aacctatgga ttcattcact tgatattggc | 3000 |
| aaggtggccc acaatgagtg agtagtgatt tttggatatt tcaaaatagt ctagaccagc | 3060 |
| tagtgcttcc acagtcaaag ctggacattt ttatgttgca ttatatacac ccatgatatt | 3120 |
| tctaataata tatggtttta aacattaaag acaaatgttt ttatacaaat gaattttcta | 3180 |
| caaaatttaa agctaccata atgcttttaa ttagttctaa attcaaccaa aaaatgtttt | 3240 |
| actcttataa aaaggaaaac tgagtaggaa atgaaatact agattagact agaaaataag | 3300 |
| gaataaatcg attttacttt ggtataggag caaggttcac ctttagattt ttgtattctc | 3360 |
| ttttaattat gctccttggc aggtatgaaa ttgccctggt tacattccat tattgcttat | 3420 |
| tagtatttca ctccataacc cttttttctg ctaaaactac tcttttttata tttgtaaaat | 3480 |
| aattggcaga gtgagaagaa acataaaatc agataaggca aatgtgtacc tgtaaggaat | 3540 |
| ttgtactttt tcataatgcc cagtgattag tgagtatttc ccttttgcca gttgacaaga | 3600 |
| ttttttccacc ctcgagcagc gtgagagatg cctctttaac acttgaaatt catttctatc | 3660 |
| tggatacaga ggcagatttt tcttcattgc ttagttgagc agtttgtttt gctgccaacc | 3720 |
| tgtctccacc cctgtatttc aagatcattg ataagcccta aattcaaatt cttaagatat | 3780 |
| ggaccttta ttgaaaatat cacaagttca gaatccctat acaatgtgaa tatgtggaaa | 3840 |
| taatttccca gcaggaagag cattatattc tctttgtacc agcaaattaa tttaactcaa | 3900 |
| ctcacatgag atttaaattc tgtgggctgt agtatgccat cattgtgact gaatttgtgc | 3960 |
| aatggtttct taattttttt actgttattt aaagatgttt tacataattc aataaaatga | 4020 |
| aatgacttaa aattgcaaaa aaaaaaaaa aaaaaaaaaa aaaaaaaaaa aaa | 4073 |

<210> SEQ ID NO 4
<211> LENGTH: 1529
<212> TYPE: DNA
<213> ORGANISM: Homo sapiens

<400> SEQUENCE: 4

| | |
|---|---:|
| attccacccc tcccccccagt atctcagtgc ctcctgtggg ccctcctccc ctccttatcc | 60 |
| attcccccctc agatctccca ggccccctgc aggccctcgt gccctcctta cttccccccc | 120 |
| gggtctccca gcgcccccctg cggggccctc ctcccttcct catccacttc aaccccaagg | 180 |
| ccaagtcatt atggcagcca ctgagatctc tgtcctttct gagcaattca ccaagatcaa | 240 |
| agaactcgag ttgatgccgg aaaaaggcct gaaggaggag gaaaaagacg gagtgtgcag | 300 |
| agagaaagac catcggagcc ctagtgagtt ggaggccgag cgtacctctg ggccttcca | 360 |
| ggacagcgtc ctggaggaag aagtggagct ggtgctggcc ccctcggagg agagcgagaa | 420 |
| gtacatcctg accctgcaga cggtgcactt cacttctgaa gctgtggagt gcaggatat | 480 |
| gagcttgctg agcatacagc agcaagaagg ggtgcaggtg gtggtgcaac agcctggccc | 540 |
| tgggttgctg tggcttgagg aagggccccg gcagagcctg cagcagtgtg tggccattag | 600 |
| tatccagcaa gagctgtact ccccgcaaga gatggaggtt ttgcagttcc acgctctaga | 660 |
| ggagaatgtg atggtggcca gtgaagacag taagttagcg gtgagcctgg ctgaaactgc | 720 |
| tggactgatc aagctcgagg aagagcagga gaagaaccag ttattggctg aaagaacaaa | 780 |
| ggagcagctc tttttttgtgg aaacaatgtc aggagatgaa agaagtgacg aaattgttct | 840 |
| cacagtttca aattcaaatg tggaagaaca agaggatcaa cctacagctg gtcaagcaga | 900 |
| tgctgaaaag gccaaatcta caaaaaatca agaaagaca aagggagcaa aaggaacctt | 960 |

-continued

```
ccactgtgat gtctgcatgt tcacctcttc tagaatgtca agttttaatc gtcatatgaa      1020
aactcacacc agtgagaagc ctcacctgtg tcacctctgc ctgaaaacct tccgtacggt      1080
cactctgctg cggaaccatg ttaacaccca caggaacc aggccctaca agtgtaacga       1140
ctgcaacatg gcatttgtca ccagtggaga actcgtccga cacaggcgct ataaacatac      1200
tcatgagaaa ccctttaaat gttccatgtg caagtatgcc agtgtggagg taaagccatt      1260
cttggacttg aagcttcatg gcatcttagt agaggctgct gtacaagtta ctccaagtgt      1320
aactaacagt agaatctgtt acaaacaggc ttttattat tcatataaaa tttatgcagg       1380
aaataatatg cattctcttt tatgaagtta aaatagaaaa ttggatttct ttgtttctttt      1440 gattactaat tagtgaaaat aatatgtaaa ggtttacaaa ttacaaataa accatctgtg      1500
gttaaaaaaa aaaaaaaaaa aaaaaaaaa                                        1529

<210> SEQ ID NO 5
<211> LENGTH: 2001
<212> TYPE: DNA
<213> ORGANISM: Homo sapiens

<400> SEQUENCE: 5
agggtaaagc aggggccctg ccaggcctcc gagggagtgt gcttggtctg gccgagggct        60
gcttggccaa gtctgggtgg gctcgaggcc actaggccca aagcctgcct ggctctgagg       120
gtgctaggtc tagaaccgtg cacgagggga atgcctgctc gggcccgaac ctcgctgggc       180
gccgggtgtg cactggcccg gggcctgctt ggacctgaaa cttgctaggc ccaggatatg       240
cactggccga gagcctgctg ggcccaaacc ttactaggcc caggatgttc actgactgaa       300
ccggctcagg cctaaccttg ctaggcccag gatatgcact gggccagagt gtgctcaggc       360
ggaaccttgc caggcgcagg atgtgtgctg gccctaagcc tgctgaggcc caaacctgtt       420
cgttctaggg ttttgtacaa aatcctgctt tagcctaaat cctgcttagc cttgaccccc       480
tcctagaccc aagccagatc agcattgttc tgaccctact aagtccaaaa ccttttgagg       540
ccagaccttg tttcaactcc aaagcctgct aggttccagc accccccgca tccctcctca      600
taccaccccc ttctcccccc tatggaaacc gcttgcttat ttttcaaaca ggccaagtca      660
ttatggcagc cactgagatc tctgtcccttt ctgagcaatt caccaagatc aaagaactcg      720
agttgatgcc ggaaaaaggc ctgaaggagg aggaaaaaga cggagtgtgc agagagaaag      780
accatcggag ccctagtgag ttggaggccg agcgtacctc tggggccttc caggacagcg      840
tcctggagga agaagtggag ctggtgctgg cccctcgga ggagagcgag aagtacatcc       900
tgaccctgca gacggtgcac ttcacttctg aagctgtgga gttgcaggat atgagcttgc      960
tgagcataca gcagcaagaa ggggtgcagg tggtggtgca acagcctggc ctgggttgc       1020 tgtggcttga ggaagggccc cggcagagcc tgcagcagtg tgtggccatt agtatccagc      1080
aagagctgta ctccccgcaa gagatggagg tgttgcagtt ccacgctcta gaggagaatg      1140
tgatggtggc cagtgaagac agtaagttag cggtgagcct ggctgaaact gctggactga      1200
tcaagctcga ggaagagcag gagaagaacc agttattggc tgaaagaaca aaggagcagc      1260
tcttttttgt ggaaacaatg tcaggagatg aaagaagtga cgaaattgtt ctcacagttt      1320
caaattcaaa tgtggaagaa cagaggatc aacctacagc tggtcaagca gatgctgaaa      1380
aggccaaatc tacaaaaaat caaagaaaga caaagggagc aaaaggaacc ttccactgtg      1440
atgtctgcat gttcacctct tctagaatgt caagttttaa tcgtcatatg aaaactcaca      1500
ccagtgagaa gcctcacctg tgtcacctct gcctgaaaac cttccgtacg gtcactctgc      1560
```

-continued

| | |
|---|---|
| tgcggaacca tgttaacacc cacacaggaa ccaggcccta caagtgtaac gactgcaaca | 1620 |
| tggcatttgt caccagtgga gaactcgtcc gacacaggcg ctataaacat actcatgaga | 1680 |
| aaccctttaa atgttccatg tgcaagtatg ccagtgtgga ggtaaagcca ttcttggact | 1740 |
| tgaagcttca tggcatctta gtagaggctg ctgtacaagt tactccaagt gtaactaaca | 1800 |
| gtagaatctg ttacaaacag gctttttatt attcatataa aatttatgca ggaaataata | 1860 |
| tgcattctct tttatgaagt taaaatagaa aattggattt ctttgtttct ttgattacta | 1920 |
| attagtgaaa ataatatgta aaggtttaca aattacaaat aaaccatctg tggttaaaaa | 1980 |
| aaaaaaaaaa aaaaaaaaaa a | 2001 |

<210> SEQ ID NO 6
<211> LENGTH: 2506
<212> TYPE: DNA
<213> ORGANISM: Homo sapiens

<400> SEQUENCE: 6

| | |
|---|---|
| ggcaccagac gcggtgcacg aggcagagcc acaagccaaa gacggagtgg gccgagcatt | 60 |
| ccggccacgc cttccgcggc caagtcatta tggcagccac tgagatctct gtcctttctg | 120 |
| agcaattcac caagatcaaa gaactcgagt tgatgccgga aaaaggcctg aaggaggagg | 180 |
| aaaaagacgg agtgtgcaga gagaaagacc atcggagccc tagtgagttg gaggccgagc | 240 |
| gtacctctgg ggccttccag acagcgtcc tggaggaaga agtggagctg gtgctggccc | 300 |
| cctcggagga gagcgagaag tacatcctga ccctgcagac ggtgcacttc acttctgaag | 360 |
| ctgtggagtt gcaggatatg agcttgctga gcatacagca gcaagaaggg gtgcaggtgg | 420 |
| tggtgcaaca gcctggccct gggttgctgt ggcttgagga agggccccgg cagagcctgc | 480 |
| agcagtgtgt ggccattagt atccagcaag agctgtactc cccgcaagag atggaggtgt | 540 |
| tgcagttcca cgctctagag gagaatgtga tggtggccag tgaagacagt aagttagcgg | 600 |
| tgagcctggc tgaaactact ggactgatca agctcgagga gagcaggag aagaaccagt | 660 |
| tattggctga agaacaaag gagcagctct tttttgtgga acaatgtca ggagatgaaa | 720 |
| gaagtgacga aattgttctc acagtttcaa attcaaatgt ggaagaacaa gaggatcaac | 780 |
| ctacagctgg tcaagcagat gctgaaaagg ccaaatctac aaaaaatcaa agaaagacaa | 840 |
| agggagcaaa aggaaccttc cactgtgatg tctgcatgtt caccctcttct agaatgtcaa | 900 |
| gttttaatcg tcatatgaaa actcacacca gtgagaagcc tcacctgtgt cacctctgcc | 960 |
| tgaaaacctt ccgtacggtc actctgctgc ggaaccatgt taacacccac acaggaacca | 1020 |
| ggccctacaa gtgtaacgac tgcaacatgg catttgtcac cagtggagaa ctcgtccgac | 1080 |
| acaggcgcta taaacatact catgagaaac cctttaaatg ttccatgtgc aagtatgcca | 1140 |
| gtgtggaggc aagtaaattg aagcgccatg tccgatccca cactggggag cgccccttc | 1200 |
| agtgttgcca gtgcagctat gccagcagag atacctacaa gctgaaacgc acatgagaa | 1260 |
| cgcactcagg tgagaagcct tacgaatgcc acatctgcca cacccgcttc acccagagcg | 1320 |
| ggaccatgaa atacatatt ctgcagaaac acggcgaaaa tgtccccaaa taccagtgtc | 1380 |
| cccattgtgc caccatcatt gcacggaaaa gcgacctacg tgtgcatatg cgcaacttgc | 1440 |
| atgcttacag cgctgcagag ctgaaatgcc gctactgttc tgctgtcttc catgaacgct | 1500 |
| atgccctcat tcagcaccag aaaactcata agaatgagaa gaggttcaag tgcaaacact | 1560 |
| gcagttatgc ctgcaagcag gaacgtcata tgaccgctca cattcgtacc cacactggag | 1620 |
| agaaaccatt cacctgcctt tcttgcaata atgtttccg acagaagcaa cttctaaacg | 1680 |

-continued

| | |
|---|---|
| ctcacttcag gaaataccac gatgcaaatt tcatcccgac tgtttacaaa tgctccaagt | 1740 |
| gtggcaaagg cttttcccgc tggattaacc tgcacagaca ttcggagaag tgtggatcag | 1800 |
| gggaagcaaa gtcggctgct tcaggaaagg gaagaagaac aagaagagg aagcagacca | 1860 |
| tcctgaagga agccacaaag ggtcagaagg aagctgcgaa gggatggaag gaagccgcga | 1920 |
| acggagacga agctgctgct gaggaggctt ccaccacgaa gggagaacag ttcccaggag | 1980 |
| agatgtttcc tgtcgcctgc agagaaacca cagccagagt caaagaggaa gtggatgaag | 2040 |
| gcgtgacctg tgaaatgctc ctcaacacga tggataattc cgcaggctgt acaggaagga | 2100 |
| tgatgttggt atctgcctgg cttctgggga ggcctcagga aacttacaat caaggcagaa | 2160 |
| ggcgaagagg gagtaggcgc gtcacatggt gaaagcagga gcgagagagg gggaggcgcc | 2220 |
| acactcctct gaacgaccag attccttgag aaccgccact gtcatgagga cagcaccaag | 2280 |
| cggatggtgc taaatcattc ctaagaaacc gcccccgtga tccagtcacc tcctaccagg | 2340 |
| ccccacctcc aacactgggg attacaattc aacatgagct ttggccaggg acaaatatcc | 2400 |
| aaactatatc atgtatttta ctacaaccaa atgtatgtta atttcaaaaa cagataacat | 2460 |
| aaatatgttt gaaaacgtga aaaaaaaaa aaaaaaaaa aaaaaa | 2506 |

<210> SEQ ID NO 7
<211> LENGTH: 2826
<212> TYPE: DNA
<213> ORGANISM: Homo sapiens

<400> SEQUENCE: 7

| | |
|---|---|
| agggtaaagc aggggccctg ccaggcctcc gagggagtgt gcttggtctg gccgagggct | 60 |
| gcttggccaa gtctgggtgg gctcgaggcc actaggccca aagcctgcct ggctctgagg | 120 |
| gtgctaggtc tagaaccgtg cacgagggga atgcctgctc gggcccgaac ctcgctgggc | 180 |
| gccgggtgtg cactggcccg gggcctgctt ggacctgaaa cttgctaggc ccaggatatg | 240 |
| cactggccga gagcctgctg ggcccaaacc ttactaggcc caggatgttc actgactgaa | 300 |
| ccggctcagg cctaaccttg ctaggcccag gatatgcact gggccagagt gtgctcaggc | 360 |
| ggaaccttgc caggcgcagg atgtgtgctg ccctaagcc tgctgaggcc caaacctgtt | 420 |
| cgttctaggg ttttgtacaa atcctgctt tagcctaaat cctgcttagc cttgaccccc | 480 |
| tcctagaccc aagccagatc agcattgttc tgaccctact aagtccaaaa ccttttgagg | 540 |
| ccagaccttg tttcaactcc aaagcctgct aggttccagc accccccgca tccctcctca | 600 |
| taccaccccc ttctcccccc tatggaaacc gcttgcttat ttttcaaaca ggccaagtca | 660 |
| ttatggcagc cactgagatc tctgtccttt ctgagcaatt caccaagatc aaagaactcg | 720 |
| agttgatgcc ggaaaaaggc ctgaaggagg aggaaaaaga cggagtgtgc agagagaaag | 780 |
| accatcggag ccctagtgag ttggaggccg agcgtacctc tggggccttc caggacagcg | 840 |
| tcctggagga agaagtggag ctggtgctgg cccctcgga ggagagcgag aagtacatcc | 900 |
| tgaccctgca gacggtgcac ttcacttctg aagctgtgga gttgcaggat atgagcttgc | 960 |
| tgagcataca gcagcaagaa ggggtgcagg tggtggtgca acagcctggc cctgggttgc | 1020 |
| tgtggcttga ggaagggccc cggcagagcc tgcagcagtg tgtggccatt agtatccagc | 1080 |
| aagagctgta ctccccgcaa gagatggagg tgttgcagtt ccacgctcta gaggagaatg | 1140 |
| tgatggtggc cagtgaagac agtaagttag cggtgagcct ggctgaaact actggactga | 1200 |
| tcaagctcga ggaagagcag gagaagaacc agttattggc tgaaagaaca aaggagcagc | 1260 |
| tcttttttgt ggaaacaatg tcaggagatg aaagaagtga cgaaattgtt ctcacagttt | 1320 |

|  |  |  |  | |
|---|---|---|---|---|
| caaattcaaa | tgtggaagaa | caagaggatc | aacctacagc | tggtcaagca gatgctgaaa | 1380 |
| aggccaaatc | tacaaaaaat | caagaaaaga | caaaggagc | aaaaggaacc ttccactgtg | 1440 |
| atgtctgcat | gttcacctct | tctagaatgt | caagttttaa | tcgtcatatg aaaactcaca | 1500 |
| ccagtgagaa | gcctcacctg | tgtcacctct | gcctgaaaac | cttccgtacg gtcactctgc | 1560 |
| tgcggaacca | tgttaacacc | cacacaggaa | ccaggcccta | caagtgtaac gactgcaaca | 1620 |
| tggcatttgt | caccagtgga | gaactcgtcc | gacacaggcg | ctataaacat actcatgaga | 1680 |
| aacccttta | atgttccatg | tgcaagtatg | ccagtgtgga | ggcaagtaaa ttgaagcgcc | 1740 |
| atgtccgatc | ccacactggg | gagcgcccct | tcagtgttg | ccagtgcagc tatgccagca | 1800 |
| gagataccta | caagctgaaa | cgccacatga | aacgcactc | aggtgagaag ccttacgaat | 1860 |
| gccacatctg | ccacacccgc | ttcacccaga | gcgggaccat | gaaaatacat attctgcaga | 1920 |
| aacacggcga | aaatgtcccc | aaataccagt | gtccccattg | tgccaccatc attgcacgga | 1980 |
| aaagcgacct | acgtgtgcat | atgcgcaact | tgcatgctta | cagcgctgca gagctgaaat | 2040 |
| gccgctactg | ttctgctgtc | ttccatgaac | gctatgccct | cattcagcac cagaaaactc | 2100 |
| ataagaatga | aagaggttc | aagtgcaaac | actgcagtta | tgcctgcaag caggaacgtc | 2160 |
| atatgaccgc | tcacattcgt | acccacactg | gagagaaacc | attcacctgc ctttcttgca | 2220 |
| ataaatgttt | ccgacagaag | caacttctaa | acgctcactt | caggaaatac cacgatgcaa | 2280 |
| atttcatccc | gactgtttac | aaatgctcca | agtgtggcaa | aggcttttcc cgctggatta | 2340 |
| acctgcacag | acattcggag | aagtgtggat | caggggaagc | aaagtcggct gcttcaggaa | 2400 |
| agggaagaag | aacaagaaag | aggaagcaga | ccatcctgaa | ggaagccaca aagggtcaga | 2460 |
| aggaagctgc | gaagggatgg | aaggaagccg | cgaacggaga | cggtgtgatc tcagctcacc | 2520 |
| gcaacctctg | cctcctgggt | tcaagtgatt | ctcatgcctc | agtctccgga gctgggatta | 2580 |
| cagatgcccg | ccaccacgcc | tggctaattg | ttctattatt | tttagtagag atggggtttt | 2640 |
| accatgtctc | tcactcctga | cctcaagtga | tctgcccgcc | tcggcctccc aaagtggtgg | 2700 |
| gattacaggc | atgagcccct | gtgcctggcc | tgatggcacc | agttttgtgg atctcagtgt | 2760 |
| ttcttttcat | atccaagaac | tgggtcttct | tgtctccctc | catccaccaa aaaaaaaaaa | 2820 |
| aaaaaa |  |  |  | | 2826 |

<210> SEQ ID NO 8
<211> LENGTH: 1489
<212> TYPE: DNA
<213> ORGANISM: Homo sapiens

<400> SEQUENCE: 8

|  |  |  |  | |
|---|---|---|---|---|
| ggcaccagac | gcggtgcacg | aggcagagcc | cacaagccaa | agacggagtg ggccgagcat | 60 |
| tccggccacg | ccttccgcgg | agcaaaagga | accttccact | gtgatgtctg catgttcacc | 120 |
| tcttctagaa | tgtcaagttt | taatcgtcat | atgaaaactc | acaccagtga gaagcctcac | 180 |
| ctgtgtcacc | tctgcctgaa | aaccttccgt | acggtcactc | tgctgcggaa ccatgttaac | 240 |
| acccacacag | gaaccaggcc | ctacaagtgt | aacgactgca | acatggcatt tgtcaccagt | 300 |
| ggagaactcg | tccgacacag | gcgctataaa | catactcatg | agaaaccctt taaatgttcc | 360 |
| atgtgcaagt | atgccagtgt | ggaggcaagt | aaattgaagc | gccatgtccg atcccacact | 420 |
| ggggagcgcc | cctttcagtg | ttgccagtgc | agctatgcca | gcagagatac ctacaagctg | 480 |
| aaacgccaca | tgagaacgca | ctcaggtgag | aagccttacg | aatgccacat ctgccacacc | 540 |
| cgcttcaccc | agagcgggac | catgaaaata | catattctgc | agaaacacgg cgaaaatgtc | 600 |

```
cccaaatacc agtgtcccca ttgtgccacc atcattgcac ggaaaagcga cctacgtgtg    660
catatgcgca acttgcatgc ttacagcgct gcagagctga aatgccgcta ctgttctgct    720
gtcttccatg aacgctatgc cctcattcag caccagaaaa ctcataagaa tgagaagagg    780
ttcaagtgca aacactgcag ttatgcctgc aagcaggaac gtcatatgac cgctcacatt    840
cgtacccaca ctggagagaa accattcacc tgcctttctt gcaataaatg tttccgacag    900
aagcaacttc taaacgctca cttcaggaaa taccacgatg caaatttcat cccgactgtt    960
tacaaatgct ccaagtgtgg caaaggcttt tcccgctgga ttaacctgca cagacattcg   1020
gagaagtgtg gatcagggga agcaaagtcg gctgcttcag gaaagggaag aagaacaaga   1080
aagaggaagc agaccatcct gaaggaagcc acaaagggtc agaaggaagc tgcgaaggga   1140
tggaaggaag ccgcgaacgg agacggtgtg atctcagctc accgcaacct ctgcctcctg   1200
ggttcaagtg attctcatgc ctcagtctcc ggagctggga ttacagatgc cgccaccac    1260 gcctggctaa ttgttctatt attttttagta gagatggggt tttaccatgt ctctcactcc   1320
tgacctcaag tgatctgccc gcctcggcct cccaaagtgg tgggattaca ggcatgagcc   1380
cctgtgcctg gcctgatggc accagttttg tggatctcag tgtttctttt catatccaag   1440
aactgggtct tcttgtctcc ctccatccac caaaaaaaaa aaaaaaaa                1489

<210> SEQ ID NO 9
<211> LENGTH: 1700
<212> TYPE: DNA
<213> ORGANISM: Homo sapiens

<400> SEQUENCE: 9
ggcaccagac gcggtgcacg aggcagagcc cacaagccaa agacggagtg ggccgagcat     60
tccggccacg ccttccgcgc tcgaggaaga gcaggagaag aaccagttat ggctgaaag    120 aacaaaggag cagctctttt ttgtggaaac aatgtcagga gatgaaagaa gtgacgaaat    180
tgttctcaca gtttcaaatt caaatgtgga agaacaagag gatcaaccta cagctggtca    240
agcagatgct gaaaaggcca aatctacaaa aaatcaaaga aagacaaagg gagcaaaagg    300
aaccttccac tgtgatgtct gcatgttcac ctcttctaga atgtcaagtt ttaatcgtca    360
tatgaaaact cacaccagtg agaagcctca cctgtgtcac ctctgcctga aaaccttccg    420
tacggtcact ctgctgcgga accatgttaa caccccacaca ggaaccaggc cctacaagtg    480
taacgactgc aacatggcat ttgtcaccag tggagaactc gtccgacaca ggcgctataa    540
acatactcat gagaaacccct ttaaatgttc catgtgcaag tatgccagtg tggaggcaag    600
taaattgaag cgccatgtcc gatcccacac tggggagcgc ccctttcagt gttgccagtg    660
cagctatgcc agcagagata cctacaagct gaaacgccac atgagaacgc actcaggtga    720
gaagccttac gaatgccaca tctgccacac ccgcttcacc cagagcggga ccatgaaaat    780
acatattctg cagaaacacg gcgaaaatgt ccccaaatac cagtgtcccc attgtgccac    840
catcattgca cggaaaagcg acctacgtgt gcatatgcgc aacttgcatg cttacagcgc    900
tgcagagctg aaatgccgct actgttctgc tgtcttccat gaacgctatg ccctcattca    960
gcaccagaaa actcataaga atgagaagag gttcaagtgc aaacactgca gttatgcctg   1020
caagcaggaa cgtcatatga ccgctcacat tcgtacccac actggagaga accattcacc   1080
ctgcctttct tgcaataaat gtttccgaca gaagcaactt ctaaacgctc acttcaggaa   1140
ataccacgat gcaaatttca tcccgactgt ttacaaatgc tccaagtgtg gcaaaggctt   1200
ttcccgctgg attaacctgc acagacattc ggagaagtgt ggatcagggg aagcaaagtc   1260
```

| | |
|---|---|
| ggctgcttca ggaaagggaa gaagaacaag aaagaggaag cagaccatcc tgaaggaagc | 1320 |
| cacaaagggt cagaaggaag ctgcgaaggg atggaaggaa gccgcgaacg gagacggtgt | 1380 |
| gatctcagct caccgcaacc tctgcctcct gggttcaagt gattctcatg cctcagtctc | 1440 |
| cggagctggg attacagatg cccgccacca cgcctggcta attgttctat tattttagt | 1500 |
| agagatgggg ttttaccatg tctctcactc ctgacctcaa gtgatctgcc cgcctcggcc | 1560 |
| tcccaaagtg gtgggattac aggcatgagc ccctgtgcct ggcctgatgg caccagtttt | 1620 |
| gtggatctca gtgtttcttt tcatatccaa gaactgggtc ttcttgtctc cctccatcca | 1680 |
| ccaaaaaaaa aaaaaaaaaa | 1700 |

<210> SEQ ID NO 10
<211> LENGTH: 2431
<212> TYPE: DNA
<213> ORGANISM: Homo sapiens

<400> SEQUENCE: 10

| | |
|---|---|
| agggtaaagc aggggccctg ccaggcctcc gagggagtgt gcttggtctg gccgagggct | 60 |
| gcttggccaa gtctgggtgg gctcgaggcc actaggccca aagcctgcct ggctctgagg | 120 |
| gtgctaggtc tagaaccgtg cacgagggga atgcctgctc gggcccgaac ctcgctgggc | 180 |
| gccgggtgtg cactggcccg gggcctgctt ggacctgaaa cttgctaggc ccaggatatg | 240 |
| cactggccga gagcctgctg ggcccaaacc ttactaggcc caggatgttc actgactgaa | 300 |
| ccggctcagg cctaaccttg ctaggcccag gatatgcact gggccagagt gtgctcaggc | 360 |
| ggaaccttgc caggcgcagg atgtgtgctg gccctaagcc tgctgaggcc caaacctgtt | 420 |
| cgttctaggg ttttgtacaa aatcctgctt tagcctaaat cctgcttagc cttgaccccc | 480 |
| tcctagaccc aagccagatc agcattgttc tgaccctact aagtccaaaa ccttttgagg | 540 |
| ccagaccttg tttcaactcc aaagcctgct aggttccagc accccccgca tccctcctca | 600 |
| taccaccccc ttctccccc tatggaaacc gcttgcttat ttttcaaaca ggccaagtca | 660 |
| ttatggcagc cactgagatc tctgtccttt ctgagcaatt caccaagatc aaagaactcg | 720 |
| agttgatgcc ggaaaaaggc ctgaaggagg aggaaaaaga cggagtgtgc agagagaaag | 780 |
| accatcggag ccctagtgag ttggaggccg agcgtacctc tggggccttc caggacagcg | 840 |
| tcctggagga agaagtggag ctggtgctgg ccccctcgga ggagagcgag aagtacatcc | 900 |
| tgaccctgca gacggtgcac ttcacttctg aagctgtgga gttgcaggat atgagcttgc | 960 |
| tgagcataca gcagcaagaa ggggtgcagg tggtggtgca acagcctggc cctgggttgc | 1020 |
| tgtggcttga ggaagggccc cggcagagcc tgcagcagtg tgtggccatt agtatccagc | 1080 |
| aagagctgta ctccccgcaa gagatggagg tgttgcagtt ccacgctcta gaggagaatg | 1140 |
| tgatggtggc cagtgaagac agtaagttag cggtgagcct ggctgaaact actggactga | 1200 |
| tcaagctcga ggaagagcag gagaagaacc agttattggc tgaaagaaca aaggagcagc | 1260 |
| tcttttttgt ggaaacaatg tcaggagatg aaagaagtga cgaaattgtt ctcacagttt | 1320 |
| caaattcaaa tgtggaagaa caagaggatc aacctacagc tggtcaagca gatgctgaaa | 1380 |
| aggccaaatc tacaaaaaat caaagaaaga caaagggagc aaaaggaacc ttccactgtg | 1440 |
| atgtctgcat gttcacctct tctagaatgt caagttttaa tcgtcatatg aaaactcaca | 1500 |
| ccagtgagaa gcctcacctg tgtcacctct gcctgaaaac cttccgtacg gtcactctgc | 1560 |
| tgcggaacca tgttaacacc cacacaggaa ccaggcccta caagtgtaac gactgcaaca | 1620 |
| tggcatttgt caccagtgga gaactcgtcc gacacaggcg ctataaacat actcatgaga | 1680 |

| | | | | |
|---|---|---|---|---|
| aacccttaa | atgttccatg | tgcaagtatg | ccagtgtgga | ggcaagtaaa ttgaagcgcc | 1740 |
| atgtccgatc | ccacactggg | gagcgcccct | ttcagtgttg | ccagtgcagc tatgccagca | 1800 |
| gagataccta | caagctgaaa | cgccacatga | gaacgcactc | agaagcaact tctaaacgct | 1860 |
| cacttcagga | ataccacga | tgcaaatttc | atcccgactg | tttacaaatg ctccaagtgt | 1920 |
| ggcaaaggct | tttcccgctg | gattaacctg | cacagacatt | cggagaagtg tggatcaggg | 1980 |
| gaagcaaagt | cggctgcttc | aggaaaggga | agaagaacaa | gaaagaggaa gcagaccatc | 2040 |
| ctgaaggaag | ccacaaaggg | tcagaaggaa | gctgcgaagg | gatggaagga agccgcgaac | 2100 |
| ggagacggtg | tgatctcagc | tcaccgcaac | ctctgcctcc | tgggttcaag tgattctcat | 2160 |
| gcctcagtct | ccggagctgg | gattacagat | gcccgccacc | acgcctggct aattgttcta | 2220 |
| ttatttttag | tagagatggg | gtttaccat | gtctctcact | cctgacctca agtgatctgc | 2280 |
| ccgcctcggc | ctcccaaagt | ggtgggatta | caggcatgag | cccctgtgcc tggcctgatg | 2340 |
| gcaccagttt | tgtggatctc | agtgtttctt | ttcatatcca | agaactgggt cttcttgtct | 2400 |
| ccctccatcc | accaaaaaaa | aaaaaaaaaa | a | | 2431 |

<210> SEQ ID NO 11
<211> LENGTH: 1827
<212> TYPE: DNA
<213> ORGANISM: Homo sapiens

<400> SEQUENCE: 11

| | | | | |
|---|---|---|---|---|
| agggtaaagc | aggggccctg | ccaggcctcc | gagggagtgt | gcttggtctg gccgagggct | 60 |
| gcttggccaa | gtctgggtgg | gctcgaggcc | actaggccca | aagcctgcct ggctctgagg | 120 |
| gtgctaggtc | tagaaccgtg | cacgagggga | atgcctgctc | gggcccgaac ctcgctgggc | 180 |
| gccgggtgtg | cactggcccg | gggcctgctt | ggacctgaaa | cttgctaggc ccaggatatg | 240 |
| cactggccga | gagcctgctg | ggcccaaacc | ttactaggcc | caggatgttc actgactgaa | 300 |
| ccggctcagg | cctaaccttg | ctaggcccag | gatatgcact | gggccagagt gtgctcaggc | 360 |
| ggaaccttgc | caggcgcagg | atgtgtgctg | gccctaagcc | tgctgaggcc caaacctgtt | 420 |
| cgttctaggg | ttttgtacaa | aatcctgctt | tagcctaaat | cctgcttagc cttgaccccc | 480 |
| tcctagaccc | aagccagatc | agcattgttc | tgaccctact | aagtccaaaa ccttttgagg | 540 |
| ccagaccttg | tttcaactcc | aaagcctgct | aggttccagc | accccccgca tccctcctca | 600 |
| taccacccc | ttctccccc | tatggaaacc | gcttgcttat | ttttcaaaca ggccaagtca | 660 |
| ttatggcagc | cactgagatc | tctgtccttt | ctgagcaatt | caccaagatc aaagaactcg | 720 |
| agttgatgcc | ggaaaaaggc | ctgaaggagg | aggaaaaaga | cggagtgtgc agagagaaag | 780 |
| accatcggag | ccctagtgag | ttggaggccg | agcgtacctc | tggggccttc caggacagcg | 840 |
| tcctggagga | agaagtggag | ctggtgctgg | cccccctcgga | ggagagcgag aagtacatcc | 900 |
| tgaccctgca | gacggtgcac | ttcacttctg | aagctgtgga | gttgcaggat atgagcttgc | 960 |
| tgagcataca | gcagcaagaa | ggggtgcagg | tggtggtgca | acagcctggc cctgggttgc | 1020 |
| tgtggcttga | ggaagggccc | cggcagagcc | tgcagcagtg | tgtggccatt agtatccagc | 1080 |
| aagagctgta | ctccccgcaa | gagatggagg | tgttgcagtt | ccacgctcta gaggagaatg | 1140 |
| tgatggtggc | cagtgaagac | agtaagttag | cggtgagcct | ggctgaaact actgactgaa | 1200 |
| tcaagctcga | ggaagagcag | gagaagaacc | agttattggc | tgaaagaaca aaggagcagc | 1260 |
| tcttttttgt | ggaaacaatg | tcaggagatg | aagaagtgga | cgaaattgtt ctcacagttt | 1320 |
| caaattcaaa | tgtggaagaa | caagaggatc | aacctacagc | tggtcaagca gatgctgaaa | 1380 |

```
aggccaaatc tacaaaaaat caaagaaaga caaagggagc aaaaggaacc ttccactgtg   1440
atgtctgcat gttcacctct tctagaatgt caagttttaa tcgtcatatg aaaactcaca   1500
ccagtgagaa gcctcacctg tgtcacctct gcctcctggg ttcaagtgat tctcatgcct   1560
cagtctccgg agctgggatt acagatgccc gccaccacgc ctggctaatt gttctattat   1620
ttttagtaga gatggggttt taccatgtct ctcactcctg acctcaagtg atctgcccgc   1680
ctcggcctcc caaagtggtg ggattacagg catgagcccc tgtgcctggc ctgatggcac   1740
cagttttgtg gatctcagtg tttcttttca tatccaagaa ctgggtcttc ttgtctccct   1800
ccatccacca aaaaaaaaaa aaaaaaa                                       1827

<210> SEQ ID NO 12
<211> LENGTH: 2297
<212> TYPE: DNA
<213> ORGANISM: Homo sapiens

<400> SEQUENCE: 12
attccacccc tcccccagt atctcagtgc ctcctgtggg ccctcctccc ctccttatcc      60 attcccctc agatctccca ggccccctgc aggccctcgt gccctcctta cttccccccc     120
gggtctccca gcgcccctg cggggccctc ctcccttcct catccacttc aaccccaagg     180
ccaagtcatt atggcagcca ctgagatctc tgtcctttct gagcaattca ccaagatcaa     240
agaactcgag ttgatgccgg aaaaaggcct gaaggaggag gaaaaagacg gagtgtgcag     300
agagaaagac catcggagcc ctagtgagtt ggaggccgag cgtacctctg ggccttcca      360 ggacagcgtc ctggaggaag aagtggagct ggtgctggcc ccctcggagg agagcgagaa     420
gtacatcctg accctgcaga cggtgcactt cacttctgaa gctgtggagt tgcaggatat     480
gagcttgctg agcatacagc agcaagaagg ggtgcaggtg gtggtgcaac agcctggccc     540
tgggttgctg tggcttgagg aagggccccg gcagagcctg cagcagtgtg tggccattag     600
tatccagcaa gagctgtact ccccgcaaga gatggaggtg ttgcagttcc acgtctctaga    660 ggagaatgtg atggtggcca gtgaagacag taagttagcg gtgagcctgg ctgaaactgc     720
tggactgatc aagctcgagg aagagcagga gaagaaccag ttattggctg aaagaacaaa     780
ggagcagctc ttttttgtgg aaacaatgtc aggagatgaa agaagtgacg aaattgttct     840
cacagtttca aattcaaatg tggaagaaca agaggatcaa cctacagctg gtcaagcaga     900
tgctgaaaag gccaaatcta caaaaatca agaaagaca aagggagcaa aaggaacctt      960
ccactgtgat gtctgcatgt tcacctcttc tagaatgtca gtttttaatc gtcatatgaa    1020
aactcacacc agtgagaagc ctcacctgtg tcacctctgc ctgaaaacct tccgtacggt    1080
cactctgctg cggaaccatg ttaacaccca cacaggaacc aggccctaca gtgtaacga     1140 ctgcaacatg gcatttgtca ccagtggaga actcgtccga cacaggcgct ataaacatac    1200
tcatgagaaa ccctttaaat gttccatgtg caagtatgcc agtgtggagg caagtaaatt    1260
gaagcgccat gtccgatccc acactgggga gcgcccctttt cagtgttgcc agtgcagcta    1320
tgccagcaga gataccctaca agctgaaacg ccacatgaga acgcactcag gtgagaagcc    1380
ttacgaatgc cacatctgcc acacccgctt cacccagagc gggaccatga aaatacatat    1440
tctgcagaaa cacggcgaaa atgtcccaa ataccagtgt ccccattgtg ccaccatcat    1500
tgcacggaaa agcgacctac gtgtgcatat gcgcaacttg catgcttaca gcgctgcaga    1560
gctgaaatgc cgctactgtt ctgctgtctt ccatgaacgc tatgccctca ttcagccacca    1620 gaaaactcat aagaatgaga agaggttcaa gtgcaaacac tgcagttatg cctgcaagca    1680
```

-continued

| | |
|---|---|
| ggaacgtcat atgaccgctc acattcgtac ccacactgga gagaaaccat tcacctgcct | 1740 |
| ttcttgcaat aaatgtttcc gacagaagca acttctaaac gctcacttca ggaaatacca | 1800 |
| cgatgcaaat ttcatcccga ctgtttacaa atgctccaag tgtggcaaag cttttcccg | 1860 |
| ctggattctc tgggttggga actcggaagt ggctgaactg ggtggtcctg gctcagggcc | 1920 |
| actcctgagg ctgcagtcag gatgtccgcc agggctgcat catccgaagg ctggactggg | 1980 |
| gccagaggat ccacttccag gacagctccg ccacacaact gctggcaccg gcctcagttc | 2040 |
| cttgctacag ggacctctct gcagggctgc ttgagtgtcc tcctgactca gagcaagtga | 2100 |
| gagagtgcaa gtaggaagcc atggtgcctt ttgcagtcta gtcctaaaag cggcacaaca | 2160 |
| gccagctgtg ggggctcaca cctgtaatcc cagtacttcg ggaggccaag gcaggtggat | 2220 |
| aacttgaggc caggagctca agaccagcct ggccaacatg gtgaaaccct gtctctacga | 2280 |
| aaaaaaaaaa aaaaaaa | 2297 |

<210> SEQ ID NO 13
<211> LENGTH: 2348
<212> TYPE: DNA
<213> ORGANISM: Homo sapiens

<400> SEQUENCE: 13

| | |
|---|---|
| attccaccc tcccccagt atctcagtgc ctcctgtggg ccctcctccc ctccttatcc | 60 |
| attccccctc agatctccca ggcccctgc aggccctcgt gccctcctta cttcccccc | 120 |
| gggtctccca gcgcccctg cggggccctc ctcccttcct catccacttc aaccccaagg | 180 |
| ccaagtcatt atggcagcca ctgagatctc tgtcctttct gagcaattca ccaagatcaa | 240 |
| agaactcgag ttgatgccgg aaaaaggcct gaaggaggag gaaaaagacg gagtgtgcag | 300 |
| agagaaagac catcggagcc ctagtgagtt ggaggccgag cgtacctctg ggccttcca | 360 |
| ggacagcgtc ctggaggaag aagtggagct ggtgctggcc ccctcggagg agagcgagaa | 420 |
| gtacatcctg accctgcaga cggtgcactt cacttctgaa gctgtggagt tgcaggatat | 480 |
| gagcttgctg agcatacagc agcaagaagg ggtgcaggtg gtggtgcaac agcctggccc | 540 |
| tgggttgctg tggcttgagg aagggccccg gcagagcctg cagcagtgtg tggccattag | 600 |
| tatccagcaa gagctgtact ccccgcaaga gatggaggtg ttgcagttcc acgctctaga | 660 |
| ggagaatgtg atggtggcca gtgaagacag taagttagcg gtgagcctgg ctgaaaactac | 720 |
| tggactgatc aagctcgagg aagagcagga gaagaaccag ttattggctg aaagaacaaa | 780 |
| ggagcagctc tttttttgtgg aaacaatgtc aggagatgaa agaagtgacg aaattgttct | 840 |
| cacagtttca aattcaaatg tggaagaaca agaggatcaa cctacagctg gtcaagcaga | 900 |
| tgctgaaaag gccaaatcta caaaaaatca agaaagaca aagggagcaa aggaaccttt | 960 |
| ccactgtgat gtctgcatgt tcacctcttc tagaatgtca agttttaatc gtcatatgaa | 1020 |
| aactcacacc agtgagaagc ctcacctgtg tcacctctgc ctgaaaacct tccgtacggt | 1080 |
| cactctgctg cggaaccatg ttaacaccca cagggaacc aggccctaca gtgtaacga | 1140 |
| ctgcaacatg gcatttgtca ccagtggaga actcgtccga cacaggcgct ataaacatac | 1200 |
| tcatgagaaa ccctttaaat gttccatgtg caagtatgcc agtgtggagg caagtaaatt | 1260 |
| gaagcgccat gtccgatccc acactgggga gcgcccctt cagtgttgcc agtgcagcta | 1320 |
| tgccagcaga gatacctaca agctgaaacg ccacatgaga acgcactcag gtgagaagcc | 1380 |
| ttacgaatgc cacatctgcc acacccgctt caccccgagc gggaccatga aaatacatat | 1440 |
| tctgcagaaa cacggcgaaa atgtccccaa ataccagtgt ccccattgtg ccaccatcat | 1500 |

-continued

```
tgcacggaaa agcgacctac gtgtgcatat gcgcaacttg catgcttaca gcgctgcaga    1560
gctgaaatgc cgctactgtt ctgctgtctt ccatgaacgc tatgccctca ttcagcacca    1620
gaaaactcat aagaatgaga agaggttcaa gtgcaaacac tgcagttatg cctgcaagca    1680
ggaacgtcat atgaccgctc acattcgtac ccacactgga gagaaaccat tcacctgcct    1740
ttcttgcaat aaatgtttcc gacagaagca acttctaaac gctcacttca ggaaatacca    1800
cgatgcaaat tcatcccga ctgtttacaa atgctccaag tgtggcaaag cttttcccg     1860
ctggattacc tcaaaatgga gtggcttaaa accacaaaca tttatcacct gacagattct    1920
ctgggttggg aactcggaag tggctgaact gggtggtcct ggctcagggc cactcctgag    1980
gctgcagtca ggatgtccgc cagggctgca tcatccgaag gctggactgg gccagagga    2040
tccacttcca ggacagctcc gccacacaac tgctggcacc ggcctcagtt ccttgctaca    2100
gggacctctc tgcagggctg cttgagtgtc ctcctgactc agagcaagtg agagagtgca    2160
agtaggaagc catggtgcct tttgcagtct agtcctaaaa gcggcacaac agccagctgt    2220
gggggctcac acctgtaatc ccagtacttc gggaggccaa ggcaggtgga taacttgagg    2280
ccaggagctc aagaccagcc tggccaacat ggtgaaaccc tgtctctacg aaaaaaaaa    2340
aaaaaaaa                                                            2348
```

<210> SEQ ID NO 14
<211> LENGTH: 1642
<212> TYPE: DNA
<213> ORGANISM: Homo sapiens

<400> SEQUENCE: 14

```
ggcaccagac gcggtgcacg aggcagagcc acaagccaaa gacggagtgg gccgagcatt      60
ccggccacgc cttccgcgct cgaggaagag caggagaaga accagttatt ggctgaaaga     120
acaaaggagc agctctttt tgtggaaaca atgtcaggag atgaaagaag tgacgaaatt     180
gttctcacag tttcaaattc aaatgtggaa gaacaagagg atcaacctac agctggtcaa     240
gcagatgctg aaaaggccaa atctacaaaa aatcaaagaa agacaaaggg agcaaaagga     300
accttccact gtgatgtctg catgttcacc tcttctagaa tgtcaagttt taatcgtcat     360
atgaaaactc acaccagtga aagcctcac ctgtgtcacc tctgcctgaa aaccttccgt     420
acggtcactc tgctgcggaa ccatgttaac acccacacag gaaccaggcc ctacaagtgt     480
aacgactgca acatggcatt tgtcaccagt ggagaactcg tccgacacag gcgctataaa     540
catactcatg agaaaccctt taatgttcc atgtgcaagt atgccagtgt ggaggcaagt     600
aaattgaagc gccatgtccg atcccacact ggggagcgcc ctttcagtg ttgccagtgc     660
agctatgcca gcagagatac ctacaagctg aaacgccaca tgagaacgca ctcaggtgag     720
aagccttacg aatgccacat ctgccacacc cgcttcaccc agagcgggac catgaaaata     780
catattctgc agaaacacgg cgaaaatgtc cccaaatacc agtgtcccca ttgtgccacc     840
atcattgcac ggaaaagcga cctacgtgtg catatgcgca acttgcatgc ttacagcgct     900
gcagagctga atgccgcta ctgttctgct gtcttccatg aacgctatgc cctcattcag     960
caccagaaaa ctcataagaa tgagaagagg ttcaagtgca aacactgcag ttatgcctgc    1020
aagcaggaac gtcatatgac cgctcacatt cgtacccaca ctggagagaa accattcacc    1080
tgccttttct tgcaataaatg tttccgacag aagcaacttc taaacgctca cttcaggaaa    1140
taccacgatg caaatttcat cccgactgtt tacaaatgct ccaagtgtgg caaaggcttt    1200
tcccgctgga ttctctgggt tgggaactcg gaagtggctg aactgggtgg tcctggctca    1260
```

```
gggccactcc tgaggctgca gtcaggatgt ccgccagggc tgcatcatcc gaaggctgga   1320
ctggggccag aggatccact tccaggacag ctccgccaca caactgctgg caccggcctc   1380
agttccttgc tacagggacc tctctgcagg gctgcttgag tgtcctcctg actcagagca   1440
agtgagagag tgcaagtagg aagccatggt gccttttgca gtctagtcct aaaagcggca   1500
caacagccag ctgtgggggc tcacacctgt aatcccagta cttcgggagg ccaaggcagg   1560
tggataactt gaggccagga gctcaagacc agcctggcca acatggtgaa accctgtctc   1620
tacgaaaaaa aaaaaaaaaa aa                                            1642

<210> SEQ ID NO 15
<211> LENGTH: 1515
<212> TYPE: DNA
<213> ORGANISM: Homo sapiens

<400> SEQUENCE: 15
ggcaccagac gcggtgcacg aggcagagcc acaagccaaa gacggagtgg gccgagcatt     60
ccggccacgc cttccgcgga gcaaaaggaa ccttccactg tgatgtctgc atgttcacct    120
cttctagaat gtcaagtttt aatcgtcata tgaaaactca caccagtgag aagcctcacc    180
tgtgtcacct ctgcctgaaa accttccgta cggtcactct gctgcggaac catgttaaca    240 cccacagg aaccaggccc tacaagtgta acgactgcaa catggcattt gtcaccagtg     300
gagaactcgt ccgacacagg cgctataaac atactcatga gaaccccttt aaatgttcca    360
tgtgcaagta tgccagtgtg gaggcaagta aattgaagcg ccatgtccga tcccacactg    420
gggagcgccc ctttcagtgt tgccagtgca gctatgccag cagagatacc tacaagctga    480
aacgccacat gagaacgcac tcaggtgaga agccttacga atgccacatc tgccacaccc    540
gcttcaccca gagcgggacc atgaaaatac atattctgca gaaacacggc gaaaatgtcc    600
ccaaatacca gtgtcccat tgtgccacca tcattgcacg gaaaagcgac ctacgtgtgc    660
atatgcgcaa cttgcatgct tacagcgctg cagagctgaa atgccgctac tgttctgctg    720
tcttccatga cgctatgcc ctcattcagc accagaaaac tcataagaat gagaagaggt    780
tcaagtgcaa acactgcagt tatgcctgca gcaggaacg tcatatgacc gctcacattc    840
gtacccacac tggagagaaa ccattcaccct gcctttcttg caataaatgt ttccgacaga    900
agcaacttct aaacgctcac ttcaggaaat accacgatgc aaatttcatc ccgactgttt    960
acaaatgctc caagtgtggc aaaggctttt cccgctgggt gttgtattag ttatctatt   1020 ctgtatgaca gattacctca aaatggagtg gcttaaaacc acaaacatt atcacctgac   1080 agattctctg ggttgggaac tcggaagtgg ctgaactggg tggtcctggc tcagggccac   1140
tcctgaggct gcagtcagga tgtccgccag ggctgcatca tccgaaggct ggactggggc   1200
cagaggatcc acttccagga cagctccgcc acacaactgc tggcaccggc tcagttcct   1260 tgctacaggg acctctctgc agggctgctt gagtgtcctc ctgactcaga gcaagtgaga   1320
gagtgcaagt aggaagccat ggtgcctttt gcagtctagt cctaaaagcg cacaacagc   1380 cagctgtggg ggctcacacc tgtaatccca gtacttcggg aggccaaggc aggtggataa   1440
cttgaggcca ggagctcaag accagcctgg ccaacatggt gaaaccctgt ctctacgaaa   1500
aaaaaaaaaa aaaaa                                                   1515

<210> SEQ ID NO 16
<211> LENGTH: 2336
<212> TYPE: DNA
<213> ORGANISM: Homo sapiens
```

<400> SEQUENCE: 16

```
agggtaaagc agggcccctg ccaggcctcc gagggagtgt gcttggtctg gccgagggct      60
gcttggccaa gtctgggtgg gctcgaggcc actaggccca aagcctgcct ggctctgagg     120
gtgctaggtc tagaaccgtg cacgagggga atgcctgctc gggcccgaac ctcgctgggc     180
gccgggtgtg cactggcccg gggcctgctt ggacctgaaa cttgctaggc ccaggatatg     240
cactggccga gagcctgctg ggcccaaacc ttactaggcc caggatgttc actgactgaa     300
ccggctcagg cctaaccttg ctaggcccag atatgcact gggccagagt gtgctcaggc      360
ggaaccttgc caggcgcagg atgtgtgctg ccctaagcc tgctgaggcc caaacctgtt      420
cgttctaggg ttttgtacaa atcctgctt tagcctaaat cctgcttagc cttgacccc       480
tcctagaccc aagccagatc agcattgttc tgaccctact aagtccaaaa ccttttgagg     540
ccagaccttg tttcaactcc aaagcctgct aggttccagc acccccgca tccctcctca      600
taccaccccc ttctcccccc tatggaaacc gcttgcttat ttttcaaaca ggccaagtca     660
ttatggcagc cactgagatc tctgtccttt ctgagcaatt caccaagatc aaagaactcg     720
agttgatgcc ggaaaaaggc ctgaaggagg aggaaaaaga cggagtgtgc agagagaaag     780
accatcggag ccctagtgag ttggaggccg agcgtacctc tggggccttc caggacagcg     840
tcctggagga agaagtggag ctggtgctgg cccccctcgga ggagagcgag aagtacatcc     900
tgaccctgca gacggtgcac ttcacttctg aagctgtgga gttgcaggat atgagcttgc     960
tgagcataca gcagcaagaa ggggtgcagg tggtggtgca acagcctggc cctgggttgc    1020
tgtggcttga ggaagggccc cggcagagcc tgcagcagtg tgtggccatt agtatccagc    1080
aagagctgta ctccccgcaa gagatggagg tgttgcagtt ccacgctcta gaggagaatg    1140
tgatggtggc cagtgaagac agtaagttag cggtgagcct ggctgaaact actggactga    1200
tcaagctcga ggaagagcag gagaagaacc agttattggc tgaaagaaca aaggagcagc    1260
tcttttttgt ggaaacaatg tcaggagatg aaagaagtga cgaaattgtt ctcacagttt    1320
caaattcaaa tgtggaagaa caagaggatc aacctacagc tggtcaagca gatgctgaaa    1380
aggccaaatc tacaaaaaat caagaaaga caaagggagc aaaagaacct tccactgtga    1440
tgtctgcatg ttcacctctt ctagaatgtc aagttttaat cgtcatatga aaactcacac    1500
cagtgagaag cctcacctgt gtcacctctg cctgaaaacc ttccgtacgg tcactctgct    1560
gcggaaccat gttaacaccc acacaggaac caggccctac aagtgtaacg actgcaacat    1620
ggcatttgtc accagtggag aactcgtccg acacaggcgc tataaacata tcatgagaa    1680
accctttaaa tgttccatgt gcaagtatgc cagtgtggag aacgtcata tgaccgctca    1740
cattcgtacc cacactggag agaaaccatt cacctgcctt tcttgcaata aatgtttccg    1800
acagaagcaa cttctaaacg ctcacttcag gaaataccac gatgcaaatt tcatcccgac    1860
tgtttacaaa tgctccaagt gtggcaaagg cttttccgc tggattctct gggttgggaa    1920
ctcggaagtg gctgaactgg gtggtcctgg ctcagggcca ctcctgaggc tgcagtcagg    1980
atgtccgcca gggctgcatc atccgaaggc tggactgggg ccagaggatc cacttccagg    2040
acagctccgc cacacaactg ctggcaccgg cctcagttcc ttgctacagg gacctctctg    2100
cagggctgct tgagtgtcct cctgactcag agcaagtgag agagtgcaag taggaagcca    2160
tggtgccttt tgcagtctag tcctaaaagc ggcacaacag ccagctgtgg gggctcacac    2220
ctgtaatccc agtacttcgg gaggccaagg caggtggata acttgaggcc aggagctcaa    2280
gaccagcctg gccaacatgg tgaaaccctg tctctacgaa aaaaaaaaaa aaaaaa        2336
```

<210> SEQ ID NO 17
<211> LENGTH: 3708
<212> TYPE: DNA
<213> ORGANISM: Homo sapiens

<400> SEQUENCE: 17

```
ggcaccagac gcggtgcacg aggcagagcc cacaagccaa agacggagtg ggccgagcat      60
tccggccacg ccttccgcgg agcaaaagga accttccact gtgatgtctg catgttcacc     120
tcttctagaa tgtcaagttt taatcgtcat atgaaaactc acaccagtga aagcctcac      180
ctgtgtcacc tctgcctgaa aaccttccgt acggtcactc tgctgcggaa ccatgttaac     240
acccacacag gaaccaggcc ctacaagtgt aacgactgca acatggcatt tgtcaccagt     300
ggagaactcg tccgacacag gcgctataaa catactcatg agaaacccctt taaatgttcc     360
atgtgcaagt atgccagtgt ggaggcaagt aaattgaagc gccatgtccg atcccacact     420
ggggagcgcc cctttcagtg ttgccagtgc agctatgcca gcagagatac ctacaagctg     480
aaacgccaca tgagaacgca ctcaggtaag ggctctggtg ctgaaggcct gatacctaca     540
gtgttaactc ttaaagcaag cttaaaaaa ttactttta ttggcacaat taaagttcaa     600
aggtaaaagt ggattttgc gtgccttcat gataaaagaa tcttgatctg tacttttacc     660
tttatttagc agtaagagag tctgcataga tactgtgcca caaccccact gtgtggagta     720
aaacacaaag tatttgcttc cgtagatttt tcaggtattt aaaactcaac tcctggccag     780
gcatggtggc tcaaacctgt aatcccagca ctttgggagg ctgaggcagg aggatccctt     840
gagtccagga gtttgagacc agcctggtca acatagggag accctgtctc tacgagtaat     900
ttaaaaatta gctgggcctg gtggtgcaca cctgtggtcc cagctacttg ggaggctgaa     960
gcaggagaat cacttgaacc caggaggttg aggctgcagt gagccgggat tgcgccacta    1020
cactccagcc tgggtgacag agtgagaacc tgtctcaaaa aaaaagaaaa agtaaataaa    1080
aataaataaa agtcaactcc ttaattcatt cttcaacttt aaggcaaaac ataaagtgtg    1140
ctgcttttgt aacagaggta cttgatgtct tgtgttaaga atacatttat gtgtacttct    1200
tggttattcg tacagcccca tggatgtgaa ccaccttgaa ctcttgcgta gccaccagat    1260
gcggggaagt catgtctctg gtccatcatg gacacagctg tacttgacat aagctgtctg    1320
ggcttgattt gggagtctca tactaattgg gggttgtccg gtgagaaggg ggttgataaa    1380
ggaggcttgg ggcaaaaaaa aaaacactt tcagcacagg tggcctttgg caaggatcag    1440
gcctggaggg ggaatcactt tgttgtctgc atctcaggtg agaagcctta cgaatgccac    1500
atctgccaca cccgcttcac ccagagcggg accatgaaaa tacatattct gcagaaacac    1560
ggcgaaaatg tccccaaata ccagtgtccc cattgtgcca ccatcattgc acggaaaagc    1620
gacctacgtg tgcatatgcg caacttgcat gcttacagcg ctgcagagct gaaatgccgc    1680
tactgttctg ctgtcttcca tgaacgctat gccctcattc agcaccagaa aactcataag    1740
aatgagaaga ggttcaagtg caaacactgc agttatgcct gcaagcagga acgtcatatg    1800
accgctcaca ttcgtaccca cactggagag aaaccattca cctgcctttc ttgcaataaa    1860
tgtttccgac agaagcaact tctaaacgct cacttcagga ataccacga tgcaaatttc    1920
atcccgactt tttacaaatg ctccaagtgt ggcaaaggct tttccgctg gattaacctg    1980
cacagacatt cggagaagtg tggatcaggg gaagcaaagt cggctgcttc aggaaaggga    2040
agaagaacaa gaaagaggaa gcagaccatc ctgaaggaag ccacaaaggg tcagaaggaa    2100
gctgcgaagg gatggaagga agccgcgaac ggagacgaag ctgctgctga ggaggcttcc    2160
```

```
accacgaagg gagaacagtt cccaggagag atgtttcctg tcgcctgcag agaaaccaca    2220
gccagagtca aagaggaagt ggatgaaggc gtgacctgtg aaatgctcct caacacgatg    2280
gataagtgag agggattcgg gttgcgtgtt cactgccccc aattcctaaa gcaagttaga    2340 agttttagc atttaaggtg tgaaatgctc ctcaacacga tggataagtg agagagagtc     2400
aggttgcatg ttcactgccc ctaattccta aagcaagtta gaattttta gcattttctt     2460 tgaaacaatt aagttcatga caatggatga cacaagtttg aggtagtgtc tagaattgtt    2520
ctcctgtttg tagctggata tttcaaagaa acattgcagg tattttataa aagttttaaa    2580
ccttgaatga gagggtaaca cctcaaacct atgcattcat tcacttgata ttggcaaggt    2640
ggcccacaat gagtgagtag tgattttgg atattcaaa atagtctaga ccagctagtg       2700
cttccacagt caaagctgga catttttatg ttgcattata tacacccatg atatttctaa    2760
taatatatgg ttttaaacat taaagacaaa tgttttata caaatgaatt ttctacaaaa      2820
tttaaagcta ccataatgct tttaattagt tctaaattca accaaaaat gttttactct       2880 tataaaaagg aaaactgagt aggaaatgaa atactagatt agactagaaa ataaggaata    2940
aatcgatttt actttggtat aggagcaagg ttcacccttta gattttttgta ttctcttta     3000 attatgctcc ttggcaggta tgaaattgcc ctggttacat tccattattg cttattagta    3060
tttcactcca taacccttt ttctgctaaa actactcttt ttatatttgt aaaataattg       3120
gcagagtgag aagaaacata aaatcagata aggcaaatgt gtacctgtaa ggaatttgta    3180 cttttcata atgcccagtg attagtgagt atttcccttt tgccagttga caagattttt      3240
ccaccctcga gcagcgtgag agatgcctct taacacttg aaattcattt ctatctggat      3300
acagaggcag atttttcttc attgcttagt tgagcagttt gttttgctgc aacctgtct       3360 ccaccctgt atttcaagat cattgataag ccctaaattc aaattcttaa gatatggacc      3420
ttttattgaa aatatcacaa gttcagaatc cctatacaat gtgaatatgt ggaaataatt    3480
tcccagcagg aagagcatta tattctcttt gtaccagcaa attaatttaa ctcaactcac     3540
atgagattta aattctgtgg gctgtagtat gccatcattg tgactgaatt tgtgcaatgg    3600
tttcttaatt tttttactgt tatttaagaa tgttttcat aattcaataa aatgaaatga      3660
cttaaaattg caaaaaaaaa aaaaaaaaa aaaaaaaaa aaaaaaa                      3708

<210> SEQ ID NO 18
<211> LENGTH: 2985
<212> TYPE: DNA
<213> ORGANISM: Homo sapiens

<400> SEQUENCE: 18
ggcaccagac gcggtgcacg aggcagagcc cacaagccaa agacggagtg ggccgagcat    60
tccggccacg ccttccgcgg agcaaaagga accttccact gtgatgtctg catgttcacc    120
tcttctagaa tgtcaagttt taatcgtcat atgaaaactc acaccagtga gaagcctcac    180
ctgtgtcacc tctgcctgaa aaccttccgt acggtcactc tgctgcggaa ccatgttaac    240
acccacacag gaaccaggcc ctacaagtgt aacgactgca acatggcatt tgtcaccagt    300
ggagaactcg tccgacacag gcgctataaa catactcatg agaaaccctt taatgttcc     360 atgtgcaagt atgccagtgt ggaggcaagt aaattgaagc gccatgtccg atcccacact    420
ggggagcgcc cctttcagtg ttgccagtgc agctatgcca gcagagatac ctacaagctg    480
aaacgccaca tgagaacgca ctcaggtaag ggctctggtg ctgaaggcct gatacctaca    540
gtgttaactc ttaaagcaag cttttaaaaaa ttacttttta ttggcacaat taaagttcaa    600
```

```
aggtaaaagt ggatttttgc gtgccttcat gataaaagaa tcttgatctg tactttacc      660 tttatttagc agtaagagag tctgcataga tactgtgcca aacccccact gtgtggagta      720
aaacacaaag tatttgctyc cgtagatttt tcaggtgaga agccttacga atgccacatc      780
tgccacaccc gcttcaccca gagcgggacc atgaaaatac atattctgca gaaacacggc      840
gaaaatgtcc ccaaatacca gtgtccccat tgtgccacca tcattgcacg gaaaagcgac      900
ctacgtgtgc atatgcgcaa cttgcatgct tacagcgctg cagagctgaa atgccgctac      960
tgttctgctg tcttccatga acgctatgcc ctcattcagc accagaaaac tcataagaat     1020
gagaagaggt tcaagtgcaa acactgcagt tatgcctgca agcaggaacg tcatatgacc     1080
gctcacattc gtacccacac tggagagaaa ccattcacct gcctttcttg caataaatgt     1140
ttccgacaga agcaacttct aaacgctcac ttcaggaaat accacgatgc aaatttcatc     1200
ccgactgttt acaaatgctc caagtgtggc aaaggctttt cccgctggat taacctgcac     1260
agacattcgg agaagtgtgg atcagggaa gcaaagtcgg ctgcttcagg aaagggaaga     1320
agaacaagaa agaggaagca gaccatcctg aaggaagcca caagggtca gaaggaagct     1380 gcgaagggat ggaaggaagc cgcgaacgga gacgaagctg ctgctgagga ggcttccacc     1440
acgaagggag aacagttccc aggagagatg tttcctgtcg cctgcagaga aaccacagcc     1500
agagtcaaag aggaagtgga tgaaggcgtg acctgtgaaa tgctcctcaa cacgatggat     1560
aagtgagagg gattcgggtt gcgtgttcac tgcccccaat tcctaaagca agttagaagt     1620
ttttagcatt taaggtgtga aatgctcctc aacacgatgg ataagtgaga gagagtcagg     1680
ttgcatgttc actgcccccta attcctaaag caagttagaa attttttagca ttttctttga     1740 aacaattaag ttcatgacaa tggatgcacac aagtttgagg tagtgtctag aattgttctc     1800
ctgtttgtag ctggatattt caaagaaaca ttgcaggtat tttataaaag ttttaaacct     1860
tgaatgagag ggtaacacct caaacctatg gattcattca cttgatattg gcaaggtggc     1920
ccacaatgag tgagtagtga ttttttggata tttcaaaata gtctagacca gctagtgctt     1980
ccacagtcaa agctggacat ttttatgttg cattatatac acccatgata tttctaataa     2040
tatatggttt taaacattaa agacaaatgt ttttatacaa atgaatttc tacaaaattt      2100 aaagctacca taatgctttt aattagttct aaattcaacc aaaaaatgtt ttactcttat     2160
aaaaaggaaa actgagtagg aaatgaaata ctagattaga ctagaaaata aggaataaat     2220
cgattttact ttggtatagg agcaaggttc acctttagat ttttgtattc tcttttaatt    2280
atgctccttg gcaggtatga aattgccctg gttacattcc attattgctt attagtattt    2340
cactccataa ccctttttttc tgctaaaact actctttta tatttgtaaa ataattggca    2400
gagtgagaag aaacataaaa tcagataagg caaatgtgta cctgtaagga atttgtactt    2460
tttcataatg cccagtgatt agtgagtatt tcccttttgc cagttgacaa gattttttcca    2520 ccctcgagca gcgtgagaga tgcctcttta acacttgaaa ttcatttcta tctggataca   2580
gaggcagatt tttcttcatt gcttagttga gcagtttgtt ttgctgccaa cctgtctcca   2640
cccctgtatt tcaagatcat tgataagccc taaattcaaa ttcttaagat atggaccttt   2700
tattgaaaat atcacaagtt cagaatccct atacaatgtg aatatgtgga ataatttcc   2760 cagcaggaag agcattatat tctctttgta ccagcaaatt aatttaactc aactcacatg   2820
agatttaaat tctgtgggct gtagtatgcc atcattgtga ctgaatttgt gcaatggttt   2880
cttaattttt ttactgttat ttaaagatgt tttacataat tcaataaaat gaaatgactt   2940
aaaattgcaa aaaaaaaaaa aaaaaaaaaa aaaaaaaaaa aaaaa                     2985
```

<210> SEQ ID NO 19
<211> LENGTH: 5045
<212> TYPE: DNA
<213> ORGANISM: Homo sapiens

<400> SEQUENCE: 19

| | | | | | |
|---|---|---|---|---|---|
| agggtaaagc | aggggccctg | ccaggcctcc | gagggagtgt | gcttggtctg | gccgagggct | 60 |
| gcttggccaa | gtctgggtgg | gctcgaggcc | actaggccca | agcctgcct | ggctctgagg | 120 |
| gtgctaggtc | tagaaccgtg | cacgagggga | atgcctgctc | gggcccgaac | ctcgctgggc | 180 |
| gccgggtgtg | cactggcccg | gggcctgctt | ggacctgaaa | cttgctaggc | ccaggatatg | 240 |
| cactggccga | gagcctgctg | ggcccaaacc | ttactaggcc | caggatgttc | actgactgaa | 300 |
| ccggctcagg | cctaaccttg | ctaggcccag | gatatgcact | gggccagagt | gtgctcaggc | 360 |
| ggaaccttgc | caggcgcagg | atgtgtgctg | gccctaagcc | tgctgaggcc | caaacctgtt | 420 |
| cgttctaggt | ttttgtacaa | aatcctgctt | tagcctaaat | cctgcttagc | cttgacccc | 480 |
| tcctagaccc | aagccagatc | agcattgttc | tgaccctact | aagtccaaaa | ccttttgagg | 540 |
| ccagaccttg | tttcaactcc | aaagcctgct | aggttccagc | accccccgca | tccctcctca | 600 |
| taccaccccc | ttctcccccc | tatggaaacc | gcttgcttat | ttttcaaaca | ggccaagtca | 660 |
| ttatggcagc | cactgagatc | tctgtccttt | ctgagcaatt | caccaagatc | aaagaactcg | 720 |
| agttgatgcc | ggaaaaaggc | ctgaaggagg | aggaaaaaga | cggagtgtgc | agagagaaag | 780 |
| accatcggag | ccctagtgag | ttggaggccg | agcgtacctc | tggggccttc | aggacagcg | 840 |
| tcctggagga | agaagtggag | ctggtgctgg | ccccctcgga | ggagagcgag | aagtacatcc | 900 |
| tgaccctgca | gacggtgcac | ttcacttctg | aagctgtgga | gttgcaggat | atgagcttgc | 960 |
| tgagcataca | gcagcaagaa | ggggtgcagg | tggtggtgca | acagcctggc | cctgggttgc | 1020 |
| tgtggcttga | ggaagggccc | cggcagagcc | tgcagcagtg | tgtggccatt | agtatccagc | 1080 |
| aagagctgta | ctccccgcaa | gagatggagg | tgttgcagtt | ccacgctcta | gaggagaatg | 1140 |
| tgatggtggc | cagtgaagac | agtaagttag | cggtgagcct | ggctgaaact | actggactga | 1200 |
| tcaagctcga | ggaagagcag | gagaagaacc | agttattggc | tgaaagaaca | aaggagcagc | 1260 |
| tcttttttgt | ggaaacaatg | tcaggagatg | aaagaagtga | cgaaattgtt | ctcacagttt | 1320 |
| caaattcaaa | tgtggaagaa | caagaggatc | aacctacagc | tggtcaagca | gatgctgaaa | 1380 |
| aggccaaatc | tacaaaaaat | caaagaaaga | caagggagc | aaaaggaacc | ttccactgtg | 1440 |
| atgtctgcat | gttcacctct | tctagaatgt | caagttttaa | tcgtcatatg | aaaactcaca | 1500 |
| ccagtgagaa | gcctcacctg | tgtcacctct | gcctgaaaac | cttccgtacg | gtcactctgc | 1560 |
| tgcggaacca | tgttaacacc | cacacaggaa | ccaggcccta | caagtgtaac | gactgcaaca | 1620 |
| tggcatttgt | caccagtgga | gaactcgtcc | gacacaggcg | ctataaacat | actcatgaga | 1680 |
| aacccttaa | atgttccatg | tgcaagtatg | ccagtgtgga | ggcaagtaaa | ttgaagcgcc | 1740 |
| atgtccgatc | ccacactggg | gagcgcccct | tcagtgttg | ccagtgcagc | tatgccagca | 1800 |
| gagataccta | caagctgaaa | cgccacatga | gaacgcactc | aggtaagggc | tctggtgctg | 1860 |
| aaggcctgat | acctacagtg | ttaactctta | agcaagctt | taaaaattta | cttttattg | 1920 |
| gcacaattaa | agttcaaagg | taaagtggaa | ttttgcgtg | ccttcatgat | aaaagaatct | 1980 |
| tgatctgtac | ttttaccttt | atttagcagt | aagagagtct | gcatagatac | tgtgccacaa | 2040 |
| ccccactgtg | tggagtaaaa | cacaaagtat | ttgcttccgt | agattttca | ggtatttaaa | 2100 |
| actcaactcc | tggccaggca | tggtggctca | aacctgtaat | cccagcactt | tgggaggctg | 2160 |

```
aggcaggagg atcccttgag tccaggagtt tgagaccagc ctggtcaaca tagggagacc    2220
ctgtctctac gagtaattta aaaattagct gggcctggtg gtgcacacct gtggtcccag    2280
ctacttggga ggctgaagca ggagaatcac ttgaacccag gaggttgagg ctgcagtgag    2340 ccggattgc gccactacac tccagcctgg gtgacagagt gagaacctgt ctcaaaaaaa     2400
aagaaaaagt aaataaaaat aaataaaagt caactcctta attcattctt caactttaag    2460
gcaaaacata aagtgtgctg cttttgtaac agaggtactt gatgtcttgt gttaagaata    2520
catttatgtg tacttcttgg ttattcgtac agccccatgg atgtgaacca ccttgaactc    2580
ttgcgtagcc accagatgcg gggaagtcat gtctctggtc catcatggac acagctgtac    2640
ttgacataag ctgtctgggc ttgatttggg agtctcatac taattggggg ttgtccggtg    2700
agaagggggt tgataaagga ggcttggggc aaaaaaaaaa aacactttca gcacaggtgg    2760
cctttggcaa ggatcaggcc tggaggggga atcactttgt tgtctgcatc tcaggtgaga    2820
agccttacga atgccacatc tgccacaccc gcttcaccca gagcgggacc atgaaaatac    2880
atattctgca gaaacacggc gaaaatgtcc ccaaatacca gtgtccccat tgtgccacca    2940
tcattgcacg gaaaagcgac ctacgtgtgc atatgcgcaa cttgcatgct tacagcgctg    3000
cagagctgaa atgccgctac tgttctgctg tcttccatga acgctatgcc ctcattcagc    3060
accagaaaac tcataagaat gagaagaggt tcaagtgcaa acactgcagt tatgcctgca    3120
agcaggaacg tcatatgacc gctcacattc gtacccacac tggagagaaa ccattcacct    3180
gcctttcttg caataaatgt ttccgacaga agcaacttct aaacgctcac ttcaggaaat    3240
accacgatgc aaatttcatc ccgactgttt acaaatgctc caagtgtggc aaaggctttt    3300
cccgctggat taacctgcac agacattcgg agaagtgtgg atcaggggaa gcaaagtcgg    3360
ctgcttcagg aaagggaaga agaacaagaa agaggaagca gaccatcctg aaggaagcca    3420
caaagggtca gaaggaagct gcgaagggat ggaaggaagc cgcgaacgga gacgaagctg    3480
ctgctgagga ggcttccacc acgaagggag aacagttccc aggagagatg tttcctgtcg    3540
cctgcagaga aaccacagcc agagtcaaag aggaagtgga tgaaggcgtg acctgtgaaa    3600
tgctcctcaa cacgatggat aagtgagagg gattcgggtt gcgtgttcac tgccccaat    3660 tcctaaagca agttagaagt ttttagcatt taaggtgtga atgctcctc aacacgatgg    3720 ataagtgaga gagagtcagg ttgcatgttc actgcccta attcctaaag caagttagaa    3780
atttttagca ttttctttga aacaattaag ttcatgacaa tggatgacac aagtttgagg    3840
tagtgtctag aattgttctc ctgtttgtag ctggatattt caaagaaaca ttgcaggtat    3900
tttataaaag ttttaaacct tgaatgagag ggtaacacct caaacctatg gattcattca    3960
cttgatattg gcaaggtggc ccacaatgag tgagtagtga ttttttggata tttcaaaata    4020 gtctagacca gctagtgctt ccacagtcaa agctggacat ttttatgttg cattatatac    4080
acccatgata tttctaataa tatatggttt taaacattaa agacaaatgt ttttatacaa    4140
atgaattttc tacaaaattt aaagctacca taatgctttt aattagttct aaattcaacc    4200
aaaaaatgtt ttactcttat aaaaaggaaa actgagtagg aaatgaaata ctagattaga    4260
ctagaaaata aggaataaat cgattttact ttggtatagg agcaaggttc acctttagat    4320
ttttgtattc tcttttaatt atgctccttg gcaggtatga aattgccctg ttacattcc    4380 attattgctt attagtattt cactccataa cccttttttc tgctaaaact actctttta    4440 tatttgtaaa ataattggca gagtgagaag aaacataaaa tcagataagg caaatgtgta    4500
cctgtaagga atttgtactt tttcataatg cccagtgatt agtgagtatt tccctttgc    4560
```

```
cagttgacaa gattttttcca ccctcgagca gcgtgagaga tgcctcttta acacttgaaa      4620
ttcatttcta tctggataca gaggcagatt tttcttcatt gcttagttga gcagtttgtt      4680
ttgctgccaa cctgtctcca ccctgtatt tcaagatcat tgataagccc taaattcaaa       4740
ttcttaagat atggaccttt tattgaaaat atcacaagtt cagaatccct atacaatgtg      4800
aatatgtgga ataatttcc cagcaggaag agcattatat tctctttgta ccagcaaatt      4860
aatttaactc aactcacatg agatttaaat tctgtgggct gtagtatgcc atcattgtga      4920
ctgaatttgt gcaatggttt cttaattttt ttactgttat ttaaagatgt tttacataat      4980
tcaataaaat gaaatgactt aaaattgcaa aaaaaaaaa aaaaaaaaaa aaaaaaaaa        5040 aaaaa                                                                  5045

<210> SEQ ID NO 20
<211> LENGTH: 3463
<212> TYPE: DNA
<213> ORGANISM: Homo sapiens

<400> SEQUENCE: 20
agggtaaagc aggggccctg ccaggcctcc gagggagtgt gcttggtctg gccgagggct        60
gcttggccaa gtctgggtgg gctcgaggcc actaggccca aagcctgcct ggctctgagg       120
gtgctaggtc tagaaccgtg cacgagggga atgcctgctc gggcccgaac ctcgctgggc       180
gccgggtgtg cactggcccg gggcctgctt ggacctgaaa cttgctaggc ccaggatatg       240
cactggccga gagcctgctg ggcccaaacc ttactaggcc caggatgttc actgactgaa       300
ccggctcagg cctaaccttg ctaggcccag gatatgcact gggccagagt gtgctcaggc       360
ggaaccttgc caggcgcagg atgtgtgctg ccctaagcc tgctgaggcc caaacctgtt       420
cgttctaggg ttttgtacaa aatcctgctt tagcctaaat cctgcttagc cttgaccccc       480
tcctagaccc aagccagatc agcattgttc tgaccctact aagtccaaaa ccttttgagg       540
ccagaccttg tttcaactcc aaagcctgct aggttccagc accccccgca tccctcctca       600 taccacccc ttctcccccc tatggaaacc gcttgcttat ttttcaaaca ggccaagtca       660
ttatggcagc cactgagatc tctgtccttt ctgagcaatt caccaagatc aaagaactcg       720
agttgatgcc ggaaaaggc ctgaaggagg aggaaaaaga cggagtgtgc agagagaaag       780
accatcggag ccctagtgag ttggaggccg agcgtacctc tggggccttc caggacagcg       840
tcctggagga agaagtggag ctggtgctgg ccccctcgga ggagcgagag aagtacatcc       900
tgaccctgca gacggtgcac ttcacttctg aagctgtgga gttgcaggat atgagcttgc       960
tgagcataca gcagcaagaa ggggtgcagg tggtggtgca acagcctggc cctgggttgc      1020
tgtggcttga ggaagggccc cggcagagcc tgcagcagtg tgtggccatt agtatccagc      1080
aagagctgta ctccccgcaa gagatggagg tgttgcagtt ccacgctcta gaggagaatg      1140
tgatggtggc cagtgaagac agtaagttag cggtgagcct ggctgaaact gctggactga      1200
tcaagctcga ggaagagcag gagaagaacc agttattggc tgaaagaaca aaggagcagc      1260
tcttttttgt ggaaacaatg tcaggagatg aaagaagtga cgaaattgtt ctcacagttt      1320
caaattcaaa tgtggaagaa caagaggatc aacctacagc tggtcaagca gatgctgaaa      1380
aggccaaatc tacaaaaaat caagaaaga caaagggagc aaaaggaacc ttccactgtg      1440
atgtctgcat gttcacctct tctagaatgt caagttttaa tcgtcatatg aaaactcaca      1500
ccagtgagaa gcctcacctg tgtcacctct gcctgaaaac cttccgtacg gtcactctgc      1560 tgccggaacca tgttaacacc cacacaggaa ccaggcccta caagtgtaac gactgcaaca      1620
```

| | |
|---|---:|
| tggcatttgt caccagtgga gaactcgtcc gacacaggcg ctataaacat actcatgaga | 1680 |
| aacccttttaa atgttccatg tgcaagtatg ccagtgtgga ggcaagtaaa ttgaagcgcc | 1740 |
| atgtccgatc ccacactggg gagcgcccct tcagtgttg ccagtgcagc tatgccagca | 1800 |
| gagataccta caagctgaaa cgccacatga gaacgcactc aggtgagaag ccttacgaat | 1860 |
| gccacatctg ccacacccgc ttcacccaga gcgggaccat gaaaatacat attctgcaga | 1920 |
| aacacggcga aaatgtcccc aaataccagt gtccccattg tgccaccatc attgcacgga | 1980 |
| aaagcgacct acgattcctg ggcctccctt ttccatgatc ttatttctct ttccaaaata | 2040 |
| tatgacactg tgatacacaa aaatatgtta gcagaacaaa aatttgacc cttttgccca | 2100 |
| aagagattct ggagatgaga tgaatttttt tgaaaacctt tctgaaaggc gaaaggtgtt | 2160 |
| ccacaaagtc ttcactttta ttttcatct ggaccattct gtcattgttg ccgtagatac | 2220 |
| cagcacatca caaaacacag tccagtgggg cttggtgggg cacaagtcta gccagttgct | 2280 |
| agactttttt gacaccatgg caaagtaaca tggtttatat ccatctcatg ccagtgggtg | 2340 |
| atacactcca catagcccta agatgcttt tataaacaca ttaattcttc cttcccatga | 2400 |
| ctgtatgaga aatcaagctc tctaaatgtc tgagtcactg tgggtaaggt ggagtagctc | 2460 |
| catcacacag ctgtccattg tcatttggct tcttacacaa gtatcacaag accatcatgc | 2520 |
| tttagactta gatgagcaaa cccagccaga ccttaccatg tgtctcaggt taatttcaac | 2580 |
| ataggaaata acagggcact gacttctaac aacgagtgga ttatttaagg tgtgcatatg | 2640 |
| cgcaacttgc atgcttacag cgctgcagag ctgaaatgcc gctactgttc tgctgtcttc | 2700 |
| catgaacgct atgccctcat tcagcaccag aaaactcata agaatgagaa gaggttcaag | 2760 |
| tgcaaacact gcagttatgc ctgcaagcag gaacgtcata tgaccgctca cattcgtacc | 2820 |
| cacactggag agaaaccatt cacctgcctt tcttgcaata aatgtttccg acagaagcaa | 2880 |
| cttctaaacg ctcacttcag gaaataccac gatgcaaatt tcatcccgac tgtttacaaa | 2940 |
| tgctccaagt gtggcaaagg cttttcccgc tggattaacc tgcacagaca ttcggagaag | 3000 |
| tgtggatcag gggaagcaaa gtcggctgct tcaggaaagg gaagaagaac aagaaagagg | 3060 |
| aagcagacca tcctgaagga agccacaaag ggtcagaagg aagctgcgaa gggatggaag | 3120 |
| gaagccgcga acggagacgg tgtgatctca gctcaccgca acctctgcct cctgggttca | 3180 |
| agtgattctc atgcctcagt ctccggagct gggattacag atgcccgcca ccacgcctgg | 3240 |
| ctaattgttc tattatttt agtagagatg gggttttacc atgtctctca ctcctgacct | 3300 |
| caagtgatct gcccgcctcg gcctcccaaa gtggtgggat tacaggcatg agcccctgtg | 3360 |
| cctggcctga tggcaccagt tttgtggatc tcagtgtttc ttttcatatc caagaactgg | 3420 |
| gtcttcttgt ctccctccat ccaccaaaaa aaaaaaaaa aaa | 3463 |

<210> SEQ ID NO 21
<211> LENGTH: 4322
<212> TYPE: DNA
<213> ORGANISM: Homo sapiens

<400> SEQUENCE: 21

| | |
|---|---:|
| agggtaaagc aggggccctg ccaggcctcc gagggagtgt gcttggtctg gccgagggct | 60 |
| gcttggccaa gtctgggtgg gctcgaggcc actaggccca aagcctgcct ggctctgagg | 120 |
| gtgctaggtc tagaaccgtg cacgagggga atgcctgctc gggcccgaac ctcgctgggc | 180 |
| gccgggtgtg cactggcccg gggcctgctt ggacctgaaa cttgctaggc ccaggatatg | 240 |
| cactggccga gagcctgctg ggcccaaacc ttactaggcc caggatgttc actgactgaa | 300 |

```
ccggctcagg cctaaccttg ctaggcccag gatatgcact gggccagagt gtgctcaggc    360
ggaaccttgc caggcgcagg atgtgtgctg ccctaagcc tgctgaggcc caaacctgtt    420
cgttctaggg ttttgtacaa aatcctgctt tagcctaaat cctgcttagc cttgaccccc    480
tcctagaccc aagccagatc agcattgttc tgaccctact aagtccaaaa ccttttgagg    540
ccagaccttg tttcaactcc aaagcctgct aggttccagc accccccgca tccctcctca    600
taccaccccc ttctccccc tatggaaacc gcttgcttat ttttcaaaca ggccaagtca    660
ttatggcagc cactgagatc tctgtccttt ctgagcaatt caccaagatc aaagaactcg    720
agttgatgcc ggaaaaaggc ctgaaggagg aggaaaaaga cggagtgtgc agagagaaag    780
accatcggag ccctagtgag ttggaggccg agcgtacctc tggggccttc caggacagcg    840
tcctggagga agaagtggag ctggtgctgg cccctcgga ggagagcgag aagtacatcc    900
tgaccctgca gacggtgcac ttcacttctg aagctgtgga gttgcaggat atgagcttgc    960
tgagcataca gcagcaagaa ggggtgcagg tggtggtgca acagcctggc cctgggttgc   1020
tgtggcttga ggaagggccc cggcagagcc tgcagcagtg tgtggccatt agtatccagc   1080
aagagctgta ctccccgcaa gagatggagg tgttgcagtt ccacgctcta gaggagaatg   1140
tgatggtggc cagtgaagac agtaagttag cggtgagcct ggctgaaact actggactga   1200
tcaagctcga ggaagagcag gagaagaacc agttattggc tgaaagaaca aaggagcagc   1260
tcttttttgt ggaaacaatg tcaggagatg aaagaagtga cgaaattgtt ctcacagttt   1320
caaattcaaa tgtggaagaa caagaggatc aacctacagc tggtcaagca gatgctgaaa   1380
aggccaaatc tacaaaaaat caaagaaaga caaagggagc aaaaggaacc ttccactgtg   1440
atgtctgcat gttcacctct tctagaatgt caagttttaa tcgtcatatg aaaactcaca   1500
ccagtgagaa gcctcacctg tgtcacctct gcctgaaaac cttccgtacg gtcactctgc   1560
tgcggaacca tgttaacacc cacacaggaa ccaggcccta caagtgtaac gactgcaaca   1620
tggcatttgt caccagtgga gaactcgtcc gacacaggcg ctataaacat actcatgaga   1680 aacccttaa atgttccatg tgcaagtatg ccagtgtgga ggcaagtaaa ttgaagcgcc   1740
atgtccgatc ccacactggg gagcgcccct ttcagtgttg ccagtgcagc tatgccagca   1800
gagataccta caagctgaaa cgccacatga gaacgcactc aggtaagggc tctggtgctg   1860
aaggcctgat acctacagtg ttaactctta agcaagctt taaaaaatta cttttattg   1920 gcacaattaa agttcaaagg taaaagtgga tttttgcgtg ccttcatgat aaaagaatct   1980
tgatctgtac ttttacccttt atttagcagt aagagagtct gcatagatac tgtgccacaa   2040
ccccactgtg tggagtaaaa cacaaagtat ttgctyccgt agattttca ggtgagaagc   2100 cttacgaatg ccacatctgc cacacccgct tcacccagag cggaccatg aaaatacata   2160 ttctgcagaa acacggcgaa aatgtcccca ataccagtg tccccattgt gccaccatca   2220
ttgcacggaa aagcgaccta cgtgtgcata tgcgcaactt gcatgcttac agcgctgcag   2280
agctgaaatg ccgctactgt tctgctgtct tccatgaacg ctatgccctc attcagcacc   2340
agaaaactca taagaatgag aagaggttca agtgcaaaca ctgcagttat gcctgcaagc   2400
aggaacgtca tatgaccgct cacattcgta cccacactgg agagaaacca ttcacctgcc   2460
tttcttgcaa taaatgtttc cgacagaagc aacttctaaa cgctcacttc aggaaatacc   2520
acgatgcaaa tttcatcccg actgtttaca aatgctccaa gtgtggcaaa ggcttttccc   2580
gctggattaa cctgcacaga cattcggaga agtgtggatc aggggaagca agtcggctg   2640 cttcaggaaa gggaagaaga acaagaaaga ggaagcagac catcctgaag gaagccacaa   2700
```

```
agggtcagaa ggaagctgcg aagggatgga aggaagccgc gaacggagac gaagctgctg    2760
ctgaggaggc ttccaccacg aagggagaac agttcccagg agagatgttt cctgtcgcct    2820
gcagagaaac cacagccaga gtcaaagagg aagtggatga aggcgtgacc tgtgaaatgc    2880
tcctcaacac gatggataag tgagagggat tcgggttgcg tgttcactgc ccccaattcc    2940
taaagcaagt tagaagtttt tagcatttaa ggtgtgaaat gctcctcaac acgatggata    3000
agtgagagag agtcaggttg catgttcact gcccctaatt cctaaagcaa gttagaaatt    3060
tttagcattt tctttgaaac aattaagttc atgacaatgg atgacacaag tttgaggtag    3120
tgtctagaat tgttctcctg tttgtagctg atatttcaa agaaacattg caggtatttt    3180
ataaaagttt taaaccttga atgagagggt aacacctcaa acctatggat tcattcactt    3240
gatattggca aggtggccca caatgagtga gtagtgattt ttggatattt caaaatagtc    3300
tagaccagct agtgcttcca cagtcaaagc tggacatttt tatgttgcat tatatacacc    3360
catgatattt ctaataatat atggttttaa acattaaaga caaatgtttt tatacaaatg    3420
aattttctac aaaatttaaa gctaccataa tgcttttaat tagttctaaa ttcaaccaaa    3480
aaatgtttta ctcttataaa aaggaaaact gagtaggaaa tgaaatacta gattagacta    3540
gaaaataagg aataaatcga ttttactttg gtataggagc aaggttcacc tttagatttt    3600
tgtattctct tttaattatg ctccttggca ggtatgaaat tgccctggtt acattccatt    3660
attgcttatt agtatttcac tccataaccc tttttctgc taaaactact ctttttatat    3720
ttgtaaaata attggcagag tgagaagaaa cataaaatca gataaggcaa atgtgtacct    3780
gtaaggaatt tgtactttt cataatgccc agtgattagt gagtatttcc cttttgccag    3840
ttgacaagat ttttccaccc tcgagcagcg tgagagatgc ctctttaaca cttgaaattc    3900
atttctatct ggatacagag gcagatttt cttcattgct tagttgagca gtttgttttg    3960
ctgccaacct gtctccaccc ctgtatttca agatcattga taagcccctaa attcaaattc    4020 ttaagatatg gaccttttat tgaaaatatc acaagttcag aatccctata caatgtgaat    4080
atgtggaaat aatttcccag caggaagagc attatattct ctttgtacca gcaaattaat    4140
ttaactcaac tcacatgaga tttaaattct gtgggctgta gtatgccatc attgtgactg    4200
aatttgtgca atggtttctt aatttttttta ctgttatta aagatgtttt acataattca    4260
ataaaatgaa atgacttaaa attgcaaaaa aaaaaaaaa aaaaaaaaa aaaaaaaaa    4320 aa                                                                   4322

<210> SEQ ID NO 22
<211> LENGTH: 745
<212> TYPE: DNA
<213> ORGANISM: Homo sapiens

<400> SEQUENCE: 22
ttacaaatgc tccaagtgtg caaaggctt tcccgctgg attaacctgc acagacattc      60
ggagaagtgt ggatcagggg aagcaaagtc ggctgcttca ggaaagggaa gaagaacaag    120
aaagaggaag cagaccatcc tgaaggaagc acaaagggt cagaaggaag ctgcgaaggg    180
atggaaggaa gccgcgaacg gagacgaagc tgctgctgag gaggcttcca ccacgaaggg    240
agaacagttc ccaggagaga tgtttcctgt cgcctgcaga gaaccacag ccagagtcaa    300 agaggaagtg gatgaaggcg tgacctgtga atgctcctc aacacgatgg ataaacatct    360
tgcacagatg ttggatctgt atcaaagttt gtcatggatt ttccttttggg gagagtgcta    420 ttataaatcg tactgttagc cactgcagta cattgagctc catagagaca gcgccggggc    480
```

```
aagtgagagc cgtacgggca ctgggcgact ctgtgcctcg ctgaagaaaa ataactaaac    540
atgggcaaag gagatcctaa gaagccgaga ggcaaaatgt catcatatgc attttttgtg    600
caaacttgtc gggaggagca taagaagaag cactcagatg cttcagtcaa cttctcagag    660
ttttctaaca agtgctcaga gaggtggaag accatgtctg ctaaagagaa aggaaaattt    720
gaggatatgg caaaggcgga caaga                                         745

<210> SEQ ID NO 23
<211> LENGTH: 605
<212> TYPE: DNA
<213> ORGANISM: Homo sapiens

<400> SEQUENCE: 23
ccgactgttt acaaatgctc caagtgtggc aaaggctttt cccgctggat taacctgcac     60
agacattcgg agaagtgtgg atcaggggaa gcaaagtcgg ctgcttcagg aaagggaaga    120
agaacaagaa agaggaagca gaccatcctg aaggaagcca caagggtca gaaggaagct    180 gcgaagggat ggaaggaagc cgcgaacgga gacgacatct tgcacagatg ttggatctgt    240
atcaaagttt gtcatggatt tccctttggg gagagtgcta ttataaatcg tactgttagc    300
cactgcagta cattgagctc catagagaca gcgccggggc aagtgagagc cgtacgggca    360
ctgggcgact ctgtgcctcg ctgaagaaaa ataactaaac atgggcaaag gagatcctaa    420
gaagccgaga ggcaaaatgt catcatatgc attttttgtg caaacttgtc gggaggagca    480
taagaagaag cactcagatg cttcagtcaa cttctcagag ttttctaaca agtgctcaga    540
gaggtggaag accatgtctg ctaaagagaa aggaaaattt gaggatatgg caaaggcgga    600
caaga                                                               605

<210> SEQ ID NO 24
<211> LENGTH: 3822
<212> TYPE: DNA
<213> ORGANISM: Homo sapiens

<400> SEQUENCE: 24
tcccaggccc cctgcaggcc ctcgtgccct ccttacttcc cccccgggtc tcccagcgcc     60
ccctgcgggg ccctcctccc ttcctcatcc acttcaaccc caaggtattt ccgtgcccct    120
gcaggaccct cctcccctcc ttaggcgctc ccccactacc cagtcttcca gtgccctgca    180
ggctctcctc ctctccttat ccaccccac cccaggtctc ccagtgccct gtatgggacc    240
ctcctcccct cctcatccac cccccaggt ccaccagtgc ccctctggg gtcctcctca    300 tccgtgctcc ccctccccct ccctactccc cttcccccct gccccacag tacatcaccc    360 cctcccccaa ccctgcctgg ctccgccccc ttcacgcccc ctcttttccg ctccgcgcct    420
gcgcactgcc accctccact ctcgcgccag cccggcggcg gccggctgtg ggctgcagca    480
cgcggtgcac gaggcagagc ccacaagcca aagacggagt gggccgagca ttccggccac    540
gccttccgcg gccaagtcat tatggcagcc actgagatct ctgtcctttc tgagcaattc    600
accaagatca agaactcga gttgatgccg gaaaaaggcc tgaaggagga ggaaaaagac    660
ggagtgtgca gagagaaaga ccatcggagc cctagtgagt tggaggccga gcgtacctct    720
ggggccttcc aggacagcgt cctggaggaa gaagtggagc tggtgctggc cccctcggag    780
gagagcgaga agtacatcct gaccctgcag acggtgcact tcacttctga agctgtggag    840
ttgcaggata tgagcttgct gagcatacag cagcaagaag gggtgcaggt ggtggtgcaa    900
cagcctggcc ctgggttgct gtggcttgag gaagggcccc ggcagagcct gcagcagtgt    960
```

```
gtggccatta gtatccagca agagctgtac tccccgcaag agatggaggt gttgcagttc      1020
cacgctctag aggagaatgt gatggtggcc agtgaagaca gtaagttagc ggtgagcctg      1080
gctgaaactg ctggactgat caagctcgag gaagagcagg agaagaacca gttattggct      1140
gaaagaacaa aggagcagct cttttttgtg gaaacaatgt caggagatga agaagtgac       1200 gaaattgttc tcacagtttc aaattcaaat gtggaagaac aagaggatca acctacagct      1260
ggtcaagcag atgctgaaaa ggccaaatct acaaaaaatc aaagaaagac aaagggagca      1320
aaaggaacct tccactgtga tgtctgcatg ttcacctctt ctagaatgtc aagttttaat      1380
cgtcatatga aaactcacac cagtgagaag cctcacctgt gtcacctctg cctgaaaacc      1440
ttccgtacgg tcactctgct gcggaaccat gttaacaccc acacaggaac caggccctac      1500
aagtgtaacg actgcaacat ggcatttgtc accagtggag aactcgtccg acacaggcgc      1560
tataaacata ctcatgagaa accctttaaa tgttccatgt gcaagtatgc cagtgtggag      1620
gcaagtaaat tgaagcgcca tgtccgatcc cacactgggg agcgcccctt tcagtgttgc      1680
cagtgcagct atgccagcag agatacctac aagctgaaac gccacatgag aacgcactca      1740
ggtgtgcata tgcgcaactt gcatgcttac agcgctgcag agctgaaatg ccgctactgt      1800
tctgctgtct tccatgaacg ctatgccctc attcagcacc agaaaactca taagaatgag      1860
aagaggttca gtgcaaaca ctgcagttat gcctgcaagc aggaacgtca tatgaccgct       1920
cacattcgta cccacactgg agagaaacca ttcacctgcc tttcttgcaa taaatgtttc      1980
cgacagaagc aacttctaaa cgctcacttc aggaaatacc acgatgcaaa tttcatcccg      2040
actgtttaca aatgctccaa gtgtggcaaa ggcttttccc gctggattaa cctgcacaga      2100
cattcggaga gtgtggatc aggggaagca aagtcggctg cttcaggaaa gggaagaaga       2160
acaagaaaga ggaagcagac catcctgaag gaagccacaa agggtcagaa ggaagctgcg      2220
aagggatgga aggaagccgc gaacggagac gaagctgctg ctgaggaggc ttccaccacg      2280
aagggagaac agttcccagg agagatgttt cctgtcgcct gcagagaaac cacagccaga      2340
gtcaaagagg aagtggatga aggcgtgacc tgtgaaatgc tcctcaacac gatggataag      2400
tgagagggat tcgggttgcg tgttcactgc ccccaattcc taaagcaagt tagaagtttt      2460
tagcatttaa ggtgtgaaat gctcctcaac acgatggata agtgagagag agtcaggttg      2520
catgttcact gccctaatt cctaaagcaa gttagaaatt tttagcattt tctttgaaac        2580
aattaagttc atgacaatgg atgacacaag tttgaggtag tgtctagaat tgttctcctg      2640
tttgtagctg atatttcaa agaaacattg caggtatttt ataaaagttt taaaccttga       2700
atgagagggt aacacctcaa acctatggat tcattcactt gatattggca aggtggccca      2760
caatgagtga gtagtgattt ttggatattt caaaatagtc tagaccagct agtgcttcca      2820
cagtcaaagc tggacatttt tatgttgcat tatatacacc catgatattt ctaataatat      2880
atggttttaa acattaaaga caaatgtttt tatacaaatg aatttctac aaaatttaaa       2940 gctaccataa tgcttttaat tagttctaaa ttcaaccaaa aatgttttta ctcttataaa      3000
aaggaaaact gagtaggaaa tgaaatacta gattagacta gaaataagg aataaatcga       3060 ttttactttg gtataggagc aaggttcacc tttagatttt tgtattctct tttaattatg      3120
ctccttggca ggtatgaaat tgccctggtt acattccatt attgcttatt agtatttcac      3180
tccataaccc ttttttctgc taaaactact ctttttatat ttgtaaaata attggcagag      3240
tgagaagaaa cataaaatca gataaggcaa atgtgtacct gtaaggaatt tgtactttt       3300 cataatgccc agtgattagt gagtatttcc cttttgccag ttgacaagat ttttccaccc      3360
```

-continued

```
tcgagcagcg tgagagatgc ctctttaaca cttgaaattc atttctatct ggatacagag    3420
gcagattttt cttcattgct tagttgagca gtttgttttg ctgccaacct gtctccaccc    3480
ctgtatttca agatcattga taagccctaa attcaaattc ttaagatatg gacctttat     3540 tgaaaatatc acaagttcag aatccctata caatgtgaat atgtggaaat aatttcccag    3600
caggaagagc attatattct ctttgtacca gcaaattaat ttaactcaac tcacatgaga    3660
tttaaattct gtgggctgta gtatgccatc attgtgactg aatttgtgca atggtttctt    3720
aattttttta ctgttattta aagatgtttt acataattca ataaaatgaa atgacttaaa    3780
attgcaaaaa aaaaaaaaaa aaaaaaaaaa aaaaaaaaaa aa                       3822
```

<210> SEQ ID NO 25
<211> LENGTH: 404
<212> TYPE: PRT
<213> ORGANISM: Homo sapiens

<400> SEQUENCE: 25

```
Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Gln Glu Gly Val Gln Val Val Val
            100                 105                 110

Gln Gln Pro Gly Pro Gly Leu Leu Trp Leu Glu Glu Gly Pro Arg Gln
        115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Ala Gly Leu Ile Lys Leu Glu Glu Gln Glu Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
        275                 280                 285

Leu Cys Leu Lys Thr Phe Arg Thr Val Thr Leu Leu Arg Asn His Val
    290                 295                 300
```

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Tyr Lys His
            325                 330                 335

Thr His Glu Lys Pro Phe Lys Cys Ser Met Cys Lys Tyr Ala Ser Val
            340                 345                 350

Glu Val Lys Pro Phe Leu Asp Leu Lys Leu His Gly Ile Leu Val Glu
            355                 360                 365

Ala Ala Val Gln Val Thr Pro Ser Val Thr Asn Ser Arg Ile Cys Tyr
            370                 375                 380

Lys Gln Ala Phe Tyr Tyr Ser Tyr Lys Ile Tyr Ala Gly Asn Asn Met
385                 390                 395                 400

His Ser Leu Leu

<210> SEQ ID NO 26
<211> LENGTH: 700
<212> TYPE: PRT
<213> ORGANISM: Homo sapiens

<400> SEQUENCE: 26

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Lys
            20                  25                  30

Asp Gly Val Cys Arg Glu Lys Asp His Arg Ser Pro Ser Glu Leu Glu
            35                  40                  45

Ala Glu Arg Thr Ser Gly Ala Phe Gln Asp Ser Val Leu Glu Glu Glu
50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Gln Glu Gly Val Gln Val Val Val
            100                 105                 110

Gln Gln Pro Gly Pro Gly Leu Leu Trp Leu Glu Glu Gly Pro Arg Gln
            115                 120                 125

Ser Leu Gln Gln Cys Val Ala Ile Ser Ile Gln Gln Glu Leu Tyr Ser
130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Thr Gly Leu Ile Lys Leu Glu Glu Glu Gln Glu Lys Asn Gln Leu Leu
            180                 185                 190

Ala Glu Arg Thr Lys Glu Gln Leu Phe Phe Val Glu Thr Met Ser Gly
            195                 200                 205

Asp Glu Arg Ser Asp Glu Ile Val Leu Thr Val Ser Asn Ser Asn Val
210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270

```
Asn Arg His Met Lys Thr His Thr Ser Glu Lys Pro His Leu Cys His
        275                 280                 285

Leu Cys Leu Lys Thr Phe Arg Thr Val Thr Leu Leu Arg Asn His Val
        290                 295                 300

Asn Thr His Thr Gly Thr Arg Pro Tyr Lys Cys Asn Asp Cys Asn Met
305                     310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
                340                 345                 350

Glu Ala Ser Lys Leu Lys Arg His Val Arg Ser His Thr Gly Glu Arg
        355                 360                 365

Pro Phe Gln Cys Cys Gln Cys Ser Tyr Ala Ser Arg Asp Thr Tyr Lys
        370                 375                 380

Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
                405                 410                 415

Ile Leu Gln Lys His Gly Glu Asn Val Pro Lys Tyr Gln Cys Pro His
        420                 425                 430

Cys Ala Thr Ile Ile Ala Arg Lys Ser Asp Leu Arg Val His Met Arg
        435                 440                 445

Asn Leu His Ala Tyr Ser Ala Ala Glu Leu Lys Cys Arg Tyr Cys Ser
450                 455                 460

Ala Val Phe His Glu Arg Tyr Ala Leu Ile Gln His Gln Lys Thr His
465                 470                 475                 480

Lys Asn Glu Lys Arg Phe Lys Cys Lys His Cys Ser Tyr Ala Cys Lys
                485                 490                 495

Gln Glu Arg His Met Thr Ala His Ile Arg Thr His Thr Gly Glu Lys
                500                 505                 510

Pro Phe Thr Cys Leu Ser Cys Asn Lys Cys Phe Arg Gln Lys Gln Leu
        515                 520                 525

Leu Asn Ala His Phe Arg Lys Tyr His Asp Ala Asn Phe Ile Pro Thr
        530                 535                 540

Val Tyr Lys Cys Ser Lys Cys Gly Lys Gly Phe Ser Arg Trp Ile Asn
545                 550                 555                 560

Leu His Arg His Ser Glu Lys Cys Gly Ser Gly Glu Ala Lys Ser Ala
                565                 570                 575

Ala Ser Gly Lys Gly Arg Arg Thr Arg Lys Arg Gln Thr Ile Leu
                580                 585                 590

Lys Glu Ala Thr Lys Gly Gln Lys Glu Ala Ala Lys Gly Trp Lys Glu
        595                 600                 605

Ala Ala Asn Gly Asp Glu Ala Ala Ala Glu Glu Ala Ser Thr Thr Lys
        610                 615                 620

Gly Glu Gln Phe Pro Gly Glu Met Phe Pro Val Ala Cys Arg Glu Thr
625                 630                 635                 640

Thr Ala Arg Val Lys Glu Glu Val Asp Glu Gly Val Thr Cys Glu Met
                645                 650                 655

Leu Leu Asn Thr Met Asp Asn Ser Ala Gly Cys Thr Gly Arg Met Met
                660                 665                 670

Leu Val Ser Ala Trp Leu Leu Gly Arg Pro Gln Glu Thr Tyr Asn Gln
        675                 680                 685

Gly Arg Arg Arg Gly Ser Arg Val Thr Trp
        690                 695                 700
```

<210> SEQ ID NO 27
<211> LENGTH: 665
<212> TYPE: PRT
<213> ORGANISM: Homo sapiens

<400> SEQUENCE: 27

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
                20                  25                  30

Asp Gly Val Cys Arg Glu Lys Asp His Arg Ser Pro Ser Glu Leu Glu
            35                  40                  45

Ala Glu Arg Thr Ser Gly Ala Phe Gln Asp Ser Val Leu Glu Glu Glu
        50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Glu Gly Val Gly Val Val Val
                100                 105                 110

Gln Gln Pro Gly Pro Gly Leu Leu Trp Leu Glu Glu Gly Pro Arg Gln
            115                 120                 125

Ser Leu Gln Gln Cys Val Ala Ile Ser Ile Gln Gln Glu Leu Tyr Ser
        130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Thr Gly Leu Ile Lys Leu Glu Glu Gln Glu Lys Asn Gln Leu Leu
                180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
        275                 280                 285

Leu Cys Leu Lys Thr Phe Arg Thr Val Thr Leu Leu Arg Asn His Val
    290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
            340                 345                 350

Glu Ala Ser Lys Leu Lys Arg His Val Arg Ser His Thr Gly Glu Arg
        355                 360                 365

Pro Phe Gln Cys Cys Gln Cys Ser Tyr Ala Ser Arg Asp Thr Tyr Lys
    370                 375                 380

```
Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
                405                 410                 415

Ile Leu Gln Lys His Gly Glu Asn Val Pro Lys Tyr Gln Cys Pro His
            420                 425                 430

Cys Ala Thr Ile Ile Ala Arg Lys Ser Asp Leu Arg Val His Met Arg
        435                 440                 445

Asn Leu His Ala Tyr Ser Ala Ala Glu Leu Lys Cys Arg Tyr Cys Ser
    450                 455                 460

Ala Val Phe His Glu Arg Tyr Ala Leu Ile Gln His Gln Lys Thr His
465                 470                 475                 480

Lys Asn Glu Lys Arg Phe Lys Cys Lys His Cys Ser Tyr Ala Cys Lys
                485                 490                 495

Gln Glu Arg His Met Thr Ala His Ile Arg Thr His Thr Gly Glu Lys
            500                 505                 510

Pro Phe Thr Cys Leu Ser Cys Asn Lys Cys Phe Arg Gln Lys Gln Leu
        515                 520                 525

Leu Asn Ala His Phe Arg Lys Tyr His Asp Ala Asn Phe Ile Pro Thr
    530                 535                 540

Val Tyr Lys Cys Ser Lys Cys Gly Lys Gly Phe Ser Arg Trp Ile Asn
545                 550                 555                 560

Leu His Arg His Ser Glu Lys Cys Gly Ser Gly Glu Ala Lys Ser Ala
                565                 570                 575

Ala Ser Gly Lys Gly Arg Arg Thr Arg Lys Arg Lys Gln Thr Ile Leu
            580                 585                 590

Lys Glu Ala Thr Lys Gly Gln Lys Glu Ala Ala Lys Gly Trp Lys Glu
        595                 600                 605

Ala Ala Asn Gly Asp Gly Val Ile Ser Ala His Arg Asn Leu Cys Leu
    610                 615                 620

Leu Gly Ser Ser Asp Ser His Ala Ser Val Ser Gly Ala Gly Ile Thr
625                 630                 635                 640

Asp Ala Arg His His Ala Trp Leu Ile Val Leu Leu Phe Leu Val Glu
                645                 650                 655

Met Gly Phe Tyr His Val Ser His Ser
            660                 665

<210> SEQ ID NO 28
<211> LENGTH: 403
<212> TYPE: PRT
<213> ORGANISM: Homo sapiens

<400> SEQUENCE: 28

Met Phe Thr Ser Ser Arg Met Ser Ser Phe Asn Arg His Met Lys Thr
1               5                   10                  15

His Thr Ser Glu Lys Pro His Leu Cys His Leu Cys Leu Lys Thr Phe
            20                  25                  30

Arg Thr Val Thr Leu Leu Arg Asn His Val Asn Thr His Thr Gly Thr
        35                  40                  45

Arg Pro Tyr Lys Cys Asn Asp Cys Asn Met Ala Phe Val Thr Ser Gly
    50                  55                  60

Glu Leu Val Arg His Arg Arg Tyr Lys His Thr His Glu Lys Pro Phe
65                  70                  75                  80

Lys Cys Ser Met Cys Lys Tyr Ala Ser Val Glu Ala Ser Lys Leu Lys
                85                  90                  95
```

```
Arg His Val Arg Ser His Thr Gly Glu Arg Pro Phe Gln Cys Cys Gln
            100                 105                 110

Cys Ser Tyr Ala Ser Arg Asp Thr Tyr Lys Leu Lys Arg His Met Arg
        115                 120                 125

Thr His Ser Gly Glu Lys Pro Tyr Glu Cys His Ile Cys His Thr Arg
130                 135                 140

Phe Thr Gln Ser Gly Thr Met Lys Ile His Ile Leu Gln Lys His Gly
145                 150                 155                 160

Glu Asn Val Pro Lys Tyr Gln Cys Pro His Cys Ala Thr Ile Ile Ala
                165                 170                 175

Arg Lys Ser Asp Leu Arg Val His Met Arg Asn Leu His Ala Tyr Ser
            180                 185                 190

Ala Ala Glu Leu Lys Cys Arg Tyr Cys Ser Ala Val Phe His Glu Arg
        195                 200                 205

Tyr Ala Leu Ile Gln His Gln Lys Thr His Lys Asn Glu Lys Arg Phe
    210                 215                 220

Lys Cys Lys His Cys Ser Tyr Ala Cys Lys Gln Glu Arg His Met Thr
225                 230                 235                 240

Ala His Ile Arg Thr His Thr Gly Glu Lys Pro Phe Thr Cys Leu Ser
                245                 250                 255

Cys Asn Lys Cys Phe Arg Gln Lys Gln Leu Leu Asn Ala His Phe Arg
            260                 265                 270

Lys Tyr His Asp Ala Asn Phe Ile Pro Thr Val Tyr Lys Cys Ser Lys
        275                 280                 285

Cys Gly Lys Gly Phe Ser Arg Trp Ile Asn Leu His Arg His Ser Glu
290                 295                 300

Lys Cys Gly Ser Gly Glu Ala Lys Ser Ala Ala Ser Gly Lys Gly Arg
305                 310                 315                 320

Arg Thr Arg Lys Arg Lys Gln Thr Ile Leu Lys Glu Ala Thr Lys Gly
                325                 330                 335

Gln Lys Glu Ala Ala Lys Gly Trp Lys Glu Ala Ala Asn Gly Asp Gly
            340                 345                 350

Val Ile Ser Ala His Arg Asn Leu Cys Leu Leu Gly Ser Ser Asp Ser
        355                 360                 365

His Ala Ser Val Ser Gly Ala Gly Ile Thr Asp Ala Arg His His Ala
    370                 375                 380

Trp Leu Ile Val Leu Leu Phe Leu Val Glu Met Gly Phe Tyr His Val
385                 390                 395                 400

Ser His Ser

<210> SEQ ID NO 29
<211> LENGTH: 460
<212> TYPE: PRT
<213> ORGANISM: Homo sapiens

<400> SEQUENCE: 29

Met Ser Gly Asp Glu Arg Ser Asp Glu Ile Val Leu Thr Val Ser Asn
1               5                   10                  15

Ser Asn Val Glu Glu Gln Glu Asp Gln Pro Thr Ala Gly Gln Ala Asp
            20                  25                  30

Ala Glu Lys Ala Lys Ser Thr Lys Asn Gln Arg Lys Thr Lys Gly Ala
        35                  40                  45

Lys Gly Thr Phe His Cys Asp Val Cys Met Phe Thr Ser Ser Arg Met
    50                  55                  60
```

Ser Ser Phe Asn Arg His Met Lys Thr His Thr Ser Glu Lys Pro His
 65                  70                  75                  80

Leu Cys His Leu Cys Leu Lys Thr Phe Arg Thr Val Thr Leu Leu Arg
                 85                  90                  95

Asn His Val Asn Thr His Thr Gly Thr Arg Pro Tyr Lys Cys Asn Asp
            100                 105                 110

Cys Asn Met Ala Phe Val Thr Ser Gly Glu Leu Val Arg His Arg Arg
        115                 120                 125

Tyr Lys His Thr His Glu Lys Pro Phe Lys Cys Ser Met Cys Lys Tyr
    130                 135                 140

Ala Ser Val Glu Ala Ser Lys Leu Lys Arg His Val Arg Ser His Thr
145                 150                 155                 160

Gly Glu Arg Pro Phe Gln Cys Gln Cys Ser Tyr Ala Ser Arg Asp
                165                 170                 175

Thr Tyr Lys Leu Lys Arg His Met Arg Thr His Ser Gly Glu Lys Pro
                180                 185                 190

Tyr Glu Cys His Ile Cys His Thr Arg Phe Thr Gln Ser Gly Thr Met
            195                 200                 205

Lys Ile His Ile Leu Gln Lys His Gly Glu Asn Val Pro Lys Tyr Gln
210                 215                 220

Cys Pro His Cys Ala Thr Ile Ile Ala Arg Lys Ser Asp Leu Arg Val
225                 230                 235                 240

His Met Arg Asn Leu His Ala Tyr Ser Ala Ala Glu Leu Lys Cys Arg
                245                 250                 255

Tyr Cys Ser Ala Val Phe His Glu Arg Tyr Ala Leu Ile Gln His Gln
            260                 265                 270

Lys Thr His Lys Asn Glu Lys Arg Phe Lys Cys Lys His Cys Ser Tyr
        275                 280                 285

Ala Cys Lys Gln Glu Arg His Met Thr Ala His Ile Arg Thr His Thr
    290                 295                 300

Gly Glu Lys Pro Phe Thr Cys Leu Ser Cys Asn Lys Cys Phe Arg Gln
305                 310                 315                 320

Lys Gln Leu Leu Asn Ala His Phe Arg Lys Tyr His Asp Ala Asn Phe
                325                 330                 335

Ile Pro Thr Val Tyr Lys Cys Ser Lys Cys Gly Lys Gly Phe Ser Arg
            340                 345                 350

Trp Ile Asn Leu His Arg His Ser Glu Lys Cys Gly Ser Gly Glu Ala
        355                 360                 365

Lys Ser Ala Ala Ser Gly Lys Gly Arg Arg Thr Arg Lys Arg Lys Gln
    370                 375                 380

Thr Ile Leu Lys Glu Ala Thr Lys Gly Gln Lys Glu Ala Ala Lys Gly
385                 390                 395                 400

Trp Lys Glu Ala Ala Asn Gly Asp Gly Val Ile Ser Ala His Arg Asn
                405                 410                 415

Leu Cys Leu Leu Gly Ser Ser Asp Ser His Ala Ser Val Ser Gly Ala
            420                 425                 430

Gly Ile Thr Asp Ala Arg His His Ala Trp Leu Ile Val Leu Leu Phe
        435                 440                 445

Leu Val Glu Met Gly Phe Tyr His Val Ser His Ser
450                 455                 460

<210> SEQ ID NO 30
<211> LENGTH: 427
<212> TYPE: PRT
<213> ORGANISM: Homo sapiens

<400> SEQUENCE: 30

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Glu Gly Val Gln Val Val
                100                 105                 110

Gln Gln Pro Gly Pro Gly Leu Leu Trp Leu Glu Glu Gly Pro Arg Gln
            115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Thr Gly Leu Ile Lys Leu Glu Glu Glu Gln Lys Asn Gln Leu Leu
            180                 185                 190

Ala Glu Arg Thr Lys Glu Gln Leu Phe Phe Val Glu Thr Met Ser Gly
    195                 200                 205

Asp Glu Arg Ser Asp Glu Ile Val Leu Thr Val Ser Asn Ser Asn Val
210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
            245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
            275                 280                 285

Leu Cys Leu Lys Thr Phe Arg Thr Val Thr Leu Leu Arg Asn His Val
            290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
            340                 345                 350

Glu Ala Ser Lys Leu Lys Arg His Val Arg Ser His Thr Gly Glu Arg
            355                 360                 365

Pro Phe Gln Cys Cys Gln Cys Ser Tyr Ala Ser Arg Asp Thr Tyr Lys
    370                 375                 380

Leu Lys Arg His Met Arg Thr His Ser Glu Ala Thr Ser Lys Arg Ser
385                 390                 395                 400

Leu Gln Glu Ile Pro Arg Cys Lys Phe His Pro Asp Cys Leu Gln Met
            405                 410                 415

```
Leu Gln Val Trp Gln Arg Leu Phe Pro Leu Asp
        420             425

<210> SEQ ID NO 31
<211> LENGTH: 332
<212> TYPE: PRT
<213> ORGANISM: Homo sapiens

<400> SEQUENCE: 31

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Glu Gly Val Gln Val Val
            100                 105                 110

Gln Gln Pro Gly Pro Gly Leu Leu Trp Leu Glu Glu Gly Pro Arg Gln
        115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Thr Gly Leu Ile Lys Leu Glu Glu Gln Glu Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
        275                 280                 285

Leu Cys Leu Leu Gly Ser Ser Asp Ser His Ala Ser Val Ser Gly Ala
    290                 295                 300

Gly Ile Thr Asp Ala Arg His His Ala Trp Leu Ile Val Leu Leu Phe
305                 310                 315                 320

Leu Val Glu Met Gly Phe Tyr His Val Ser His Ser
                325                 330

<210> SEQ ID NO 32
<211> LENGTH: 627
<212> TYPE: PRT
<213> ORGANISM: Homo sapiens
```

<400> SEQUENCE: 32

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
                20                  25                  30

Asp Gly Val Cys Arg Glu Lys Asp His Arg Ser Pro Ser Glu Leu Glu
            35                  40                  45

Ala Glu Arg Thr Ser Gly Ala Phe Gln Asp Ser Val Leu Glu Glu Glu
        50                  55                  60

Val Glu Leu Val Leu Ala Pro Ser Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Glu Gly Val Gln Val Val
                100                 105                 110

Gln Gln Pro Gly Pro Gly Leu Leu Trp Leu Glu Glu Gly Pro Arg Gln
                115                 120                 125

Ser Leu Gln Gln Cys Val Ala Ile Ser Ile Gln Gln Glu Leu Tyr Ser
            130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Thr Gly Leu Ile Lys Leu Glu Glu Glu Gln Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
            210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
            275                 280                 285

Leu Cys Leu Lys Thr Phe Arg Thr Val Thr Leu Leu Arg Asn His Val
        290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
            340                 345                 350

Glu Ala Ser Lys Leu Lys Arg His Val Arg Ser His Thr Gly Glu Arg
        355                 360                 365

Pro Phe Gln Cys Cys Gln Cys Ser Tyr Ala Ser Arg Asp Thr Tyr Lys
    370                 375                 380

Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
                405                 410                 415

```
Ile Leu Gln Lys His Gly Glu Asn Val Pro Lys Tyr Gln Cys Pro His
            420                 425                 430

Cys Ala Thr Ile Ile Ala Arg Lys Ser Asp Leu Arg Val His Met Arg
            435                 440                 445

Asn Leu His Ala Tyr Ser Ala Ala Glu Leu Lys Cys Arg Tyr Cys Ser
450                 455                 460

Ala Val Phe His Glu Arg Tyr Ala Leu Ile Gln His Gln Lys Thr His
465                 470                 475                 480

Lys Asn Glu Lys Arg Phe Lys Cys Lys His Cys Ser Tyr Ala Cys Lys
                485                 490                 495

Gln Glu Arg His Met Thr Ala His Ile Arg Thr His Thr Gly Glu Lys
                500                 505                 510

Pro Phe Thr Cys Leu Ser Cys Asn Lys Cys Phe Arg Gln Lys Gln Leu
            515                 520                 525

Leu Asn Ala His Phe Arg Lys Tyr His Asp Ala Asn Phe Ile Pro Thr
530                 535                 540

Val Tyr Lys Cys Ser Lys Cys Gly Lys Gly Phe Ser Arg Trp Ile Leu
545                 550                 555                 560

Trp Val Gly Asn Ser Glu Val Ala Glu Leu Gly Gly Pro Gly Ser Gly
                565                 570                 575

Pro Leu Leu Arg Leu Gln Ser Gly Cys Pro Pro Gly Leu His His Pro
            580                 585                 590

Lys Ala Gly Leu Gly Pro Glu Asp Pro Leu Pro Gly Gln Leu Arg His
            595                 600                 605

Thr Thr Ala Gly Thr Gly Leu Ser Ser Leu Leu Gln Gly Pro Leu Cys
            610                 615                 620

Arg Ala Ala
625

<210> SEQ ID NO 33
<211> LENGTH: 573
<212> TYPE: PRT
<213> ORGANISM: Homo sapiens

<400> SEQUENCE: 33

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Glu Leu Glu
            35                  40                  45

Ala Glu Arg Thr Ser Gly Ala Phe Gln Asp Ser Val Leu Glu Glu Glu
50                  55                  60

Val Glu Leu Val Leu Ala Pro Ser Glu Ser Glu Lys Tyr Ile Leu
65                  70                  75                  80

Thr Leu Gln Thr Val His Phe Thr Ser Glu Ala Val Glu Leu Gln Asp
            85                  90                  95

Met Ser Leu Leu Ser Ile Gln Gln Gln Glu Gly Val Gln Val Val Val
            100                 105                 110

Gln Gln Pro Gly Pro Gly Leu Leu Trp Leu Glu Glu Gly Pro Arg Gln
            115                 120                 125

Ser Leu Gln Gln Cys Val Ala Ile Ser Ile Gln Gln Glu Leu Tyr Ser
130                 135                 140

Pro Gln Glu Met Glu Val Leu Gln Phe His Ala Leu Glu Glu Asn Val
145                 150                 155                 160
```

```
Met Val Ala Ser Glu Asp Ser Lys Leu Ala Val Ser Leu Ala Glu Thr
                165                 170                 175
Thr Gly Leu Ile Lys Leu Glu Glu Gln Glu Lys Asn Gln Leu Leu
            180                 185                 190
Ala Glu Arg Thr Lys Glu Gln Leu Phe Phe Val Glu Thr Met Ser Gly
            195                 200                 205
Asp Glu Arg Ser Asp Glu Ile Val Leu Thr Val Ser Asn Ser Asn Val
210                 215                 220
Glu Glu Gln Glu Asp Gln Pro Thr Ala Gly Gln Ala Asp Ala Glu Lys
225                 230                 235                 240
Ala Lys Ser Thr Lys Asn Gln Arg Lys Thr Lys Gly Ala Lys Gly Thr
                245                 250                 255
Phe His Cys Asp Val Cys Met Phe Thr Ser Ser Arg Met Ser Ser Phe
                260                 265                 270
Asn Arg His Met Lys Thr His Thr Ser Glu Lys Pro His Leu Cys His
                275                 280                 285
Leu Cys Leu Lys Thr Phe Arg Thr Val Thr Leu Leu Arg Asn His Val
            290                 295                 300
Asn Thr His Thr Gly Thr Arg Pro Tyr Lys Cys Asn Asp Cys Asn Met
305                 310                 315                 320
Ala Phe Val Thr Ser Gly Glu Leu Val Arg His Arg Arg Tyr Lys His
                325                 330                 335
Thr His Glu Lys Pro Phe Lys Cys Ser Met Cys Lys Tyr Ala Ser Val
            340                 345                 350
Glu Ala Ser Lys Leu Lys Arg His Val Arg Ser His Thr Gly Glu Arg
            355                 360                 365
Pro Phe Gln Cys Gln Cys Ser Tyr Ala Ser Arg Asp Thr Tyr Lys
            370                 375                 380
Leu Lys Arg His Met Arg Thr His Ser Gly Glu Lys Pro Tyr Glu Cys
385                 390                 395                 400
His Ile Cys His Thr Arg Phe Thr Gln Ser Gly Thr Met Lys Ile His
                405                 410                 415
Ile Leu Gln Lys His Gly Glu Asn Val Pro Lys Tyr Gln Cys Pro His
            420                 425                 430
Cys Ala Thr Ile Ile Ala Arg Lys Ser Asp Leu Arg Val His Met Arg
            435                 440                 445
Asn Leu His Ala Tyr Ser Ala Ala Glu Leu Lys Cys Arg Tyr Cys Ser
450                 455                 460
Ala Val Phe His Glu Arg Tyr Ala Leu Ile Gln His Gln Lys Thr His
465                 470                 475                 480
Lys Asn Glu Lys Arg Phe Lys Cys Lys His Cys Ser Tyr Ala Cys Lys
                485                 490                 495
Gln Glu Arg His Met Thr Ala His Ile Arg Thr His Thr Gly Glu Lys
                500                 505                 510
Pro Phe Thr Cys Leu Ser Cys Asn Lys Cys Phe Arg Gln Lys Gln Leu
            515                 520                 525
Leu Asn Ala His Phe Arg Lys Tyr His Asp Ala Asn Phe Ile Pro Thr
            530                 535                 540
Val Tyr Lys Cys Ser Lys Cys Gly Lys Gly Phe Ser Arg Trp Ile Thr
545                 550                 555                 560
Ser Lys Trp Ser Gly Leu Lys Pro Gln Thr Phe Ile Thr
                565                 570
```

<210> SEQ ID NO 34
<211> LENGTH: 422
<212> TYPE: PRT
<213> ORGANISM: Homo sapiens

<400> SEQUENCE: 34

```
Met Ser Gly Asp Glu Arg Ser Asp Glu Ile Val Leu Thr Val Ser Asn
1               5                   10                  15

Ser Asn Val Glu Glu Gln Glu Asp Gln Pro Thr Ala Gly Gln Ala Asp
            20                  25                  30

Ala Glu Lys Ala Lys Ser Thr Lys Asn Gln Arg Lys Thr Lys Gly Ala
        35                  40                  45

Lys Gly Thr Phe His Cys Asp Val Cys Met Phe Thr Ser Ser Arg Met
    50                  55                  60

Ser Ser Phe Asn Arg His Met Lys Thr His Thr Ser Glu Lys Pro His
65                  70                  75                  80

Leu Cys His Leu Cys Leu Lys Thr Phe Arg Thr Val Thr Leu Leu Arg
                85                  90                  95

Asn His Val Asn Thr His Thr Gly Thr Arg Pro Tyr Lys Cys Asn Asp
            100                 105                 110

Cys Asn Met Ala Phe Val Thr Ser Gly Glu Leu Val Arg His Arg Arg
        115                 120                 125

Tyr Lys His Thr His Glu Lys Pro Phe Lys Cys Ser Met Cys Lys Tyr
    130                 135                 140

Ala Ser Val Glu Ala Ser Lys Leu Lys Arg His Val Arg Ser His Thr
145                 150                 155                 160

Gly Glu Arg Pro Phe Gln Cys Gln Cys Ser Tyr Ala Ser Arg Asp
                165                 170                 175

Thr Tyr Lys Leu Lys Arg His Met Arg Thr His Ser Gly Glu Lys Pro
            180                 185                 190

Tyr Glu Cys His Ile Cys His Thr Arg Phe Thr Gln Ser Gly Thr Met
        195                 200                 205

Lys Ile His Ile Leu Gln Lys His Gly Glu Asn Val Pro Lys Tyr Gln
    210                 215                 220

Cys Pro His Cys Ala Thr Ile Ile Ala Arg Lys Ser Asp Leu Arg Val
225                 230                 235                 240

His Met Arg Asn Leu His Ala Tyr Ser Ala Ala Glu Leu Lys Cys Arg
                245                 250                 255

Tyr Cys Ser Ala Val Phe His Glu Arg Tyr Ala Leu Ile Gln His Gln
            260                 265                 270

Lys Thr His Lys Asn Glu Lys Arg Phe Lys Cys Lys His Cys Ser Tyr
        275                 280                 285

Ala Cys Lys Gln Glu Arg His Met Thr Ala His Ile Arg Thr His Thr
    290                 295                 300

Gly Glu Lys Pro Phe Thr Cys Leu Ser Cys Asn Lys Cys Phe Arg Gln
305                 310                 315                 320

Lys Gln Leu Leu Asn Ala His Phe Arg Lys Tyr His Asp Ala Asn Phe
                325                 330                 335

Ile Pro Thr Val Tyr Lys Cys Ser Lys Cys Gly Lys Gly Phe Ser Arg
            340                 345                 350

Trp Ile Leu Trp Val Gly Asn Ser Glu Val Ala Glu Leu Gly Gly Pro
        355                 360                 365

Gly Ser Gly Pro Leu Leu Arg Leu Gln Ser Gly Cys Pro Pro Gly Leu
    370                 375                 380

His His Pro Lys Ala Gly Leu Gly Pro Glu Asp Pro Leu Pro Gly Gln
```

```
                385                 390                 395                 400
Leu Arg His Thr Thr Ala Gly Thr Gly Leu Ser Ser Leu Leu Gln Gly
                    405                 410                 415

Pro Leu Cys Arg Ala Ala
            420

<210> SEQ ID NO 35
<211> LENGTH: 299
<212> TYPE: PRT
<213> ORGANISM: Homo sapiens

<400> SEQUENCE: 35

Met Phe Thr Ser Ser Arg Met Ser Ser Phe Asn Arg His Met Lys Thr
1               5                   10                  15

His Thr Ser Glu Lys Pro His Leu Cys His Leu Cys Leu Lys Thr Phe
            20                  25                  30

Arg Thr Val Thr Leu Leu Arg Asn His Val Asn Thr His Thr Gly Thr
        35                  40                  45

Arg Pro Tyr Lys Cys Asn Asp Cys Asn Met Ala Phe Val Thr Ser Gly
    50                  55                  60

Glu Leu Val Arg His Arg Arg Tyr Lys His Thr His Glu Lys Pro Phe
65                  70                  75                  80

Lys Cys Ser Met Cys Lys Tyr Ala Ser Val Glu Ala Ser Lys Leu Lys
                85                  90                  95

Arg His Val Arg Ser His Thr Gly Glu Arg Pro Phe Gln Cys Cys Gln
            100                 105                 110

Cys Ser Tyr Ala Ser Arg Asp Thr Tyr Lys Leu Lys Arg His Met Arg
        115                 120                 125

Thr His Ser Gly Glu Lys Pro Tyr Glu Cys His Ile Cys His Thr Arg
    130                 135                 140

Phe Thr Gln Ser Gly Thr Met Lys Ile His Ile Leu Gln Lys His Gly
145                 150                 155                 160

Glu Asn Val Pro Lys Tyr Gln Cys Pro His Cys Ala Thr Ile Ile Ala
                165                 170                 175

Arg Lys Ser Asp Leu Arg Val His Met Arg Asn Leu His Ala Tyr Ser
            180                 185                 190

Ala Ala Glu Leu Lys Cys Arg Tyr Cys Ser Ala Val Phe His Glu Arg
        195                 200                 205

Tyr Ala Leu Ile Gln His Gln Lys Thr His Lys Asn Glu Lys Arg Phe
    210                 215                 220

Lys Cys Lys His Cys Ser Tyr Ala Cys Lys Gln Glu Arg His Met Thr
225                 230                 235                 240

Ala His Ile Arg Thr His Thr Gly Glu Lys Pro Phe Thr Cys Leu Ser
                245                 250                 255

Cys Asn Lys Cys Phe Arg Gln Lys Gln Leu Leu Asn Ala His Phe Arg
            260                 265                 270

Lys Tyr His Asp Ala Asn Phe Ile Pro Thr Val Tyr Lys Cys Ser Lys
        275                 280                 285

Cys Gly Lys Gly Phe Ser Arg Trp Val Leu Tyr
    290                 295

<210> SEQ ID NO 36
<211> LENGTH: 275
<212> TYPE: PRT
<213> ORGANISM: Homo sapiens

<400> SEQUENCE: 36
```

```
Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
                20                  25                  30

Asp Gly Val Cys Arg Glu Lys Asp His Arg Ser Pro Glu Leu Glu
            35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Gln Glu Gly Val Gln Val Val Val
                100                 105                 110

Gln Gln Pro Gly Pro Gly Leu Leu Trp Leu Glu Glu Gly Pro Arg Gln
                115                 120                 125

Ser Leu Gln Gln Cys Val Ala Ile Ser Ile Gln Gln Glu Leu Tyr Ser
            130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Thr Gly Leu Ile Lys Leu Glu Glu Gln Glu Lys Asn Gln Leu Leu
                180                 185                 190

Ala Glu Arg Thr Lys Glu Gln Leu Phe Phe Val Glu Thr Met Ser Gly
    195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Glu Pro
                245                 250                 255

Ser Thr Val Met Ser Ala Cys Ser Pro Leu Leu Glu Cys Gln Val Leu
                260                 265                 270

Ile Val Ile
        275

<210> SEQ ID NO 37
<211> LENGTH: 164
<212> TYPE: PRT
<213> ORGANISM: Homo sapiens

<400> SEQUENCE: 37

Met Phe Thr Ser Ser Arg Met Ser Ser Phe Asn Arg His Met Lys Thr
1               5                   10                  15

His Thr Ser Glu Lys Pro His Leu Cys His Leu Cys Leu Lys Thr Phe
                20                  25                  30

Arg Thr Val Thr Leu Leu Arg Asn His Val Asn Thr His Thr Gly Thr
            35                  40                  45

Arg Pro Tyr Lys Cys Asn Asp Cys Asn Met Ala Phe Val Thr Ser Gly
    50                  55                  60

Glu Leu Val Arg His Arg Arg Tyr Lys His Thr His Glu Lys Pro Phe
65                  70                  75                  80

Lys Cys Ser Met Cys Lys Tyr Ala Ser Val Glu Ala Ser Lys Leu Lys
                85                  90                  95
```

```
Arg His Val Arg Ser His Thr Gly Glu Arg Pro Phe Gln Cys Cys Gln
            100                 105                 110

Cys Ser Tyr Ala Ser Arg Asp Thr Tyr Lys Leu Lys Arg His Met Arg
            115                 120                 125

Thr His Ser Gly Lys Gly Ser Gly Ala Glu Gly Leu Ile Pro Thr Val
            130                 135                 140

Leu Thr Leu Lys Ala Ser Phe Lys Lys Leu Leu Phe Ile Gly Thr Ile
145                 150                 155                 160

Lys Val Gln Arg

<210> SEQ ID NO 38
<211> LENGTH: 426
<212> TYPE: PRT
<213> ORGANISM: Homo sapiens

<400> SEQUENCE: 38

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
            35                  40                  45

Ala Glu Arg Thr Ser Gly Ala Phe Gln Asp Ser Val Leu Glu Glu Glu
            50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
            85                  90                  95

Met Ser Leu Leu Ser Ile Gln Gln Glu Gly Val Gln Val Val Val
            100                 105                 110

Gln Gln Pro Gly Pro Gly Leu Leu Trp Leu Glu Glu Gly Pro Arg Gln
            115                 120                 125

Ser Leu Gln Gln Cys Val Ala Ile Ser Ile Gln Gln Glu Leu Tyr Ser
            130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
            165                 170                 175

Thr Gly Leu Ile Lys Leu Glu Glu Glu Gln Lys Asn Gln Leu Leu
            180                 185                 190

Ala Glu Arg Thr Lys Glu Gln Leu Phe Phe Val Glu Thr Met Ser Gly
            195                 200                 205

Asp Glu Arg Ser Asp Glu Ile Val Leu Thr Val Ser Asn Ser Asn Val
            210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
            245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
            275                 280                 285

Leu Cys Leu Lys Thr Phe Arg Thr Val Thr Leu Leu Arg Asn His Val
            290                 295                 300
```

-continued

```
Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Tyr Lys His
                325                 330                 335

Thr His Glu Lys Pro Phe Lys Cys Ser Met Cys Lys Tyr Ala Ser Val
            340                 345                 350

Glu Ala Ser Lys Leu Lys Arg His Val Arg Ser His Thr Gly Glu Arg
        355                 360                 365

Pro Phe Gln Cys Cys Gln Cys Ser Tyr Ala Ser Arg Asp Thr Tyr Lys
    370                 375                 380

Leu Lys Arg His Met Arg Thr His Ser Gly Lys Gly Ser Gly Ala Glu
385                 390                 395                 400

Gly Leu Ile Pro Thr Val Leu Thr Leu Lys Ala Ser Phe Lys Lys Leu
                405                 410                 415

Leu Phe Ile Gly Thr Ile Lys Val Gln Arg
                420                 425

<210> SEQ ID NO 39
<211> LENGTH: 451
<212> TYPE: PRT
<213> ORGANISM: Homo sapiens

<400> SEQUENCE: 39

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Gln Glu Gly Val Gln Val Val Val
            100                 105                 110

Gln Gln Pro Gly Pro Gly Leu Leu Trp Leu Glu Glu Gly Pro Arg Gln
        115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Ala Gly Leu Ile Lys Leu Glu Glu Glu Gln Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255
```

```
Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
        275                 280                 285

Leu Cys Leu Lys Thr Phe Arg Thr Val Thr Leu Leu Arg Asn His Val
    290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
            340                 345                 350

Glu Ala Ser Lys Leu Lys Arg His Val Arg Ser His Thr Gly Glu Arg
        355                 360                 365

Pro Phe Gln Cys Cys Gln Cys Ser Tyr Ala Ser Arg Asp Thr Tyr Lys
    370                 375                 380

Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
                405                 410                 415

Ile Leu Gln Lys His Gly Glu Asn Val Pro Lys Tyr Gln Cys Pro His
            420                 425                 430

Cys Ala Thr Ile Ile Ala Arg Lys Ser Asp Leu Arg Phe Leu Gly Leu
        435                 440                 445

Pro Phe Pro
    450

<210> SEQ ID NO 40
<211> LENGTH: 145
<212> TYPE: PRT
<213> ORGANISM: Homo sapiens

<400> SEQUENCE: 40

Tyr Lys Cys Ser Lys Cys Gly Lys Gly Phe Ser Arg Trp Ile Asn Leu
1               5                   10                  15

His Arg His Ser Glu Lys Cys Gly Ser Gly Glu Ala Lys Ser Ala Ala
            20                  25                  30

Ser Gly Lys Gly Arg Arg Thr Arg Lys Arg Lys Gln Thr Ile Leu Lys
        35                  40                  45

Glu Ala Thr Lys Gly Gln Lys Glu Ala Ala Lys Gly Trp Lys Glu Ala
    50                  55                  60

Ala Asn Gly Asp Glu Ala Ala Ala Glu Ala Ser Thr Thr Lys Gly
65                  70                  75                  80

Glu Gln Phe Pro Gly Glu Met Phe Pro Val Ala Cys Arg Glu Thr Thr
                85                  90                  95

Ala Arg Val Lys Glu Glu Val Asp Glu Gly Val Thr Cys Glu Met Leu
            100                 105                 110

Leu Asn Thr Met Asp Lys His Leu Ala Gln Met Leu Asp Leu Tyr Gln
        115                 120                 125

Ser Leu Ser Trp Ile Phe Leu Trp Gly Glu Cys Tyr Tyr Lys Ser Tyr
    130                 135                 140

Cys
145

<210> SEQ ID NO 41
<211> LENGTH: 127
```

<212> TYPE: PRT
<213> ORGANISM: Homo sapiens

<400> SEQUENCE: 41

```
Pro Thr Val Tyr Lys Cys Ser Lys Cys Gly Lys Gly Phe Ser Arg Trp
1               5                   10                  15

Ile Asn Leu His Arg His Ser Glu Lys Cys Gly Ser Gly Glu Ala Lys
            20                  25                  30

Ser Ala Ala Ser Gly Lys Gly Arg Arg Thr Arg Lys Arg Lys Gln Thr
        35                  40                  45

Ile Leu Lys Glu Ala Thr Lys Gly Gln Lys Glu Ala Ala Lys Gly Trp
    50                  55                  60

Lys Glu Ala Ala Asn Gly Asp Asp Ile Leu His Arg Cys Trp Ile Cys
65                  70                  75                  80

Ile Lys Val Cys His Gly Phe Ser Phe Gly Glu Ser Ala Ile Ile Asn
                85                  90                  95

Arg Thr Val Ser His Cys Ser Thr Leu Ser Ser Ile Glu Thr Ala Pro
            100                 105                 110

Gly Gln Val Arg Ala Val Arg Ala Leu Gly Asp Ser Val Pro Arg
        115                 120                 125
```

<210> SEQ ID NO 42
<211> LENGTH: 613
<212> TYPE: PRT
<213> ORGANISM: Homo sapiens

<400> SEQUENCE: 42

```
Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
            20                  25                  30

Asp Gly Val Cys Arg Glu Lys Asp His Arg Ser Pro Ser Glu Leu Glu
        35                  40                  45

Ala Glu Arg Thr Ser Gly Ala Phe Gln Asp Ser Val Leu Glu Glu Glu
    50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Gln Glu Gly Val Gln Val Val Val
            100                 105                 110

Gln Gln Pro Gly Pro Gly Leu Leu Trp Leu Glu Glu Gly Pro Arg Gln
        115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Ala Gly Leu Ile Lys Leu Glu Glu Gln Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
```

```
            225                 230                 235                 240
Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270

Asn Arg His Met Lys Thr His Thr Ser Glu Lys Pro His Leu Cys His
        275                 280                 285

Leu Cys Leu Lys Thr Phe Arg Thr Val Thr Leu Leu Arg Asn His Val
    290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
            340                 345                 350

Glu Ala Ser Lys Leu Lys Arg His Val Arg Ser His Thr Gly Glu Arg
        355                 360                 365

Pro Phe Gln Cys Cys Gln Cys Ser Tyr Ala Ser Arg Asp Thr Tyr Lys
    370                 375                 380

Leu Lys Arg His Met Arg Thr His Ser Gly Val His Met Arg Asn Leu
385                 390                 395                 400

His Ala Tyr Ser Ala Ala Glu Leu Lys Cys Arg Tyr Cys Ser Ala Val
                405                 410                 415

Phe His Glu Arg Tyr Ala Leu Ile Gln His Gln Lys Thr His Lys Asn
            420                 425                 430

Glu Lys Arg Phe Lys Cys Lys His Cys Ser Tyr Ala Cys Lys Gln Glu
        435                 440                 445

Arg His Met Thr Ala His Ile Arg Thr His Thr Gly Glu Lys Pro Phe
    450                 455                 460

Thr Cys Leu Ser Cys Asn Lys Cys Phe Arg Gln Lys Gln Leu Leu Asn
465                 470                 475                 480

Ala His Phe Arg Lys Tyr His Asp Ala Asn Phe Ile Pro Thr Val Tyr
                485                 490                 495

Lys Cys Ser Lys Cys Gly Lys Gly Phe Ser Arg Trp Ile Asn Leu His
            500                 505                 510

Arg His Ser Glu Lys Cys Gly Ser Gly Glu Ala Lys Ser Ala Ala Ser
        515                 520                 525

Gly Lys Gly Arg Arg Thr Arg Lys Arg Gln Thr Ile Leu Lys Glu
    530                 535                 540

Ala Thr Lys Gly Gln Lys Glu Ala Ala Lys Gly Trp Lys Glu Ala Ala
545                 550                 555                 560

Asn Gly Asp Glu Ala Ala Ala Glu Ala Ser Thr Thr Lys Gly Glu
                565                 570                 575

Gln Phe Pro Gly Glu Met Phe Pro Val Ala Cys Arg Glu Thr Thr Ala
            580                 585                 590

Arg Val Lys Glu Glu Val Asp Glu Gly Val Thr Cys Glu Met Leu Leu
        595                 600                 605

Asn Thr Met Asp Lys
    610

<210> SEQ ID NO 43
<211> LENGTH: 663
<212> TYPE: PRT
<213> ORGANISM: Homo sapiens
```

<400> SEQUENCE: 43

```
Met Ala Ala Thr Glu Ile Ser Val Leu Ser Glu Gln Phe Thr Lys Ile
1               5                   10                  15
Lys Glu Leu Glu Leu Met Pro Glu Lys Gly Leu Lys Glu Glu Glu Lys
            20                  25                  30
Asp Gly Val Cys Arg Glu Lys Asp His Arg Ser Pro Ser Glu Leu Glu
        35                  40                  45
Ala Glu Arg Thr Ser Gly Ala Phe Gln Asp Ser Val Leu Glu Glu Glu
    50                  55                  60
Val Glu Leu Val Leu Ala Pro Ser Glu Ser Glu Lys Tyr Ile Leu
65                  70                  75                  80
Thr Leu Gln Thr Val His Phe Thr Ser Glu Ala Val Glu Leu Gln Asp
                85                  90                  95
Met Ser Leu Leu Ser Ile Gln Gln Glu Gly Val Gln Val Val
            100                 105                 110
Gln Gln Pro Gly Pro Gly Leu Leu Trp Leu Glu Glu Gly Pro Arg Gln
        115                 120                 125
Ser Leu Gln Gln Cys Val Ala Ile Ser Ile Gln Gln Glu Leu Tyr Ser
    130                 135                 140
Pro Gln Glu Met Glu Val Leu Gln Phe His Ala Leu Glu Glu Asn Val
145                 150                 155                 160
Met Val Ala Ser Glu Asp Ser Lys Leu Ala Val Ser Leu Ala Glu Thr
                165                 170                 175
Ala Gly Leu Ile Lys Leu Glu Glu Gln Glu Lys Asn Gln Leu Leu
            180                 185                 190
Ala Glu Arg Thr Lys Glu Gln Leu Phe Phe Val Glu Thr Met Ser Gly
        195                 200                 205
Asp Glu Arg Ser Asp Glu Ile Val Leu Thr Val Ser Asn Ser Asn Val
    210                 215                 220
Glu Glu Gln Glu Asp Gln Pro Thr Ala Gly Gln Ala Asp Ala Glu Lys
225                 230                 235                 240
Ala Lys Ser Thr Lys Asn Gln Arg Lys Thr Lys Gly Ala Lys Gly Thr
                245                 250                 255
Phe His Cys Asp Val Cys Met Phe Thr Ser Ser Arg Met Ser Ser Phe
            260                 265                 270
Asn Arg His Met Lys Thr His Thr Ser Glu Lys Pro His Leu Cys His
        275                 280                 285
Leu Cys Leu Lys Thr Phe Arg Thr Val Thr Leu Leu Arg Asn His Val
    290                 295                 300
Asn Thr His Thr Gly Thr Arg Pro Tyr Lys Cys Asn Asp Cys Asn Met
305                 310                 315                 320
Ala Phe Val Thr Ser Gly Glu Leu Val Arg His Arg Arg Tyr Lys His
                325                 330                 335
Thr His Glu Lys Pro Phe Lys Cys Ser Met Cys Lys Tyr Ala Ser Val
            340                 345                 350
Glu Ala Ser Lys Leu Lys Arg His Val Arg Ser His Thr Gly Glu Arg
        355                 360                 365
Pro Phe Gln Cys Cys Gln Cys Ser Tyr Ala Ser Arg Asp Thr Tyr Lys
    370                 375                 380
Leu Lys Arg His Met Arg Thr His Ser Gly Glu Lys Pro Tyr Glu Cys
385                 390                 395                 400
His Ile Cys His Thr Arg Phe Thr Gln Ser Gly Thr Met Lys Ile His
                405                 410                 415
```

```
Ile Leu Gln Lys His Gly Glu Asn Val Pro Lys Tyr Gln Cys Pro His
            420                 425                 430
Cys Ala Thr Ile Ile Ala Arg Lys Ser Asp Leu Arg Val His Met Arg
        435                 440                 445
Asn Leu His Ala Tyr Ser Ala Ala Glu Leu Lys Cys Arg Tyr Cys Ser
    450                 455                 460
Ala Val Phe His Glu Arg Tyr Ala Leu Ile Gln His Gln Lys Thr His
465                 470                 475                 480
Lys Asn Glu Lys Arg Phe Lys Cys Lys His Cys Ser Tyr Ala Cys Lys
                485                 490                 495
Gln Glu Arg His Met Thr Ala His Ile Arg Thr His Thr Gly Glu Lys
            500                 505                 510
Pro Phe Thr Cys Leu Ser Cys Asn Lys Cys Phe Arg Gln Lys Gln Leu
        515                 520                 525
Leu Asn Ala His Phe Arg Lys Tyr His Asp Ala Asn Phe Ile Pro Thr
    530                 535                 540
Val Tyr Lys Cys Ser Lys Cys Gly Lys Gly Phe Ser Arg Trp Ile Asn
545                 550                 555                 560
Leu His Arg His Ser Glu Lys Cys Gly Ser Gly Glu Ala Lys Ser Ala
                565                 570                 575
Ala Ser Gly Lys Gly Arg Arg Thr Arg Lys Arg Lys Gln Thr Ile Leu
            580                 585                 590
Lys Glu Ala Thr Lys Gly Gln Lys Glu Ala Ala Lys Gly Trp Lys Glu
        595                 600                 605
Ala Ala Asn Gly Asp Glu Ala Ala Glu Glu Ala Ser Thr Thr Lys
    610                 615                 620
Gly Glu Gln Phe Pro Gly Glu Met Phe Pro Val Ala Cys Arg Glu Thr
625                 630                 635                 640
Thr Ala Arg Val Lys Glu Glu Val Asp Glu Gly Val Thr Cys Glu Met
                645                 650                 655
Leu Leu Asn Thr Met Asp Lys
            660

<210> SEQ ID NO 44
<211> LENGTH: 3500
<212> TYPE: DNA
<213> ORGANISM: Homo sapiens

<400> SEQUENCE: 44
ggcaccagac gcggtgcacg aggcagagcc acaagccaaa gacggagtgg gccgagcatt      60
ccggccacgc cttccgcggc caagtcatta tggcagccac tgagatctct gtcctttctg     120
agcaattcac caagatcaaa gaactcgagt tgatgccgga aaaaggcctg aaggaggagg     180
aaaaagacgg agtgtgcaga gagaaagacc atcggagccc tagtgagttg gaggccgagc     240
gtacctctgg ggccttccag acagcgtcc tggaggaaga agtggagctg tgctggccc      300 cctcggagga gagcgagaag tacatcctga ccctgcagac ggtgcacttc acttctgaag     360
ctgtggagtt gcaggatatg agcttgctga gcatacagca gcaagaaggg gtgcaggtgg     420
tggtgcaaca gcctggccct gggttgctgt ggcttgagga agggccccgg cagagcctgc     480
agcagtgtgt ggccattagt atccagcaag agctgtactc cccgcaagag atggaggtgt     540
tgcagttcca cgctctagag gagaatgtga tggtggccag tgaagacagt aagttagcgg     600
tgagcctggc tgaaactgct ggactgatca agctcgagga agagcaggag aagaaccagt     660
tattggctga agaacaaag gagcagctct tttttgtgga acaatgtca ggagatgaaa     720
```

```
gaagtgacga aattgttctc acagtttcaa attcaaatgt ggaagaacaa gaggatcaac    780
ctacagctgg tcaagcagat gctgaaaagg ccaaatctac aaaaaatcaa agaaagacaa    840
agggagcaaa aggaaccttc cactgtgatg tctgcatgtt caccctcttct agaatgtcaa    900 gttttaatcg tcatatgaaa actcacacca gtgagaagcc tcacctgtgt cacctctgcc    960 tgaaaaccctt ccgtacggtc actctgctgc ggaaccatgt taacacccac acaggaacca   1020
ggccctacaa gtgtaacgac tgcaacatgg catttgtcac cagtggagaa ctcgtccgac   1080
acaggcgcta taaacatact catgagaaac cctttaaatg ttccatgtgc aagtatgcca   1140
gtgtggaggc aagtaaattg aagcgccatg tccgatccca cactggggag cgccccttc    1200 agtgttgcca gtgcagctat gccagcagag atacctacaa gctgaaacgc cacatgagaa   1260
cgcactcagg tgagaagcct tacgaatgcc acatctgcca cacccgcttc acccagagcg   1320
ggaccatgaa aatacatatt ctgcagaaac acggcgaaaa tgtccccaaa taccagtgtc   1380
cccattgtgc caccatcatt gcacggaaaa gcgacctacg tgtgcatatg cgcaacttgc   1440
atgcttacag cgctgcagag ctgaaatgcc gctactgttc tgctgtcttc catgaacgct   1500
atgccctcat tcagcaccag aaaactcata agaatgagaa gaggttcaag tgcaaacact   1560
gcagttatgc ctgcaagcag aacgtcata tgaccgctca cattcgtacc cacactggag    1620
agaaaccatt cacctgcctt tcttgcaata aatgtttccg acagaagcaa cttctaaacg   1680
ctcacttcag gaaataccac gatgcaaatt tcatcccgac tgtttacaaa tgctccaagt   1740
gtggcaaagg cttttcccgc tggattaacc tgcacagaca ttcggagaag tgtggatcag   1800
gggaagcaaa gtcggctgct tcaggaaagg gaagaagaac aagaaagagg aagcagacca   1860
tcctgaagga agccacaaag ggtcagaagg aagctgcgaa gggatggaag gaagccgcga   1920
acggagacga agctgctgct gaggaggctt ccaccacgaa gggagaacag ttcccaggag   1980
agatgtttcc tgtcgcctgc agagaaacca cagccagagt caaagaggaa gtggatgaag   2040
gcgtgacctg tgaaatgctc ctcaacacga tggataagtg agagggattc gggttgcgtg   2100
ttcactgccc ccaattccta aagcaagtta gaagttttta gcatttaagg tgtgaaatgc   2160
tcctcaacac gatggataag tgagagagag tcaggttgca tgttcactgc ccctaattcc   2220
taaagcaagt tagaaatttt tagcattttc tttgaaacaa ttaagttcat gacaatggat   2280
gacacaagtt tgaggtagtg tctagaattg ttctcctgtt tgtagctgga tatttcaaag   2340
aaacattgca ggtattttat aaaagtttta aaccttgaat gagagggtaa cacctcaaac   2400
ctatggattc attcacttga tattggcaag gtggcccaca atgagtgagt agtgattttt   2460
ggatatttca aaatagtcta gaccagctag tgcttccaca gtcaaagctg acatttttta   2520
tgttgcatta tatacaccca tgatatttct aataatatat ggttttaaac attaaagaca   2580 aatgtttta tacaaatgaa ttttctacaa aatttaaagc taccataatg cttttaatta    2640
gttctaaatt caaccaaaaa atgttttact cttataaaaa ggaaaactga gtaggaaatg   2700
aaatactaga ttagactaga aaataaggaa taaatcgatt ttactttggt ataggagcaa   2760
ggttcacctt tagattttg tattctcttt taattatgct ccttggcagg tatgaaattg    2820
ccctggttac attccattat tgcttattag tatttcactc cataacccctt ttttctgcta   2880 aaactactct ttttatattt gtaaaataat tggcagagtg agaagaaaca taaaatcaga   2940
taaggcaaat gtgtacctgt aaggaatttg tacttttca taatgcccag tgattagtga    3000
gtatttccct tttgccagtt gacaagattt ttccacccctc gagcagcgtg agagatgcct   3060 cttttaacact tgaaattcat ttctatctgg atacagaggc agattttcct tcattgctta   3120
```

```
gttgagcagt tgttttgct gccaacctgt ctccacccct gtatttcaag atcattgata    3180
agccctaaat tcaaattctt aagatatgga ccttttattg aaaatatcac aagttcagaa    3240
tccctataca atgtgaatat gtggaaataa tttcccagca ggaagagcat tatattctct    3300
ttgtaccagc aaattaattt aactcaactc acatgagatt taaattctgt gggctgtagt    3360
atgccatcat tgtgactgaa tttgtgcaat ggtttcttaa ttttttttact gttatttaaa    3420 gatgttttac ataattcaat aaaatgaaat gacttaaaat tgcaaaaaaa aaaaaaaaa     3480 aaaaaaaaaa aaaaaaaaa                                                  3500
```

<210> SEQ ID NO 45
<211> LENGTH: 36
<212> TYPE: PRT
<213> ORGANISM: Homo sapiens

<400> SEQUENCE: 45

Cys Lys Tyr Ala Ser Val Glu Val Lys Pro Phe Leu Asp Leu Lys Leu
1               5                   10                  15

His Gly Ile Leu Val Glu Ala Ala Val Gln Val Thr Pro Ser Val Thr
            20                  25                  30

Asn Ser Arg Ile
        35

<210> SEQ ID NO 46
<211> LENGTH: 22
<212> TYPE: PRT
<213> ORGANISM: Homo sapiens

<400> SEQUENCE: 46

Cys Tyr Lys Gln Ala Phe Tyr Tyr Ser Tyr Lys Ile Tyr Ile Gly Asn
1               5                   10                  15

Asn Met His Ser Leu Leu
            20

<210> SEQ ID NO 47
<211> LENGTH: 24
<212> TYPE: PRT
<213> ORGANISM: Homo sapiens

<400> SEQUENCE: 47

Cys Leu Leu Gly Ser Ser Asp Ser His Ala Ser Val Ser Gly Ala Gly
1               5                   10                  15

Ile Thr Asp Ala Arg His His Ala
            20

<210> SEQ ID NO 48
<211> LENGTH: 28
<212> TYPE: PRT
<213> ORGANISM: Homo sapiens

<400> SEQUENCE: 48

Cys Ile Thr Asp Ala Arg His His Ala Trp Leu Ile Val Leu Leu Glu
1               5                   10                  15

Leu Val Glu Met Gly Phe Tyr His Val Ser His Ser
            20                  25

<210> SEQ ID NO 49
<211> LENGTH: 27
<212> TYPE: PRT
<213> ORGANISM: Homo sapiens

<400> SEQUENCE: 49

```
Cys Pro Pro Gly Leu His His Pro Lys Ala Gly Leu Gly Pro Glu Asp
1               5                   10                  15

Pro Leu Pro Gly Gln Leu Arg His Thr Ala Gly
            20              25

<210> SEQ ID NO 50
<211> LENGTH: 21
<212> TYPE: PRT
<213> ORGANISM: Homo sapiens

<400> SEQUENCE: 50

Gly Gln Leu Arg His Thr Thr Ala Gly Thr Gly Leu Ser Ser Leu Leu
1               5                   10                  15

Gln Gly Pro Leu Cys
            20
```